United States Patent
Elford et al.

(10) Patent No.: US 11,384,082 B2
(45) Date of Patent: Jul. 12, 2022

(54) HYDRATES OF POLYMORPHS OF 6-(1H-INDAZOL-6-YL)-N-(4-MORPHOLINOPHENYL)-2,3-DIHYDROIMIDAZO[1,2-A]PYRAZIN-8-AMINE BISEMSYLATE AS SYK INHIBITORS

(71) Applicant: Kronos Bio, Inc., San Mateo, CA (US)

(72) Inventors: Tim G. Elford, Alberta (CA); Peter Chee-Chu Fung, San Mateo, CA (US); Paul Robert Hartmeier, Pittsburgh, PA (US); Jesper Alexis Jernelius, San Francisco, CA (US); Henry Morrison, Dublin, CA (US)

(73) Assignee: Kronos Bio, Inc., San Mateo, CA (US)

( * ) Notice: Subject to any disclaimer, the term of this patent is extended or adjusted under 35 U.S.C. 154(b) by 0 days.

(21) Appl. No.: 16/641,331

(22) PCT Filed: Aug. 10, 2018

(86) PCT No.: PCT/US2018/046314
§ 371 (c)(1),
(2) Date: Feb. 24, 2020

(87) PCT Pub. No.: WO2019/040298
PCT Pub. Date: Feb. 28, 2019

(65) Prior Publication Data
US 2020/0277293 A1    Sep. 3, 2020

Related U.S. Application Data

(60) Provisional application No. 62/550,346, filed on Aug. 25, 2017.

(51) Int. Cl.
C07D 487/04 (2006.01)

(52) U.S. Cl.
CPC ........ *C07D 487/04* (2013.01); *C07B 2200/13* (2013.01)

(58) Field of Classification Search
CPC .................................................. C07D 487/04
USPC ....................................................... 544/350
See application file for complete search history.

(56) References Cited

U.S. PATENT DOCUMENTS

| | | | |
|---|---|---|---|
| 2,175,837 A | 10/1939 | Hanna | |
| 2,714,414 A | 8/1955 | De Ganahl | |
| 4,337,609 A | 7/1982 | Foster et al. | |
| 5,593,997 A | 1/1997 | Dow et al. | |
| 5,658,857 A | 8/1997 | Andree et al. | |
| 5,783,576 A | 7/1998 | Roos et al. | |
| 5,846,514 A | 12/1998 | Foster et al. | |
| 6,334,997 B1 | 1/2002 | Foster et al. | |
| 6,919,340 B2 | 7/2005 | Currie et al. | |
| 6,919,341 B2 | 7/2005 | Paruch et al. | |
| 7,160,885 B2 | 1/2007 | Currie et al. | |
| 7,189,723 B2 | 3/2007 | Mitchell et al. | |
| 7,259,164 B2 | 8/2007 | Mitchell et al. | |
| 7,312,341 B2 | 12/2007 | DeSimone et al. | |
| 7,405,295 B2 | 7/2008 | Currie et al. | |
| 8,440,667 B2 | 5/2013 | Mitchell et al. | |
| 8,450,321 B2 | 5/2013 | Mitchell et al. | |
| 8,455,493 B2 | 6/2013 | Mitchell et al. | |
| 8,697,699 B2 | 4/2014 | Mitchell et al. | |
| 8,748,607 B2 | 6/2014 | Mitchell et al. | |
| 8,765,761 B2 | 7/2014 | Mitchell et al. | |
| 8,796,270 B2 | 8/2014 | Mitchell | |
| 8,962,835 B2 | 2/2015 | Mitchell et al. | |
| 9,120,811 B2 | 9/2015 | Mitchell et al. | |
| 9,212,191 B2 | 12/2015 | Mitchell et al. | |
| 9,290,505 B2 | 3/2016 | Blomgren et al. | |
| 9,376,441 B2 | 6/2016 | Currie et al. | |
| 9,382,256 B2 | 7/2016 | Casteel et al. | |
| 9,504,684 B2 | 11/2016 | Blomgren et al. | |
| 9,562,056 B2 | 2/2017 | Blomgren et al. | |

(Continued)

FOREIGN PATENT DOCUMENTS

| | | |
|---|---|---|
| CA | 2175837 | 5/1995 |
| CN | 101124227 | 2/2008 |

(Continued)

OTHER PUBLICATIONS

Ackler et al., 2012, Navitoclax (ABT-263) and bendamustine rituximab induce enhanced killing of non-Hodgkin's lymphoma tumours in vivo, British Journal of Pharmacology, 167:881-891.

Al-Dabbagh et al., 1984, Species Differences in Oxidative Drug Metabolism: Some Basic Considerations, Archives of Toxicology, Suppl. 7:219-231.

Ashizawa, 2002, en/kesshokei no saitekika to kesshokagijutsu (optimization of salt/crystal form and crystallization technique), Pharm Tech Japan, 18(10):81-96.

(Continued)

*Primary Examiner* — Douglas M Willis
(74) *Attorney, Agent, or Firm* — Knobbe, Martens, Olson & Bear LLP

(57) ABSTRACT

Polymorphs of a bis-mesylate salt of a compound of Formula IA:

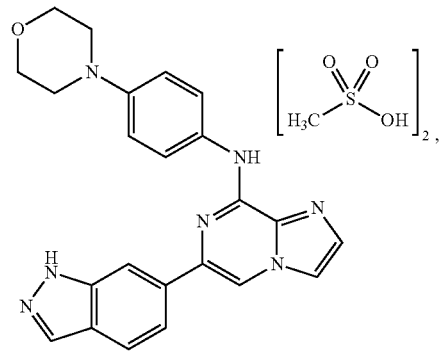

are provided. Also provided are process for making the polymorphs and methods of use thereof.

21 Claims, 20 Drawing Sheets

(56) References Cited

U.S. PATENT DOCUMENTS

| | | |
|---|---|---|
| 9,567,348 B2 | 2/2017 | Mitchell et al. |
| 9,657,023 B2 | 5/2017 | Elford et al. |
| 9,687,492 B2 | 6/2017 | Di Paolo et al. |
| 9,707,236 B2 | 7/2017 | Di Paolo et al. |
| 9,796,718 B2 | 10/2017 | Mitchell et al. |
| 9,918,939 B2 | 3/2018 | Casteel |
| 9,949,932 B2 | 4/2018 | Casteel |
| 9,968,601 B2 | 5/2018 | Blomgren et al. |
| 9,974,792 B2 | 5/2018 | Di Paolo |
| 10,080,756 B2 | 9/2018 | Di Paolo et al. |
| 10,092,582 B2 | 10/2018 | Blomgren et al. |
| 10,093,684 B2 | 10/2018 | Blomgren et al. |
| 10,266,539 B2 | 4/2019 | Elford et al. |
| 2003/0212073 A1 | 11/2003 | Currie et al. |
| 2004/0063715 A1 | 4/2004 | Paruch et al. |
| 2004/0067951 A1 | 4/2004 | DeSimone et al. |
| 2004/0072081 A1 | 4/2004 | Coleman et al. |
| 2004/0072835 A1 | 4/2004 | Paruch et al. |
| 2004/0102455 A1 | 5/2004 | Burns et al. |
| 2004/0220189 A1 | 11/2004 | Sun et al. |
| 2005/0009832 A1 | 1/2005 | Sun et al. |
| 2005/0054648 A1 | 3/2005 | Mitchell et al. |
| 2005/0054649 A1 | 3/2005 | Currie et al. |
| 2005/0085484 A1 | 4/2005 | Mitchell et al. |
| 2005/0090499 A1 | 4/2005 | Currie et al. |
| 2005/0101604 A1 | 5/2005 | Currie et al. |
| 2005/0222199 A1 | 10/2005 | Havman et al. |
| 2005/0288295 A1 | 12/2005 | Currie et al. |
| 2006/0069084 A1 | 3/2006 | Burns et al. |
| 2006/0084650 A1 | 4/2006 | Donq et al. |
| 2006/0183746 A1 | 8/2006 | Currie et al. |
| 2007/0027135 A1 | 2/2007 | Bruncko et al. |
| 2007/0072860 A1 | 3/2007 | Bruncko et al. |
| 2007/0117804 A1 | 5/2007 | Zhao et al. |
| 2009/0221612 A1 | 9/2009 | Mitchell et al. |
| 2010/0305122 A1 | 9/2010 | Bruncko et al. |
| 2010/0305125 A1 | 12/2010 | Borchardt et al. |
| 2011/0002989 A1 | 1/2011 | Curatolo et al. |
| 2012/0157470 A1 | 6/2012 | Catron et al. |
| 2013/0267496 A1 | 10/2013 | Mitchell et al. |
| 2013/0338142 A1 | 12/2013 | Blomgren et al. |
| 2014/0051696 A1 | 2/2014 | Lannutti et al. |
| 2014/0148430 A1 | 5/2014 | Blomgren et al. |
| 2015/0038504 A1 | 2/2015 | Casteel et al. |
| 2015/0038505 A1 | 2/2015 | Elford et al. |
| 2016/0168155 A1 | 6/2016 | Fung et al. |
| 2016/0220573 A1 | 8/2016 | Di Paolo et al. |
| 2016/0368918 A1 | 12/2016 | Blomgren et al. |
| 2016/0375019 A1 | 12/2016 | Di Paolo et al. |
| 2017/0035755 A1 | 2/2017 | Blomgren et al. |
| 2018/0117052 A1 | 5/2018 | Di Paolo |

FOREIGN PATENT DOCUMENTS

| | | |
|---|---|---|
| EP | 0 480 713 | 4/1992 |
| WO | WO 88/04298 | 6/1988 |
| WO | WO 95/12592 | 5/1995 |
| WO | WO 95/12594 | 5/1995 |
| WO | WO 96/04298 | 2/1996 |
| WO | WO 96/034866 | 11/1996 |
| WO | WO 99/28322 | 6/1999 |
| WO | WO 01/27119 | 4/2001 |
| WO | WO 01/83485 | 11/2001 |
| WO | WO 02/10170 | 2/2002 |
| WO | WO 02/030428 | 4/2002 |
| WO | WO 02/060492 | 8/2002 |
| WO | WO 02/066481 | 8/2002 |
| WO | WO 02/076985 | 10/2002 |
| WO | WO 03/070732 | 8/2003 |
| WO | WO 03/089434 | 10/2003 |
| WO | WO 04/022562 | 3/2004 |
| WO | WO 04/026310 | 4/2004 |
| WO | WO 04/026867 | 4/2004 |
| WO | WO 04/026877 | 4/2004 |
| WO | WO 04/072080 | 8/2004 |
| WO | WO 05/005429 | 1/2005 |
| WO | WO 05/014599 | 2/2005 |
| WO | WO 05/019220 | 3/2005 |
| WO | WO 05/047290 | 5/2005 |
| WO | WO 05/085252 | 9/2005 |
| WO | WO 06/044687 | 4/2006 |
| WO | WO 06/053121 | 5/2006 |
| WO | WO 08/025821 | 3/2008 |
| WO | WO 08/033854 | 3/2008 |
| WO | WO 09/039397 | 3/2009 |
| WO | WO 09/070639 | 6/2009 |
| WO | WO 09/077334 | 6/2009 |
| WO | WO 09/156284 | 12/2009 |
| WO | WO 10/000633 | 1/2010 |
| WO | WO 10/006947 | 1/2010 |
| WO | WO 10/027500 | 3/2010 |
| WO | WO 11/074961 | 6/2011 |
| WO | WO 12/147832 | 11/2012 |
| WO | WO 14/028665 | 2/2015 |
| WO | WO-2019040298 A1 * | 2/2019 ........... C07D 487/04 |

OTHER PUBLICATIONS

Bastin et al., 200-, Salt Selection and Optimisation Procedures for Pharmaceutical New Chemical Entities, Organic Process Research and Development, American Chemical Society, 4(5):427-435.

Berge et al., Jan. 1977, Pharmaceutical Salts, Journal of Pharmaceutical Sciences, 66(1):1-19.

Blazar et al., 2013, Advances in graft-versus host disease biology and therapy, Nat Rev Immunol., 12(6):443-458.

Bouloc et al., 2010, Structure-based design of imidazo[1,2-α]pyrazine derivatives as selective inhibitors of Aurora kinase in cells. Bioorganic & Medicinal Chemistry Letters, 20:5988-5993.

Brittain, 2009, Theory and principles of polymorphic systems, in Polymorphism in Pharmaceutical Solids, Informa Healthcare, New York, pp. 1-23.

Buchner et al., Jun. 2010, Spleen tyrosine kinase inhibition prevents chemokine- and integrin-mediated stromal protective effects in chronic lymphocytic leukemia, Blood, 115(22):4497-4506.

Bundgaard, 1985, *Design of Prodrugs*, Elsevier Science Publishers, B.V., The Netherlands, p. 1.

Burke et al., 2014, A potential therapeutic strategy for chronic lymphocytic leukemia by combining Idelalisib and GS-9973, a novel spleen tyrosine kinase (Syk) inhibitor, Oncotarget, 5(4):908-915.

Burrell et al., 2013, The causes and consequences of genetic heterogeneity in cancer evolution, Nature, 501:338-345.

CancerConnect.com, Aug. 17, 2013, Ibrutinib Highly Active in Patients with Chronic Lymphocytic Leukemia with 17p Deletion, 2 pp.

CiinicalTrials.gov, Jun. 2013, A Phase 2 of GS-9973 in Subjects With Relapsed or Refractory Hematologic Malignancies, NCT01799889, 5 pp.

Currie et al., 2014, Discovery of GS-9973, a Selective and Orally Efficacious Inhibitor of Spleen Tyrosine Kinase, J. Med. Chem., 57:3856-3873.

Dean, 2000, Recent Advances in the Synthesis and Applications of Radiolabeled Compounds for Druo Discovery and Development, Curr. Pharm Des. 6(10):Preface, 1 p.

Ding et al., 2002, A Combinatorial Scaffold Approach Toward Kinase-Directed Heterocvcle Libraries, J. Am Chem Soc., 124(8):1594-1596.

Elder et al., 2010, The Utility of Sulfonate Salts in Drug Development, J Pharm Sci, 99(7)2948-2961.

Evans, 1981, Synthesis of Radiolabeled Compounds, J. Radioanal. Chem. 64(1-2):9-32.

Flynn, Aug. 2014, B cells, T follicular helpers, and germinal centers as facilitators of chronic Graft-versus-Host disease. Doctoral Dissertation, University of Minnesota, 182 pp.

Gavezzotti, 1994, Are Crystal Structures Predictable? Acc. Chem. Res. 27(10):309-314.

GenBank Accession No. AY050647.1, created on Oct. 7, 2001, located at<http://www.ncbi.nlm.nih.qov/nuccore/AY050647.1>, last visited on Dec. 28, 2011, 1 paqe.

(56) References Cited

OTHER PUBLICATIONS

Hackam et al., 2006, Translation of Research Evidence From Animals to Humans, JAMA, 296(14):1731-1732.

Hill et al., 2013, B-Cell Antigen Receptor Signaling in Chronic Lymphocytic Leukemia: TherapeuticTargets and Translational Opportunities, International Reviews of Immunology, 32:377-396.

Hirayama, Jul. 25, 2008, Handbook for creating organic compound crystals—principle and technical know-how, Maruzen KK, pp. 17-23, 37-40, 45-51 and 57-65.

Jeffrey et al., 1998, Phosphodiesterase III and V Inhibitors on Pulmonary Artery from Pulmonary Hypertensive Rats: Differences Between Early and established Pulmonary Hypertension, J. Cardiovascular Pharmacology, 32(2):213-219.

Jordan Mar. 2003, Tamoxifen: A Most Unlikely Pioneering Medicine, Nature Reviews: Drug Discovery 2:205-213.

Kabalka et al., 1989, The Synthesis of Radiolabeled Compounds via Organometallic Intermediates, Tetrahedron 45(21):6601-6621.

Kojima, Sep. 2008, Iyakuhin Kaihatsu ni okeru kettushousei sentaku no kouritsuka womezashite (Aiming at efficient crystallinity selection in medicine development), Journal of Pharmaceutical Science and Technology, Japan, 68(5)344-349.

Krisenko et al., Jan. 2015, Calling in SYK: SYK's Dual Role as a Tumor Promoter and Tumor Suppressor in Cancer, Biochim Biophys Acta., 1853(1):254-263.

Kuhnz et al., Jun. 11, 1998, Predicting the Oral Bioavailab ty of 19-Nortestosterone Progestins In Vivo From Their Metabolic Stab ty in Human Liver Microsomal Preparation In Vitro, The American Society for Pharmacology and Experimental Therapeutics, 26(11):1120-1127.

Le Huu et al., 2014, Blockade of Syk ameliorates the development of murine sclerodermatous chronic graft-vershost disease, Journal of Dermatological Science, 74:214-221.

Lumma et al., 1983, Piperazinylimidazo [1,2-α]pyrazines with Selective affinity for in Vitro adrenerqic Receptor Subtypes, J. Med. Chem. 26(3):357-363.

Ma et al., 2011, Signal transduction inhibitors in chronic lymphocytic leukemia, Current Opinion in Oncology, 23:601-608.

Merino et al., 2012, Bcl-2, Bcl-xl, and Bcl-w are not equivalent targets of ABT-737 and navitoclax (ABT-263) in lymphoid and leukemic cells, Blood. 119(24):5807-5816.

National Cancer Institute, 2017, Cancer Types, A to Z List of Cancer Types, 8 pp.

Oracova et al., 1996, Drug-Protein Binding Studies New Trends in Analytical and Experimental Methodology, J Chromatograpny B, 677:1-28.

Owen et al., 2012, Obinutuzumab for the treatment of lymphoproliferative disorders, Expert Opinion Biol. Ther. 12(3):343-351.

Paulekuhn et al., 2007, Trends in Active Pharmaceutical Ingredient Salt Selection based on Analysis of the Orange Book Database, J. Med. Chem., 50:6665-6672.

Roberts et al., 2012, Substantial Susceptibility of Chronic Lymphocytic Leukemia to BCL2 Inhibition:Results of a Phase I Study of Navitoclax in Patients With Relapsed or Refractory Disease. J Clin Oncol, 30:488-496.

Serajuddin, 2007, Salt formation to improve drug solubility, Advanced Drug Delivery Reviews, 59:603-616.

Silverman, 1992, Prodrugs and drug delivery systems, in The Organic Chemistry of Drug Design and Drug Action, Academic Press, Inc., San Diego, CA, pp. 352-400.

Stenberg et al., 2000, KinMutBase, a Database of Human Disease-Causing Protein Kinase Mutations, Nucleic Acids Research 28(1):369-371.

Takata, 2007, API form screening and selection in drug discovery stage, Pharmstage, 6(10):20-25.

Taylor et al., 1984, Hydrogen-Bond Geometry in Organic Crystals, Acc. Chem Res. 17:320-326.

Vassilev et al., 2004, Therapeutic Potential of Inhibiting Bruton's Tyrosine Kinase, (BTK), Current Pharmaceutical Design, 10:1757-1766.

Vippagunta et al., 2011, Crystalline solids, Advanced Drug Delivery Reviews 48:3-26.

Vitze et al., 1999, New Imidazo [1,2-a]pyrazine Derivatives with Bronchodilatory andCyclic Nucleotide Phosphodiesterase Inh tory Activities, Bioorganic and Medicinal Chemistrv 7:1059-1065.

Willander et al, 2013, NOTCH1 Mutations Influence Survival in Chronic Lymphocytic Leukemia Patients, BMC Cancer , 13:274, 6 pp.

Zaragoza Dorwald, 2005, Side Reactions in Organic Synthesis: A Guide to Successful Synthesis Design, Weinheim: WILEY-VCH Verlag GmbH & Co., Preface, 2 p.

Balbach et al., 2004, Pharmaceutical evaluation of early development candidates: the 100 mg approach, International Journal of Pharmaceutics, 275:1-12.

Caira, 1998, Crystalline polymorphism of organic compounds, in Weber et al., eds., Design of Organic Solids, Springer.

Singhal et al., 2004, Drug polymorphism and dosage form design: a practical perspective, Advanced Drug Dlivery Reviews, 56:335-347.

International Search Report and Written Opinion dated Feb. 28, 2019 in application No. PCT/US2018/046314.

Byrn et al., 1995, Pharmaceutical solids: a strategic approach to regulatory considerations, Pharma. Res. 12(7):945-954.

Hilfiker, ed., 2006, Polymorphism in the Pharmaceutical Industry, Wiley-VCH Verlag GmbH & Co. KGaA, Weinheim, Germany (TOC).

* cited by examiner

Exo up

HYDRATES OF POLYMORPHS OF 6-(1H-INDAZOL-6-YL)-N-(4-MORPHOLINO-PHENYL)-2,3-DIHYDROIMIDAZO[1,2-A]PYR-AZIN-8-AMINE BISEMSYLATE AS SYK INHIBITORS

BACKGROUND

The present disclosure relates to polymorphs and polymorph pharmaceutical compositions of compounds that inhibit Spleen Tyrosine Kinase (Syk) activity. The disclosure also relates to methods of preparing such polymorphs and polymorph pharmaceutical compositions, and the use of such polymorphs and pharmaceutical compositions in treating subjects with various diseases, including cancer and inflammatory conditions.

The inhibition of Spleen Tyrosine Kinase (Syk) activity may be useful for treating certain types of cancer and autoimmune diseases. One such compound that has been found to inhibit Syk activity is represented by Formula I:

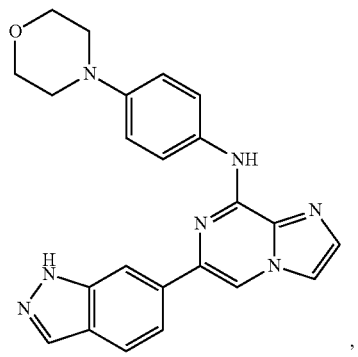

(I)

or a pharmaceutically acceptable salt thereof. This compound and its synthesis have been described in U.S. Pat. Nos. 8,450,321 and 8,455,493, which are hereby incorporated herein by reference in their entirety. U.S. Patent Application No. 20150038505A1 and U.S. Pat. No. 9,382,256 disclose several salt and polymorphic forms of the compound of Formula I, which are hereby incorporated herein by reference in their entirety. A method for preparing amorphous form, Form III (Form 3) and Form VII (Form 7) of a compound of Formula (I) are described in the published U.S. Patent Application Nos. 20160168155 (Fung, Peter Chee-Chu et. al.) and 20150038505 (Elford T. G. et. al.).

As pointed out in the '505 publication, in oral formulations using a mono-mesylate salt of the compound of Formula I, variations in pharmacodynamic responses were observed. Variations in the crystal structure of a pharmaceutical drug substance may affect the dissolution rate (which may affect bioavailability, etc.), manufacturability (e.g., ease of handling, ability to consistently prepare doses of known strength) and stability (e.g., thermal stability, shelf life, etc.) of a pharmaceutical drug product, particularly when formulated in a solid oral dosage form. As such, it is desirable to develop additional salt and polymorphic forms of the compound of Formula I that may offer differing dissolution, thermal stability and processability.

SUMMARY

Embodiments of the present application provide several polymorphic (crystalline) forms of the bis-mesylate salt of the compound of Formula I. The bis-mesylate salt may be depicted in various ways. The bis-mesylate salt can be depicted as the compound of Formula IA, having the molecular structure:

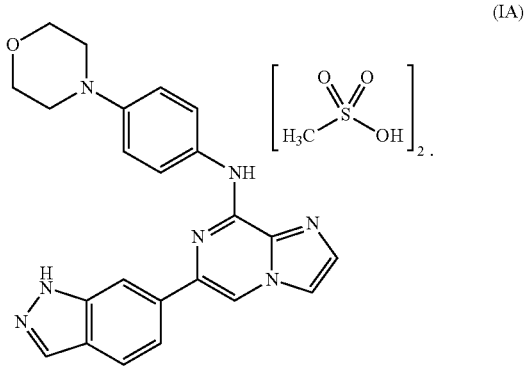

(IA)

It is to be understood that when the bis-mesylate salt of the compound of Formula I is depicted as Formula IA above, the ionic form (e.g., the cationic form of the compound of formula I and the anionic form of the methanesulfonic acid) is intended.

In some embodiments, polymorphic forms of the hydrate of the bis-mesylate salt of the compound of Formula I are provided by this disclosure. In certain embodiments, a polymorphic form of an unsolvated bis-mesylate salt of the compound of Formula I is provided by this disclosure. In one aspect, polymorphic Forms I, II, VI, XIII, XIV, XV, XVI, XVIII and XIX of the bis-mesylate salt of the compound of Formula IA are provided. Methods of making and using these polymorphic forms are also provided. Also provided are polymorphic products obtained by the processes described herein (e.g., obtained by the described methods of making). Pharmaceutical compositions comprising one or more polymorphic forms selected from Forms I, II, VI, XIII, XIV, XV, XVI, XVIII and XIX, and a pharmaceutically acceptable carrier are provided. Articles of manufacture and unit dosage forms comprising one or more polymorphic forms selected from Forms I, II, VI, XIII, XIV, XV, XVI, XVIII and XIX are provided.

Kits comprising one or more polymorphic forms selected from Forms I, II, VI, XIII, XIV, XV, XVI, XVIII and XIX, and instructions for use (e.g., instructions for use in SYK-mediated disorder, such as cancer or an autoimmune disease) are also provided. In some embodiments of the foregoing methods of making and using the polymorphic forms, polymorphic products, pharmaceutical compositions, articles of manufacture and unit dosage forms, and kits are provided herein.

Form I: A polymorphic form of the hydrate of bis-mesylate salt of the compound of Formula I. In some embodiments, a polymorph of a hydrate, bis-mesylate salt of a compound of Formula I is polymorph Form I, characterized by an X-ray diffraction pattern comprising sharp reflections at 6.6, 17.1, 21.3, and 22.2°2θ, ±0.2°2θ. It can be further characterized by peaks at 14.1, 14.8, 16.0, and 24.3°2θ, ±0.2°2θ. In some embodiments, polymorph Form I can be characterized by 2θ-reflections (±0.2 degrees) at 6.6, 14.1, 14.8, 16.0, 17.1, 21.3, 22.2, and 24.3°2θ, ±0.2°2θ. In some embodiments, a polymorph of a hydrate, bis-mesylate salt of a compound of Formula I is polymorph Form I, characterized by or having an X-ray diffraction pattern substantially as shown in FIG. 1A.

Form II: A polymorphic form of the hydrate of bis-mesylate salt of the compound of Formula I. In some embodiments, a polymorph of a hydrate, bis-mesylate salt of a compound of Formula I is polymorph Form II, characterized by or having an X-ray diffraction pattern comprising sharp reflections at 14.8, 17.4, 20.1, and 20.6°2θ, ±0.2°2θ. It can be further characterized by peaks at 5.9, 7.9, 13.6, and 26.5°2θ, ±0.2°2θ. In some embodiments, polymorph Form II can be characterized by 2θ-reflections (±0.2 degrees) at 5.9, 7.9, 13.6, 14.8, 17.4, 20.1, 20.6, and 26.5°. In some embodiments, a polymorph of a hydrate, bis-mesylate salt of a compound of Formula I is polymorph Form II, characterized by or having an X-ray diffraction pattern substantially as shown in FIG. 2A.

Form XIII: A polymorphic form of the hydrate of bis-mesylate salt of the compound of Formula I. In some embodiments, a polymorph of a hydrate, bis-mesylate salt of a compound of Formula I is polymorph Form XIII, characterized by X-ray diffraction pattern comprising sharp reflections at 11.6, 17.4, 19.5, and 21.8°2θ, ±0.2°2θ. It can be further characterized by peaks at 6.0, 15.4, 26.1 and 26.8°2θ, ±0.2°2θ. In some embodiments, polymorph Form XIII can be characterized by 2θ-reflections (±0.2 degrees) at 6.0, 11.6, 15.4, 17.4, 19.5, 21.8 and 26.8°. In some embodiments, a polymorph of a hydrate, bis-mesylate salt of a compound of Formula I is polymorph Form XIII, characterized by or having an X-ray diffraction pattern substantially as shown in FIG. 3A.

Form XIV: A polymorphic form of the bis-mesylate salt of the compound of Formula I. In some embodiments, a polymorph of a bis-mesylate salt of a compound of Formula I is polymorph Form XIV, characterized by sharp reflections at 15.0, 16.1, 22.9, and 26.4°2θ, ±0.2°2θ. It can be further characterized by peaks at 6.5, 18.7, 24.2, and 25.4°2θ, ±0.2°2θ. In some embodiments, polymorph Form XIV can be characterized by having an X-ray diffraction pattern comprising 2θ-reflections (±0.2 degrees) at 6.5, 15.0, 16.1, 18.7, 22.9, 24.2, 25.4, and 26.4°. In some embodiments, a polymorph of an unsolvated bis-mesylate salt of a compound of Formula I is polymorph Form XIV, characterized by or having an X-ray diffraction pattern substantially as shown in FIG. 4A.

Form XV: A polymorphic form of the hydrate of bis-mesylate salt of the compound of Formula I. In some embodiments, Form XV can be characterized by XRPD pattern having sharp reflections at 20.6, 22.0, 25.7, and 26.7°2θ, ±0.2°2θ. It can be further characterized by peaks at 7.0, 13.2, 15.3, and 19.6°2θ, ±0.2°2θ. In some embodiments, a polymorph of a hydrate, bis-mesylate salt of a compound of Formula I is polymorph Form XV, characterized by or having an X-ray diffraction pattern comprising 2θ-reflections (±0.2 degrees) at 7.0, 13.2, 15.3, 19.6, 20.6, 22.0, 25.7, and 26.7°. In some embodiments, a polymorph of a hydrate, bis-mesylate salt of a compound of Formula I is polymorph Form XV, characterized by or having an X-ray diffraction pattern substantially as shown in FIG. 5A.

Form XVI: A polymorphic form of the hydrate of bis-mesylate salt of the compound of Formula I. In some embodiments, a polymorph of a hydrate, bis-mesylate salt of a compound of Formula I is polymorph Form XVI, characterized by XRPD pattern with broad reflections at 7.8, 19.8, 22.2, and 26.0°2θ, ±0.2°2θ. It can be further characterized by peaks at 5.0, 14.8, 17.3 and 17.8°2θ, ±0.2°2θ. In some embodiments, Form XVI can be characterized by X-ray diffraction pattern comprising 2θ-reflections (±0.2 degrees) at 5.0, 7.8, 14.8, 17.3, 17.8, 19.8, 22.2, and 26.0°. In some embodiments, a polymorph of a hydrate, bis-mesylate salt of a compound of Formula I is polymorph Form XVI, characterized by or having an X-ray diffraction pattern substantially as shown in FIG. 6A.

Form XVIII: A polymorphic form of the hydrate of bis-mesylate salt of the compound of Formula I. In some embodiments, a polymorph of a hydrate, bis-mesylate salt of a compound of Formula I is polymorph Form XVIII, characterized by or having an X-ray diffraction pattern comprising 2θ-reflections (±0.2 degrees) at 4.5, 8.9, 22.1 and 31.6°. It can be further characterized by peaks at 13.3, 18.0, 24.7, and 27.2°2θ, ±0.2°2θ. In some embodiments, a polymorph of a hydrate, bis-mesylate salt of a compound of Formula I is polymorph Form XVIII, characterized by or having an X-ray diffraction pattern substantially as shown in FIG. 7A.

Form VI: A polymorphic form of the formic acid solvate of bis-mesylate salt of the compound of Formula I. In some embodiments, a polymorph of a formic acid solvate of bis-mesylate salt of a compound of Formula I is polymorph Form VI, characterized by or having an X-ray diffraction pattern comprising sharp reflections at 13.9, 16.6, 20.5, and 25.2°2θ, ±0.2°2θ. It can be further characterized by peaks at 6.3, 14.6, 17.8, and 21.2°2θ, ±0.2°2θ. In some embodiments, a polymorph of a formic acid solvate of bis-mesylate salt of a compound of Formula I is polymorph Form VI, characterized by or having an X-ray diffraction pattern substantially as shown in FIG. 8A.

Form XIX: A polymorphic form of the hydrate of bis-mesylate salt of the compound of Formula I. In some embodiments, a polymorph of a hydrate, bis-mesylate salt of a compound of Formula I is polymorph Form XIX, characterized by or having an X-ray diffraction pattern comprising two broad reflections 2θ-reflections (±0.2 degrees) at 6.3 and 26.3°. In some embodiments, a polymorph of a hydrate, bis-mesylate salt of a compound of Formula I is polymorph Form XIX, characterized by or having an X-ray diffraction pattern substantially as shown in FIG. 9A.

In another aspect, provided is a pharmaceutical composition comprising a polymorph according to any of the foregoing embodiments. In yet another aspect, provided is an article of manufacture comprising a polymorph or a pharmaceutical composition according to any of the foregoing.

In one aspect, provided is a method of treating a condition in a subject in need thereof, comprising administering to the subject a polymorph of a compound of Formula I, or a solvate or hydrate thereof selected from Form I, II, VI, XIII, XIV, XV, XVI, XVIII and XIX; or a pharmaceutical composition comprising any of the foregoing embodiments, wherein the condition is selected from the group consisting of cancer and autoimmune disease. In some embodiments, the condition is selected from the group consisting of acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), mantle cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), and marginal zone lymphoma (MZL). In certain embodiments, the condition is non-Hodgkin's lymphoma. In one variation, the NHL is indolent non-Hodgkin's lymphoma (iNHL). In another variation, the iNHL is refractory iNHL. In yet another variation, the iNHL is non-FL iNHL.

In other embodiments, the condition is selected from the group consisting of asthma, rheumatoid arthritis, multiple sclerosis, and lupus. In some of the foregoing embodiments, the subject is a mammal. In some of the foregoing embodiments, the subject is human.

DETAILED DESCRIPTION

Figure 1A:
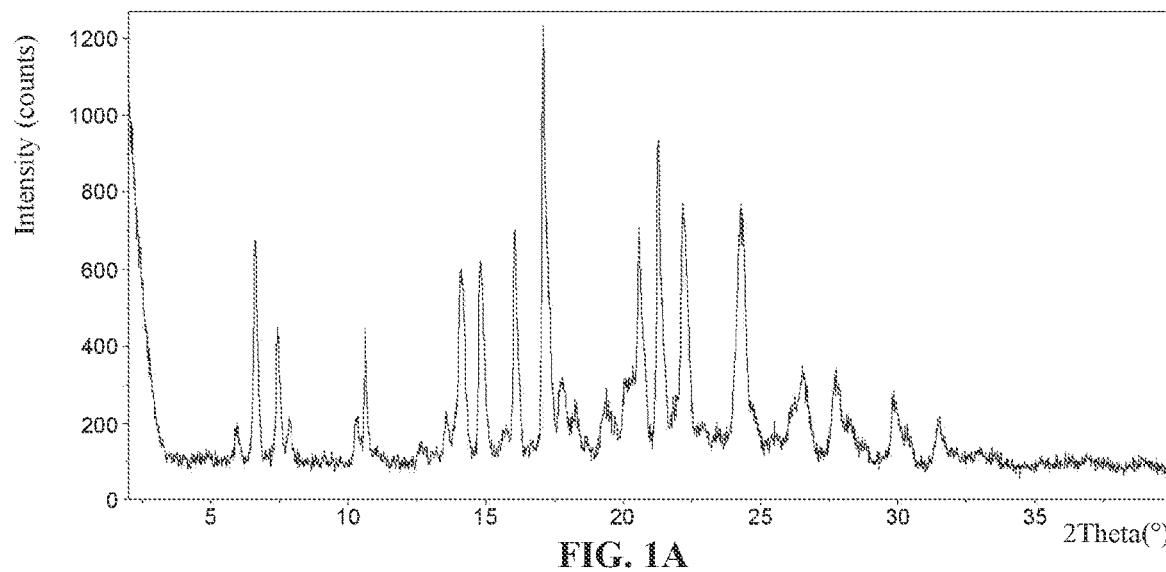
FIG. 1A is an exemplary X-ray powder diffraction pattern (XRPD) pattern of polymorph Form I.

The following examples are included to illustrate embodiments of the disclosure, and are not intended to limit the scope of the disclosure. It should be appreciated by those of skill in the art that the techniques disclosed herein represent techniques that apply in the practice of the disclosure. Those of skill in the art would appreciate that, in light of the present disclosure, changes can be made in the examples herein without departing from the spirit and scope of the disclosure.

As used in the present specification, the following words and phrases are generally intended to have the meanings as set forth below, except to the extent that the context in which they are used indicates otherwise.

Terms used in the singular will also include the plural. For example, "a" means one or more unless indicated otherwise.

The use of the term "about" includes and describes the value or parameter per se. For example, "about x" includes and describes "x" per se. In some embodiments, the term "about" when used in association with a measurement, or used to modify a value, a unit, a constant, or a range of values, refers to variations of ±10%. For example, "about 2:8" in some embodiments includes 1.8-2.2:7.2-8.8.

The use of the term "adding" does not limit the order, method or how the materials being added are combined, unless indicated otherwise. For instance, "adding A to B" may also describe "adding B to A". Furthermore, "adding A and B to C" may also describe the various other combinations such as "adding A to B and C", "adding A and C to B", "adding B to A and C", "adding B and C to A", and "adding C to A and B".

Provided are pharmaceutically acceptable salts of the compound of Formula I:

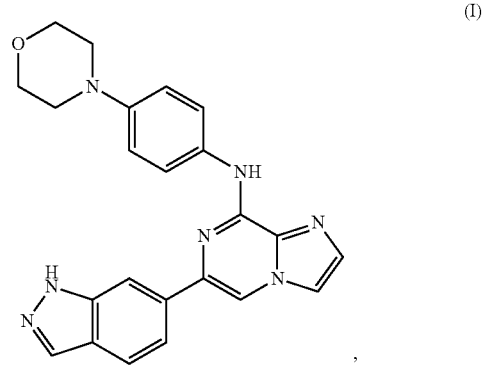 [SMILES: c1cn2cc(-c3ccc4cn[nH]c4c3)nc(Nc3ccc(N4CCOCC4)cc3)c2n1]

(I)

or a hydrate thereof. In some aspects, the pharmaceutically acceptable salt of the compound of Formula I is a polymorph of bis-mesylate salt, or a solvate/hydrate thereof, selected from polymorph Form I, II, VI, XIII, XIV, XV, XVI, XVIII and XIX. In one variation, the pharmaceutically acceptable salt of the compound of Formula I is an unsolvated bis-mesylate salt having polymorph Form XIV.

In some embodiments, a polymorphic form of bis-mesylate salt, or a hydrate/solvate thereof, of a compound of Formula I is provided. It should be understood that "bis-mesylate salt" may also be referred to herein as "bis-MSA salt".

The bis-mesylate salt of a compound of Formula I may be depicted herein in various ways. For example, in one variation, a bis-mesylate salt may be represented by Formula IA and in another by formula IB:

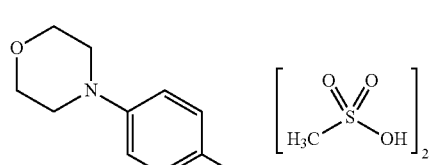

(IA)

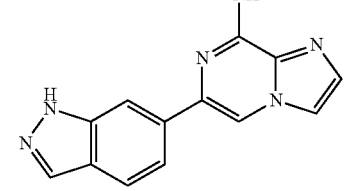

(IB)

In some embodiments, the bis-mesylate salt, as depicted by Formula IA or IB, may be a hydrate thereof. For example, in one embodiment, the bis-mesylate salt, as depicted by Formula IA or IB, may be a hydrate, bis-mesylate salt. Without wishing to be bound by any theory, a hydrate, bis-mesylate salt of a compound of Formula I may also be represented by Formula IC:

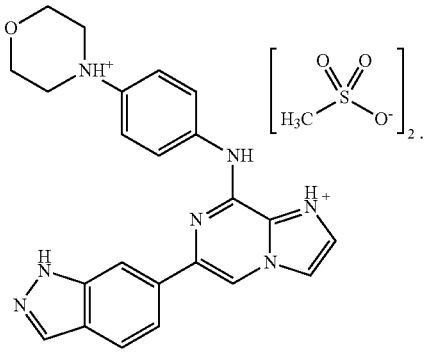

(IC)

Without wishing to be bound by any theory, in other embodiments, a hydrate of a bis-mesylate salt of a compound of Formula I may be represented by Formula ID:

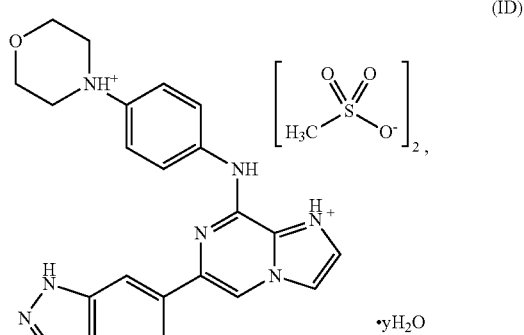

(ID)

wherein y is at least 0.5. In some variations, y is at least 1, at least 1.5, at least 2, at least 2.5, at least 3, or at least 4, or between 0.5 and 5, between 0.5 and 4, between 0.5 and 2, between 0.5 and 1.5, or about 0.5, about 1, about 1.5, about 2, about 3, or about 4 or about 5, or about 6, or about 7 or about 7 or about 8. In certain variations, y is an integer. For example, when y is 1, the compound of Formula ID is a monohydrate, bis-mesylate salt. When y is 2, the compound of Formula ID is a dihydrate, bis-mesylate salt. In certain embodiments, the polymorph is a sesquihydrate where the polymorph contains three molecules of water of crystallization per two molecules of a compound of Formula I. Thus, variable "y" in Formula ID represents the variability of the water content in the hydrate of the bis-mesylate salt.

Without wishing to be bound by any theory, in another variation, the hydrate, bis-mesylate salt may be represented by Formula IE:

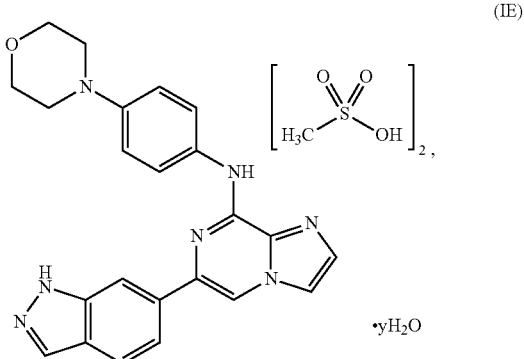

(IE)

wherein y is at least 0.5. In some variations, y is at least 1, at least 1.5, at least 2, at least 2.5, at least 3, or at least 4, or between 0.5 and 5, between 0.5 and 4, between 0.5 and 2, between 0.5 and 1.5, or about 0.5, about 1, about 1.5, about 2, about 3, or about 4, or about 5 or about 6 or about 7 or about 8. In certain variations, y is an integer. For example, when y is 2, the compound of Formula IE is a dihydrate, bis-mesylate salt. In other variations, y is a non-integer.

In yet other embodiments, a hydrate of a bis-mesylate salt of a compound of Formula I may have varying amounts of water.

Provided herein are polymorphs of a bis-mesylate salt of a compound of Formula I, or a hydrate thereof. The polymorphs described herein may be characterized by a variety of solid state analytical data, including for example, by X-ray powder diffraction pattern (XRPD), differential scanning calorimetry (DSC) and thermal gravimetric analysis (TGA).

Figure 1B:
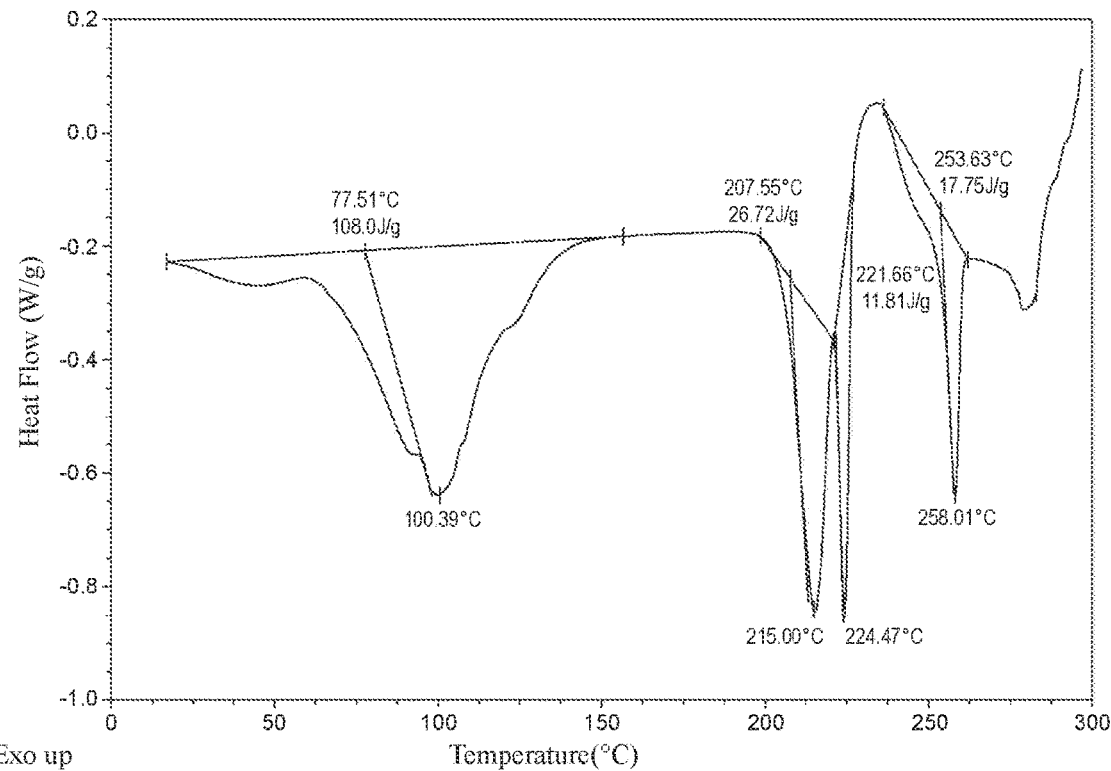
FIG. 1B is an exemplary differential scanning calorimetry (DSC) plot of polymorph Form I.
Figure 1C:
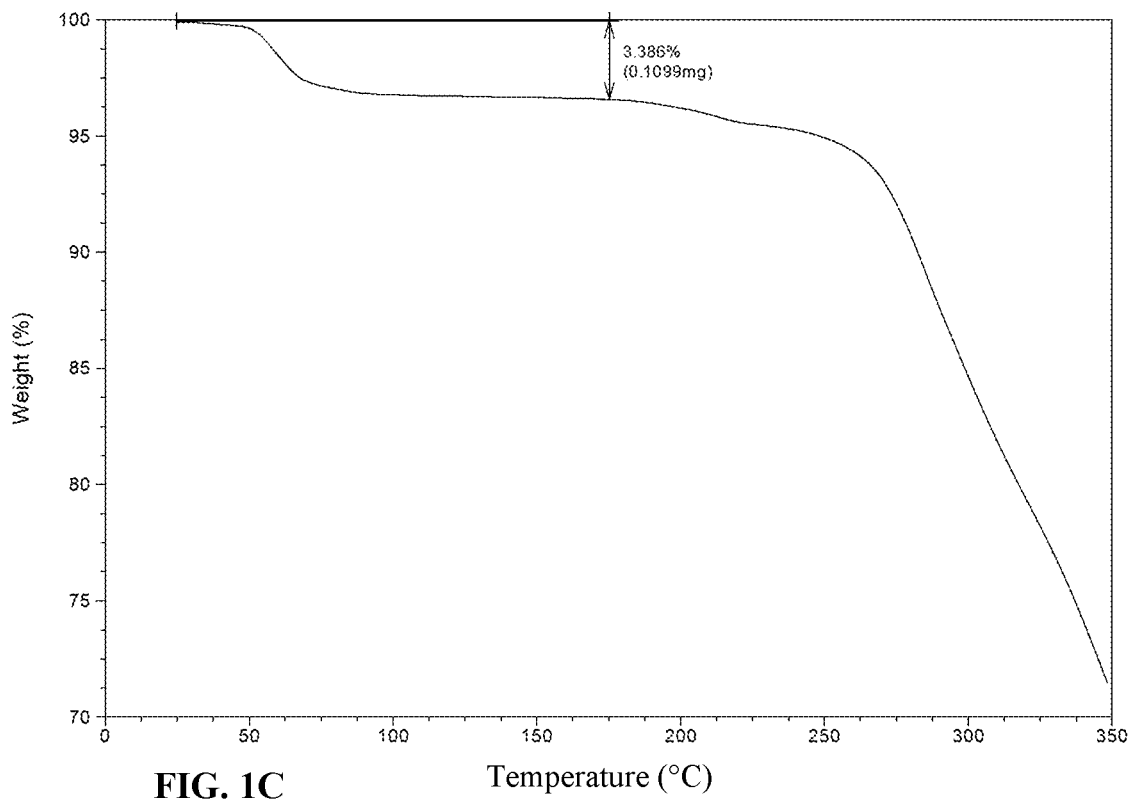
FIG. 1C is an exemplary thermal gravimetric analysis (TGA) plot of polymorph Form I.
Figure 1D:
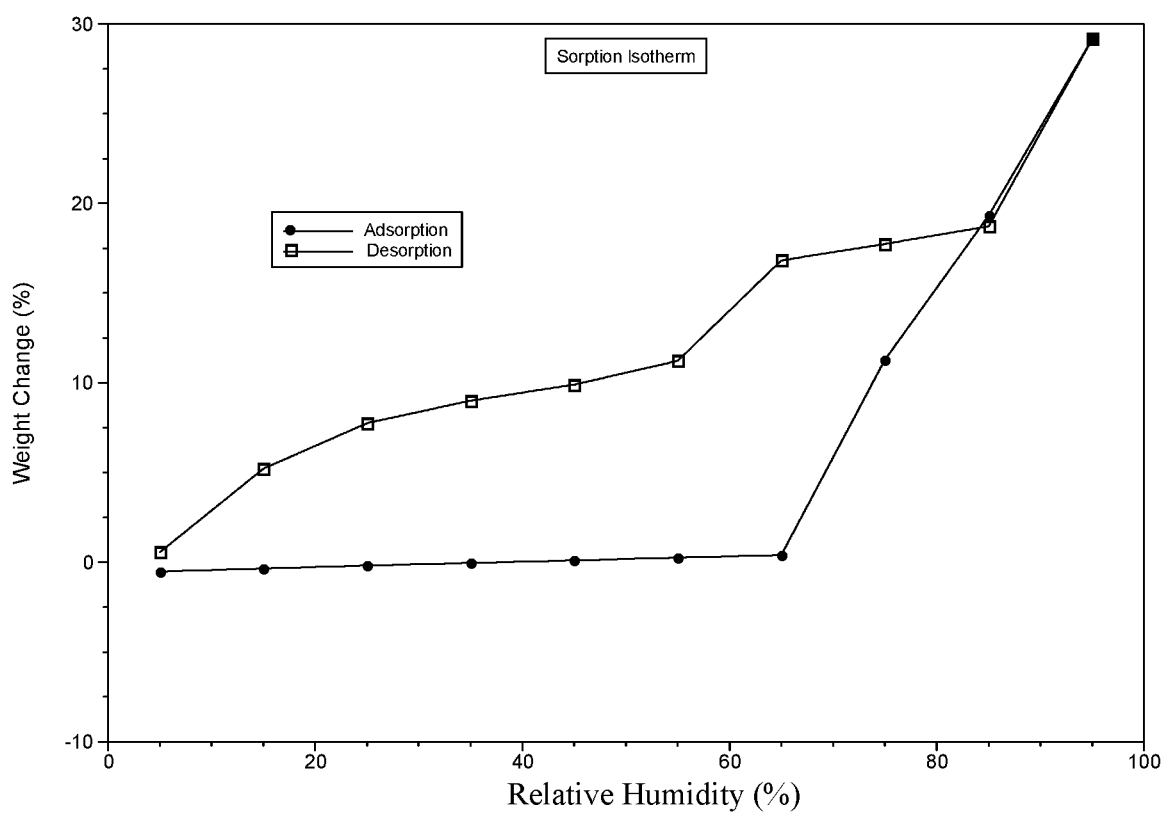
FIG. 1D shows the dynamic vapor sorption (DVS) plot of Form I.

Form I: A polymorphic form of the hydrate of bis-mesylate salt of the compound of Formula I. In some embodiments, a polymorph of a hydrate, bis-mesylate salt of a compound of Formula I is polymorph Form I, characterized by or having an X-ray diffraction pattern comprising 2θ-reflections (±0.2 degrees) at 6.6, 14.1, 14.8, 16.0, 17.1, 21.3, 22.2, and 24.3°. In some embodiments, a polymorph of a hydrate, bis-mesylate salt of a compound of Formula I is polymorph Form I, characterized by or having an X-ray diffraction pattern substantially as shown in FIG. 1A. The DSC curve for polymorphy Form I for the compound of formula I is shown in FIG. 1B and indicates multiple endothermic transitions at 78, 208, 222, and 254° C. The TGA curve is shown in FIG. 1C and displays a weight loss (3.3% from room temperature to 175° C.) indicating a solvate that was identified as water based on KF (3.12%). The dynamic vapor sorption curve for Form I is shown in FIG. 1D and the data indicates that the form absorbs about 30 wt. % of water up to 95% RH at 25° C. Form I (hydrate) was isolated by heating form VI at 150° C. for two hours followed by cooling to room temperature or by heating form III at 175° C. followed by cooling to room temperature.

Figure 2A:
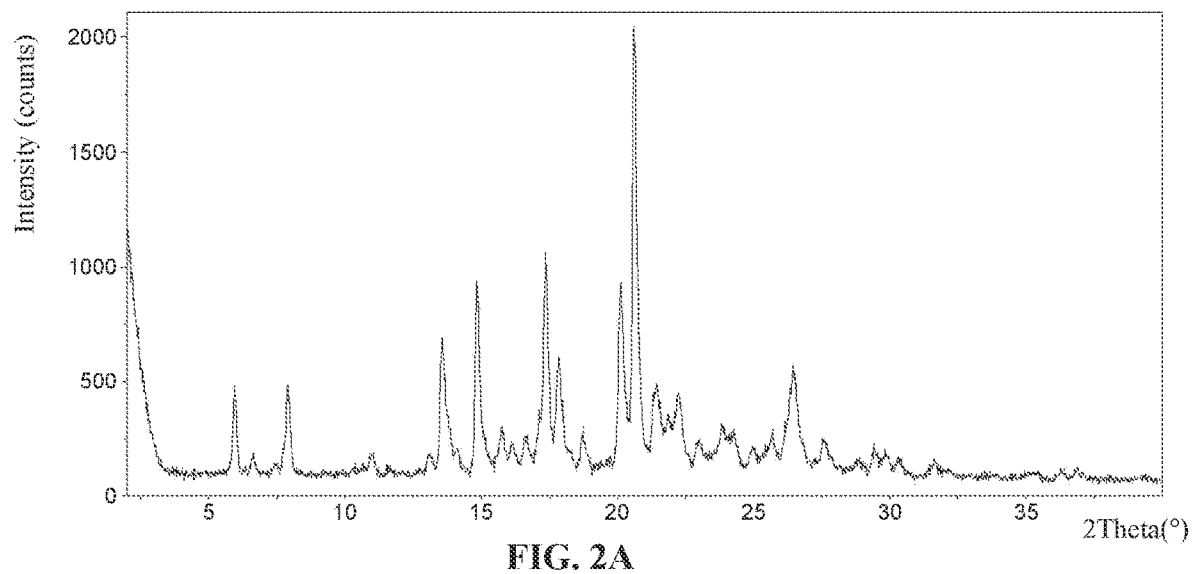
FIG. 2A is an exemplary XRPD pattern of polymorph Form II.
Figure 2B:
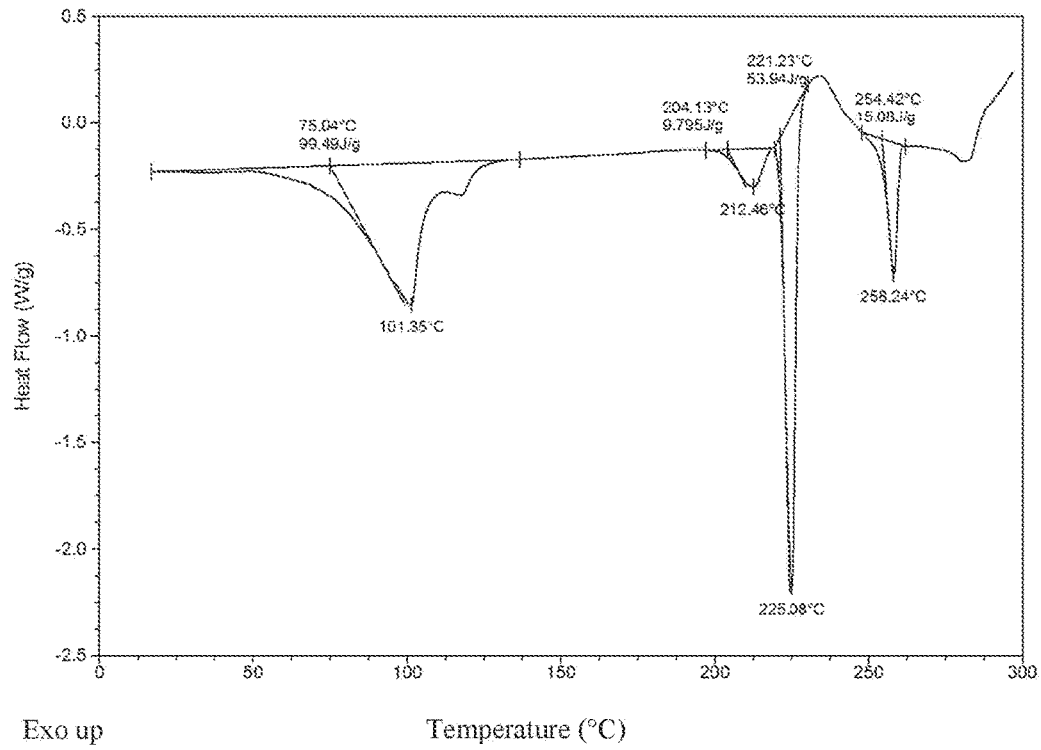
FIG. 2B is an exemplary DSC plot of polymorph Form II.
Figure 2C:
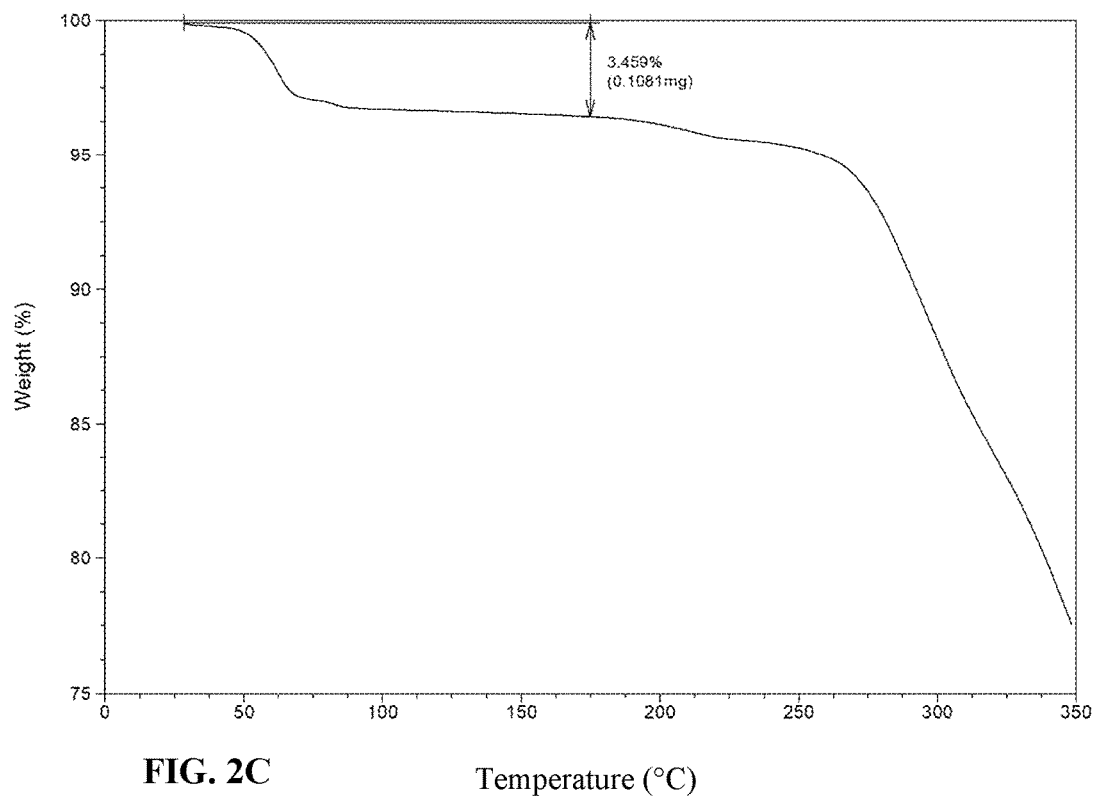
FIG. 2C is an exemplary TGA plot of polymorph Form II.
Figure 2D:
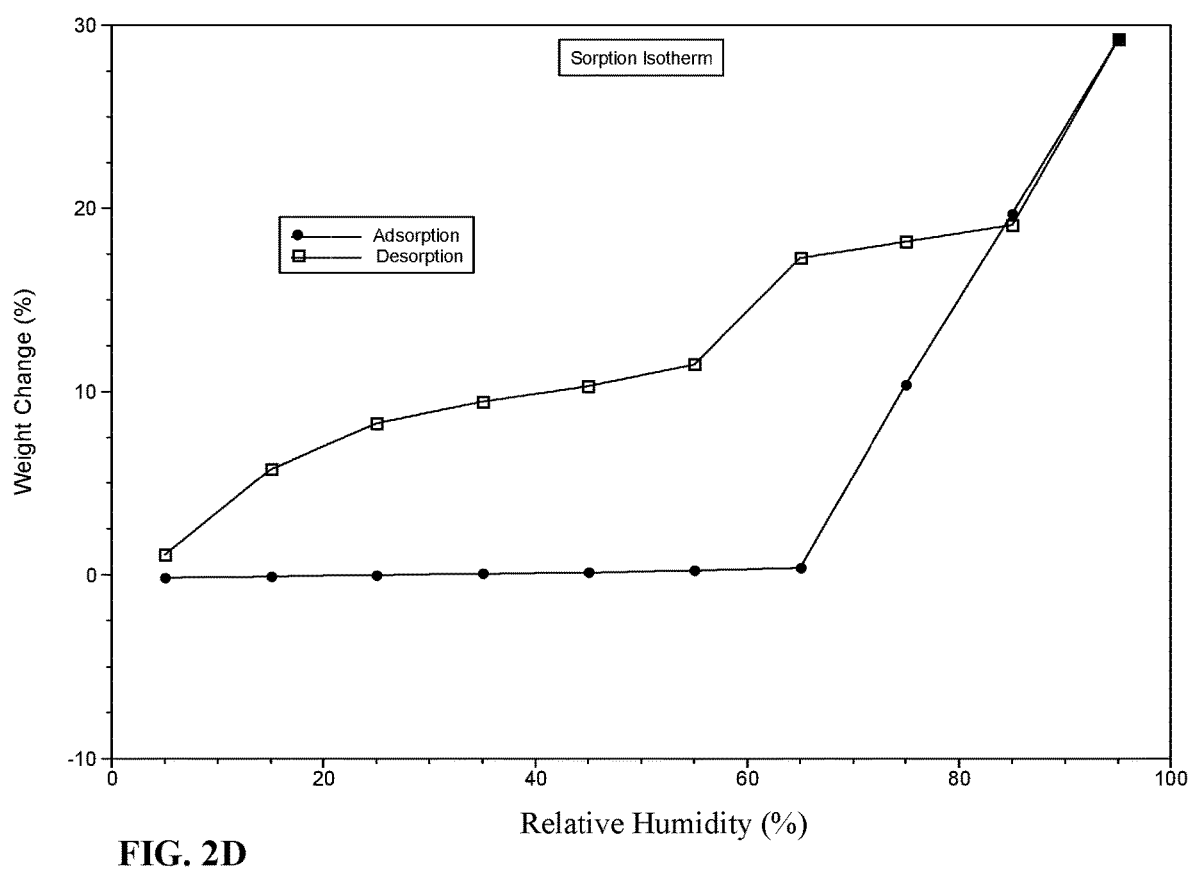
FIG. 2D shows the DVS plot of polymorph Form II.

Form II: A polymorphic form of the hydrate of bis-mesylate salt of the compound of Formula I. In some embodiments, a polymorph of a hydrate, bis-mesylate salt of a compound of Formula I is polymorph Form II, characterized by or having an X-ray diffraction pattern comprising 2θ-reflections (±0.2 degrees) at 5.9, 7.9, 13.6, 14.8, 17.4, 20.1, 20.6, and 26.5°. In some embodiments, a polymorph of a hydrate, bis-mesylate salt of a compound of Formula I is polymorph Form II, characterized by or having an X-ray diffraction pattern substantially as shown in FIG. 2A. The DSC curve is shown in FIG. 2B and indicates multiple endothermic transitions at 75, 204, 221, and 254° C. The TGA curve is shown in FIG. 2C and displays a weight loss (3.5% from room temperature to 175° C.) indicating a solvate that was identified as water based on KF (3.08%). The dynamic vapor sorption curve for Form II is shown in FIG. 2D and the data indicates that the form absorbs about 30 wt. % of water up to 95% RH at 25° C. XRPD analysis of the sample after the DVS experiment shows that the material had converted to Form VII. Form II (hydrate) was isolated by heating Form VI under vacuum at 120° C. overnight. Form II hydrate was also isolated by slurring Form VI in isopropyl alcohol at room temperature for about one week.

Figure 3A:
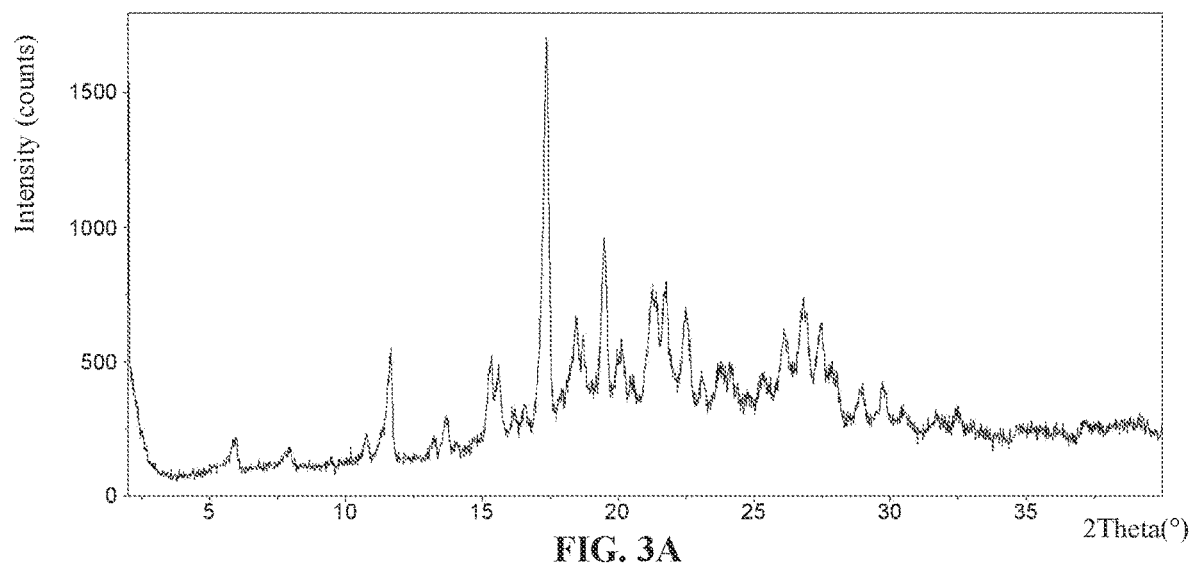
FIG. 3A is an exemplary XRPD pattern of polymorph Form XIII.
Figure 3B:
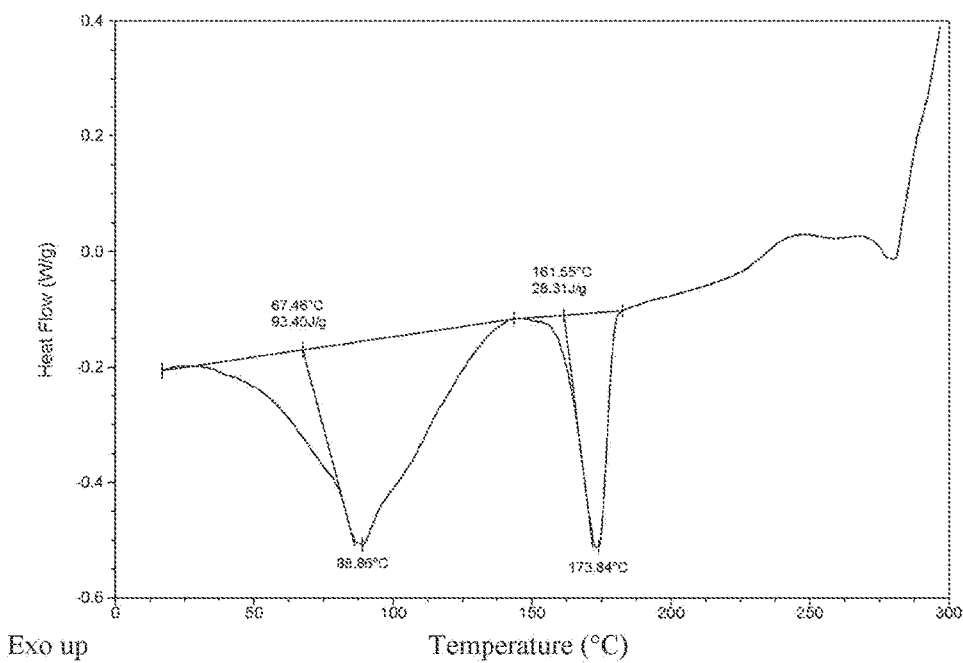
FIG. 3B is an exemplary DSC plot of polymorph Form XIII.
Figure 3C:
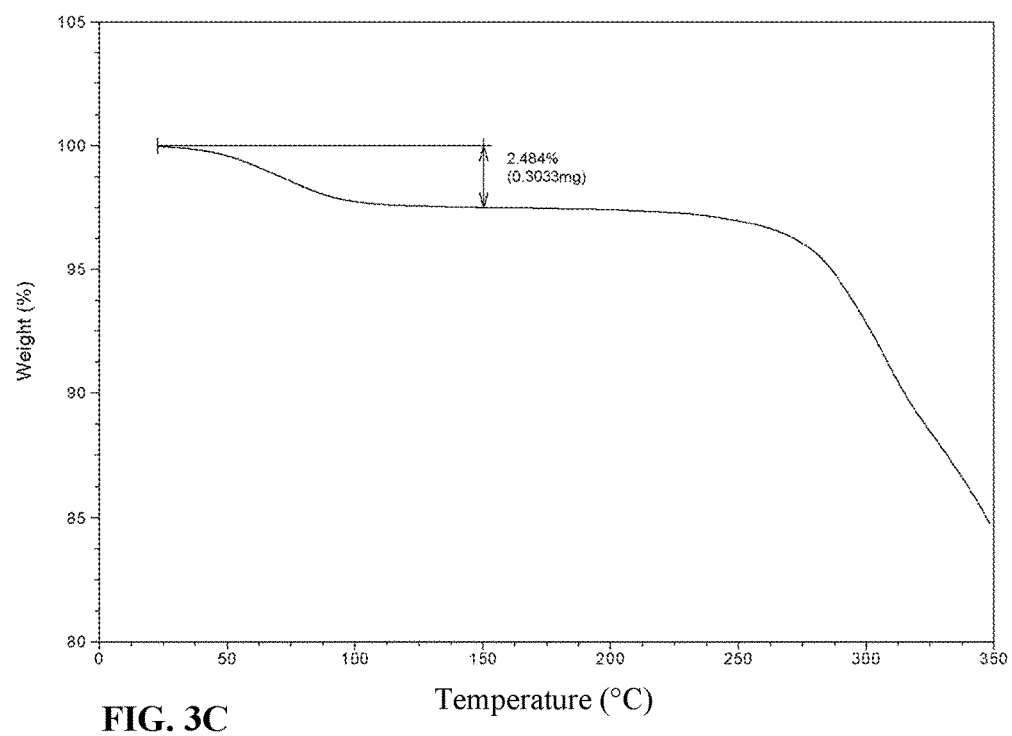
FIG. 3C is an exemplary TGA plot of polymorph Form XIII
Figure 3D:
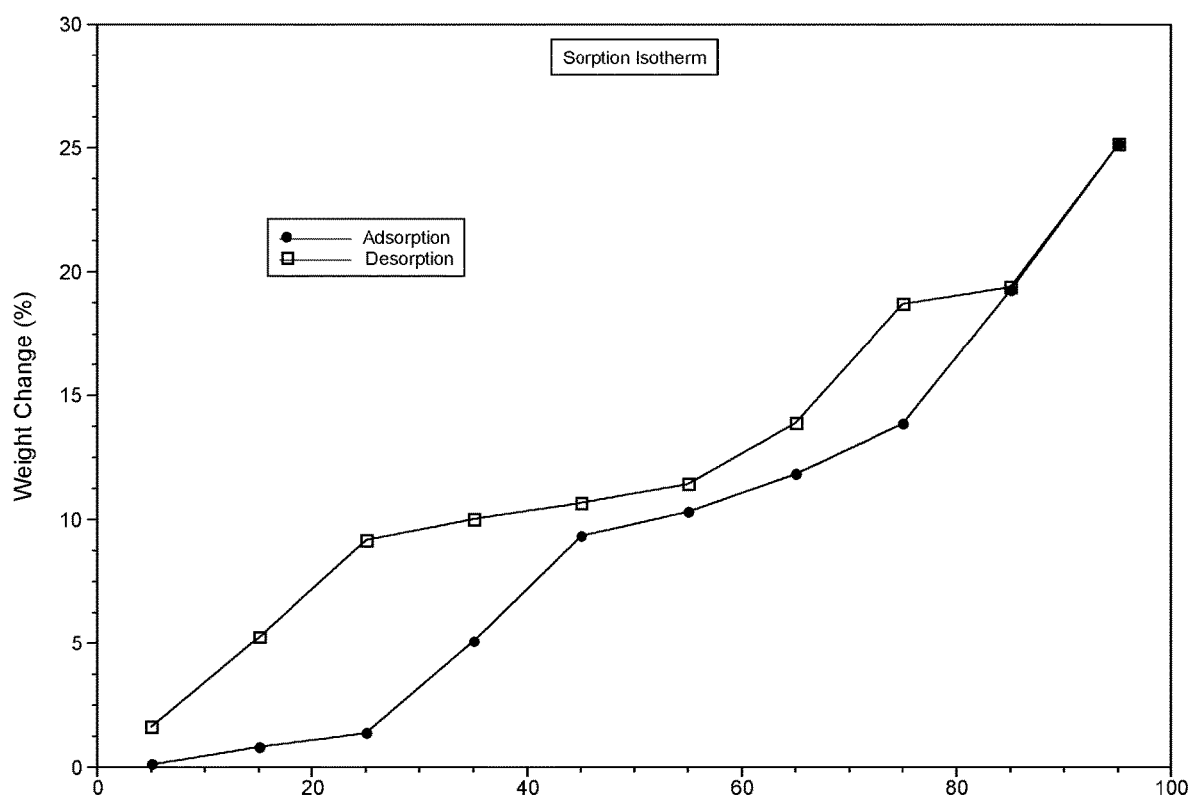
FIG. 3D shows the DVS plot of polymorph Form XIII.

Form XIII: A polymorphic form of the hydrate of bis-mesylate salt of the compound of Formula I. In some embodiments, a polymorph of a hydrate, bis-mesylate salt of a compound of Formula I is polymorph Form XIII, characterized by or having an X-ray diffraction pattern comprising 2θ-reflections (±0.2 degrees) at 6.0, 11.6, 15.4, 17.4, 19.5, 21.8, and 26.8°. In some embodiments, a polymorph of a hydrate, bis-mesylate salt of a compound of Formula I is polymorph Form XIII, characterized by or having an X-ray diffraction pattern substantially as shown in FIG. 3A. The DSC curve is shown in FIG. 3B and indicates multiple endothermic transitions at 67 and 162° C. The TGA curve is shown in FIG. 3C and displays a weight loss (2.5% from room temperature to 150° C.) indicating a solvate that is presumably water (Form XIII is unstable at ambient conditions and sample partially converted to Form VII before KF could be run). The dynamic vapor sorption curve for Form XIII is shown in FIG. 3D and the data indicates that the form absorbs ~25 wt. % of water up to 95% RH at 25° C. XRPD analysis of the sample after the DVS experiment shows that the material had converted to Form VII. Form XIII (hydrate) was isolated by exposing Form VII to about 0% relative humidity in a $P_2O_5$ chamber heated to 40° C. under vacuum. A method for preparing Form VII (Form 7) is described in U.S. Patent publication Nos. 2016/0168155 (Fung, Peter Chee-Chu et. al.) and 2015/0038505 (Elford T. G. et. al.).

Figure 4A:
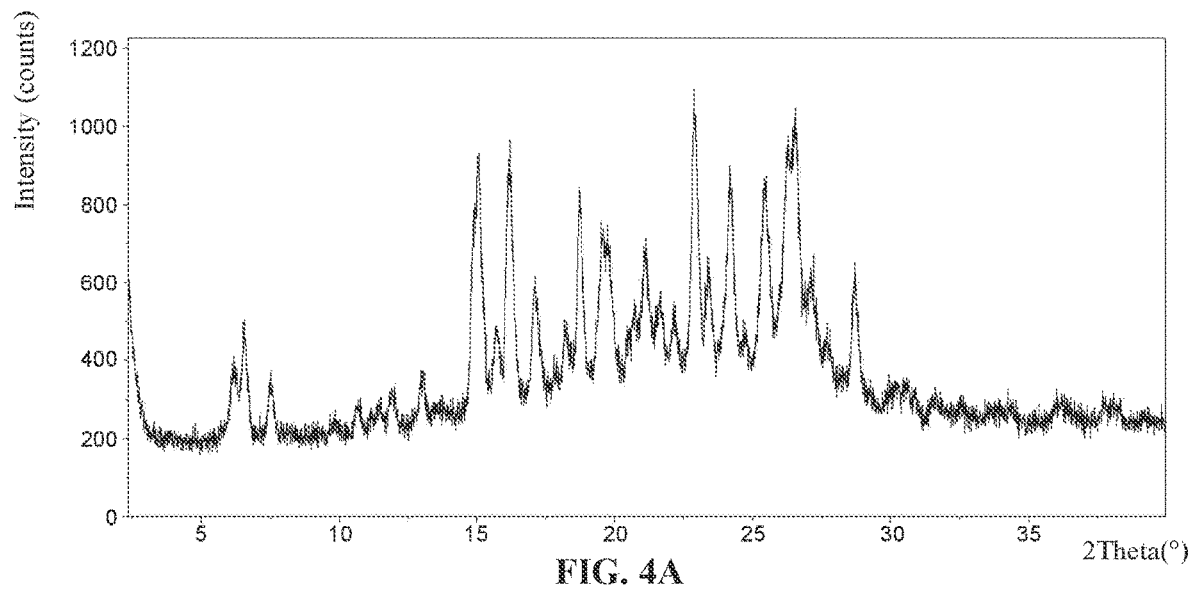
FIG. 4A is an exemplary XRPD pattern of polymorph Form XIV.
Figure 4B:
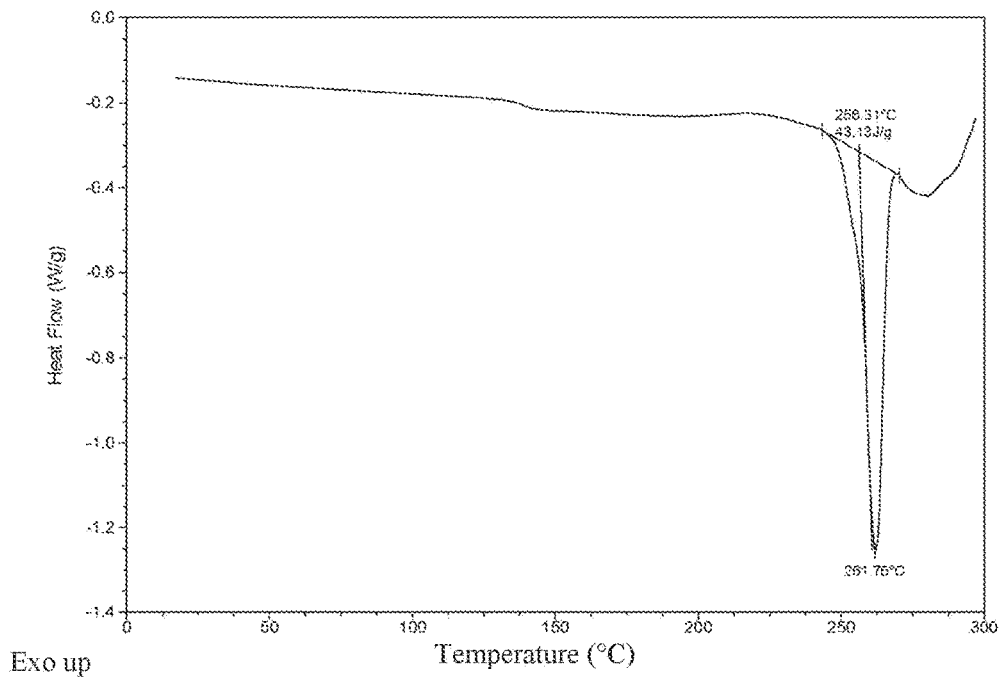
FIG. 4B is an exemplary DSC plot of polymorph Form XIV.
Figure 4C:
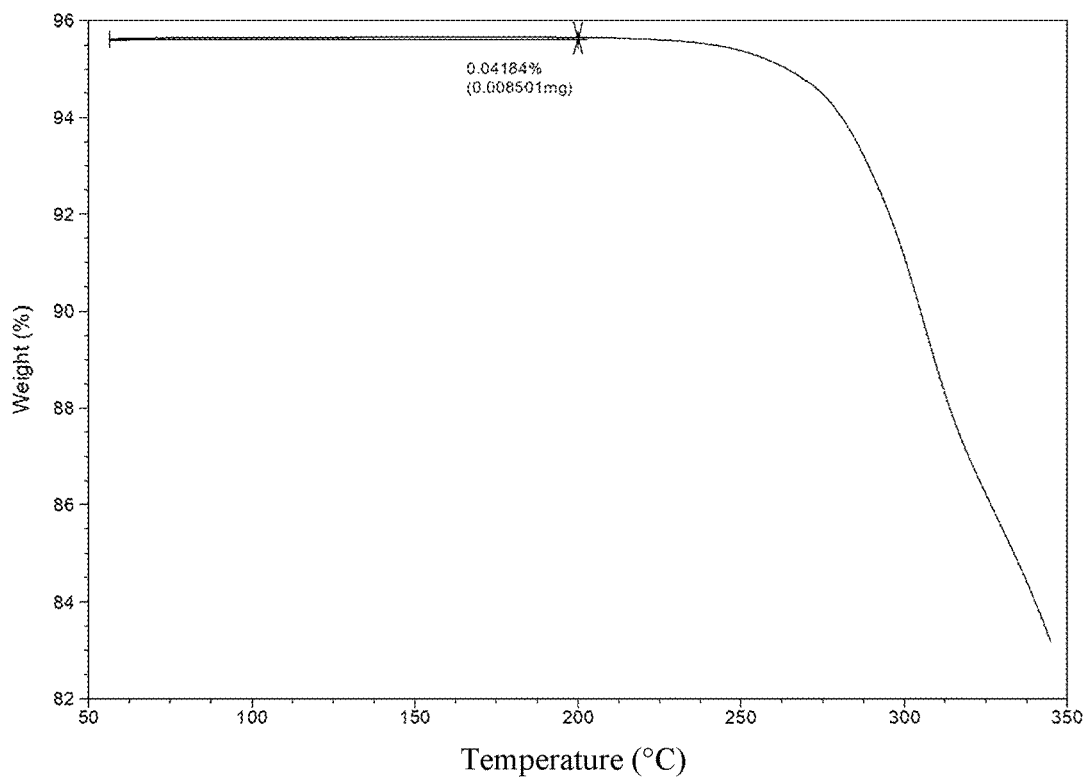
FIG. 4C is an exemplary TGA plot of polymorph Form XIV.
Figure 4D:
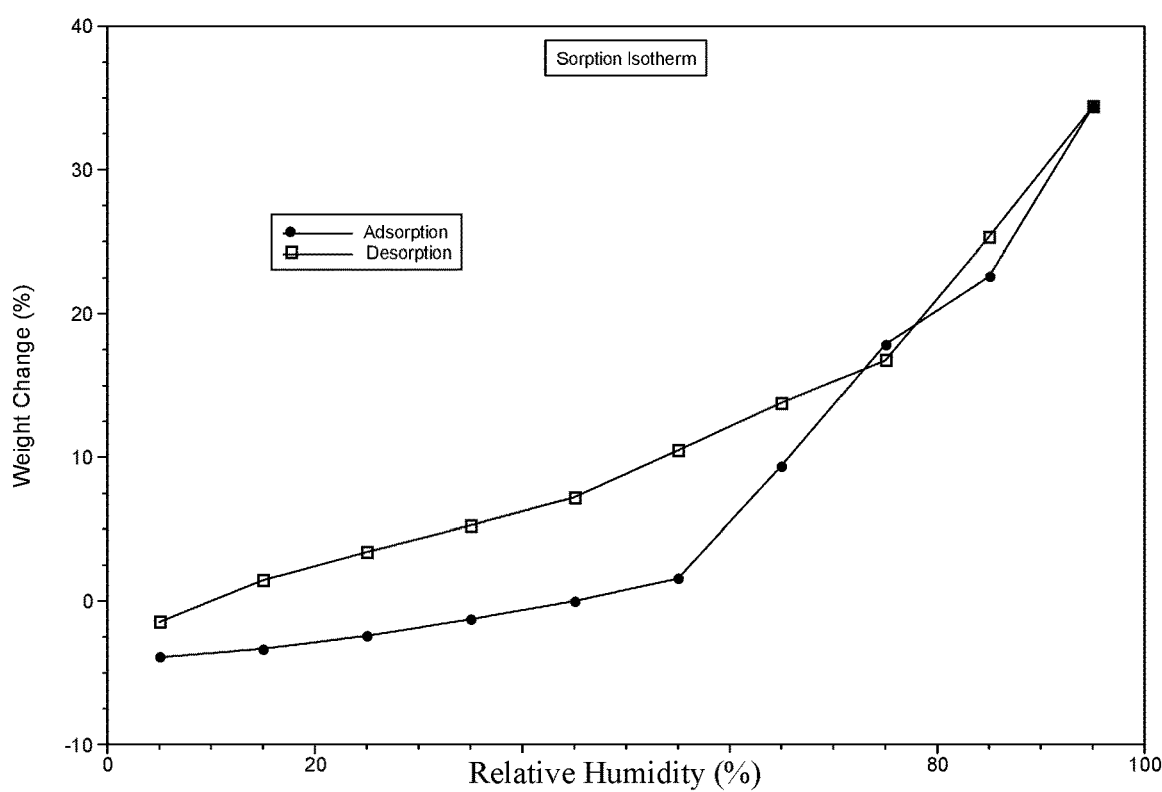
FIG. 4D shows the DVS plot of polymorph Form XIV.

Form XIV: A polymorphic form of the unsolvated bis-mesylate salt of the compound of Formula I. In some embodiments, a polymorph of a bis-mesylate salt of a compound of Formula I is polymorph Form XIV, characterized by or having an X-ray diffraction pattern comprising 2θ-reflections (±0.2 degrees) at 6.5, 15.0, 16.1, 18.7, 22.9, 24.2, 25.4, and 26.4°. In some embodiments, a polymorph of an unsolvated bis-mesylate salt of a compound of Formula I is polymorph Form XIV, characterized by or having an X-ray diffraction pattern substantially as shown in FIG. 4A. The DSC curve is shown in FIG. 4B and indicates an endotherm at 256° C. The TGA curve is shown in FIG. 4C and displays no appreciable weight loss indicating an unsolvated material. The dynamic vapor sorption curve for Form XIV is shown in FIG. 4D and the data indicates that the form absorbs about 35 wt. % of water up to 95% RH at 25° C. XRPD analysis of the sample after the DVS experiment shows that the material had converted to Form VII. Form XIV (unsolvated) was isolated by heating Form I, Form II, Form III, or Form XVI to about 250° C. on a DSC. A method for preparing Form III (Form 3) is described in published U.S. Patent Application Nos. 2016/0168155 (Fung, Peter Chee-Chu et. al.) and 2015/0038505 (Elford T. G. et. al.).

Figure 5A:
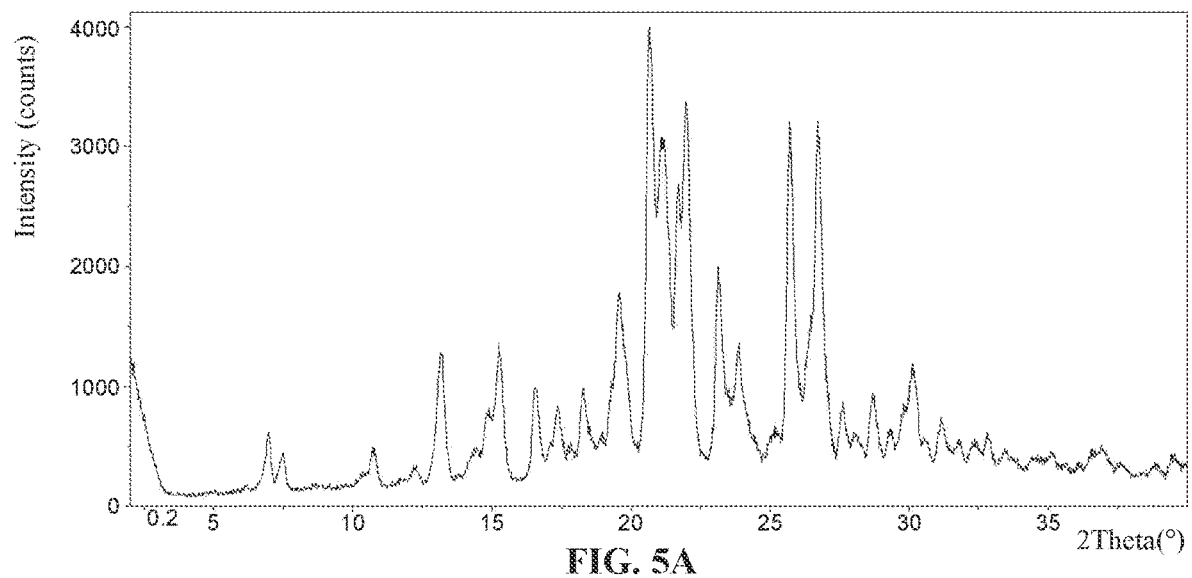
FIG. 5A is an exemplary XRPD pattern of polymorph Form XV.
Figure 5B:
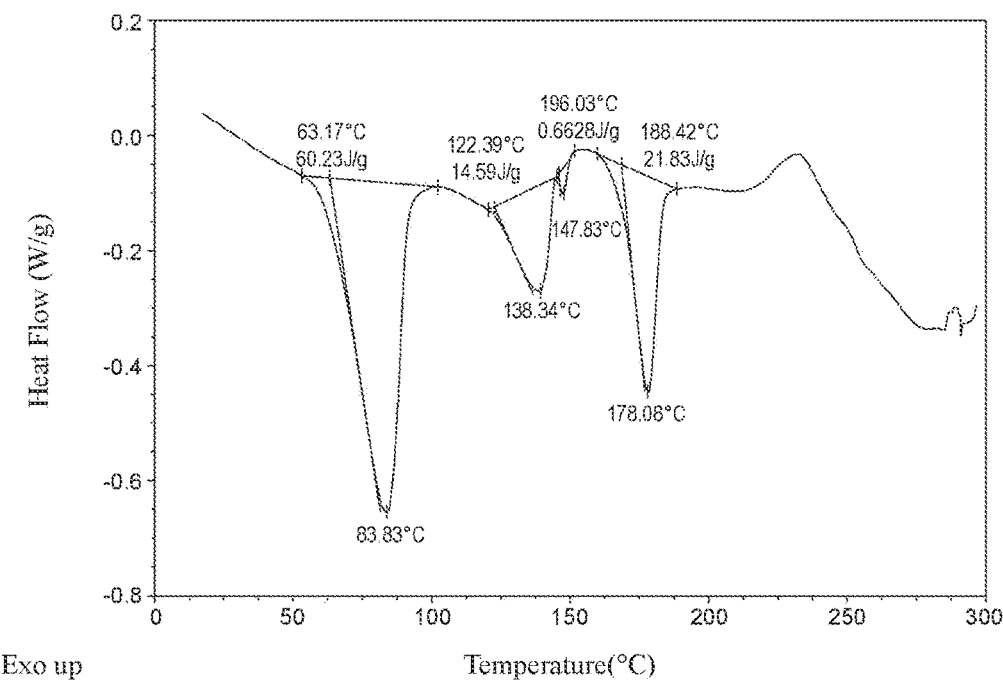
FIG. 5B is an exemplary DSC plot of polymorph Form XV.
Figure 5C:
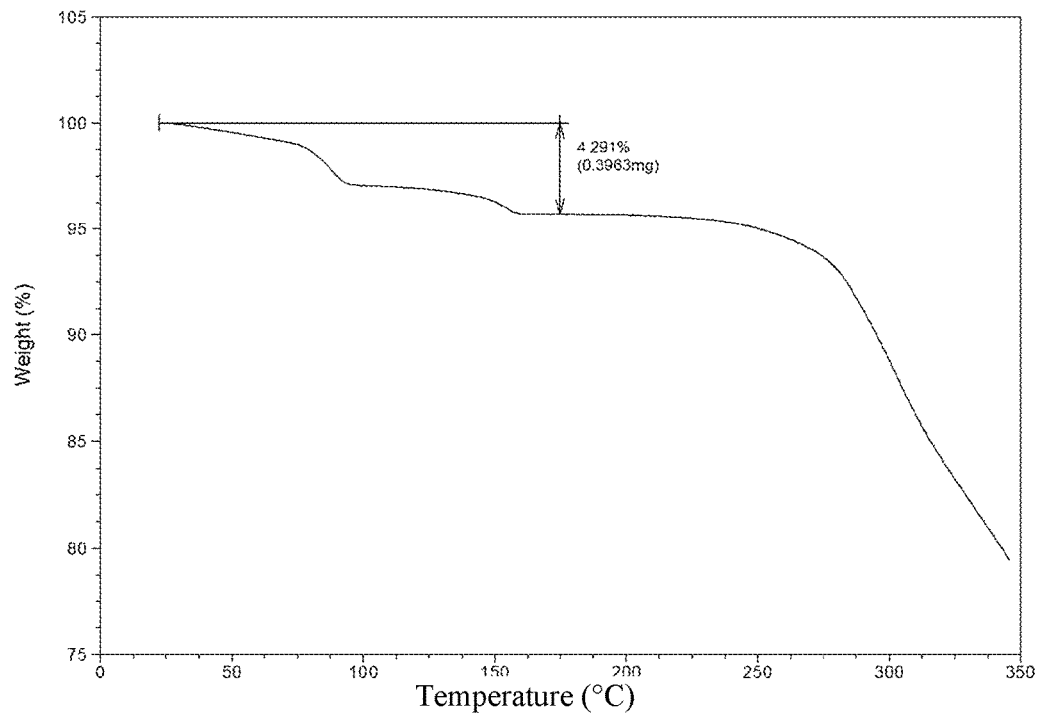
FIG. 5C is an exemplary TGA plot of polymorph Form XV.
Figure 5D:
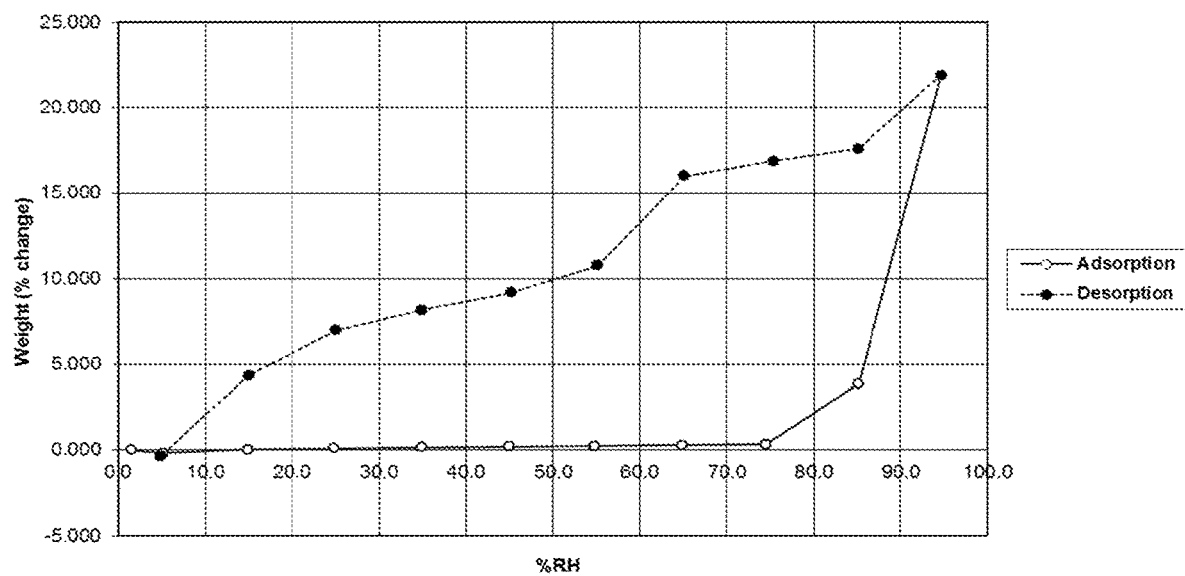
FIG. 5D shows the DVS plot of polymorph Form XV.

Form XV. A polymorphic form of the hydrate of bis-mesylate salt of the compound of Formula I. In some embodiments, a polymorph of a hydrate, bis-mesylate salt of a compound of Formula I is polymorph Form XV, characterized by or having an X-ray diffraction pattern comprising 2θ-reflections (±0.2 degrees) at 7.0, 13.2, 15.3, 19.6, 20.6, 22.0, 25.7, and 26.7°. In some embodiments, a polymorph of a hydrate, bis-mesylate salt of a compound of Formula I is polymorph Form XV, characterized by or having an X-ray diffraction pattern substantially as shown in FIG. 5A. The DSC curve is shown in FIG. 5B and indicates multiple endothermic transitions at 63, 122, 146 and 168° C. The TGA curve is shown in FIG. 5C and displays a weight loss (4.3% from room temperature to 175° C.) indicating a solvate that was identified as water based on KF (4.2%). Weight loss above 225° C. is attributed to decomposition. The dynamic vapor sorption curve for Form XV is shown in FIG. 5D and the data indicates that the form absorbs ~23 wt. % of water up to 95% RH at 25° C. XRPD analysis of the sample after the DVS experiment shows that the material had converted to Form VII. Form XI (hydrate) was isolated by slurring Form VII in 4% water in acetone at room temperature for several days.

Figure 6A:
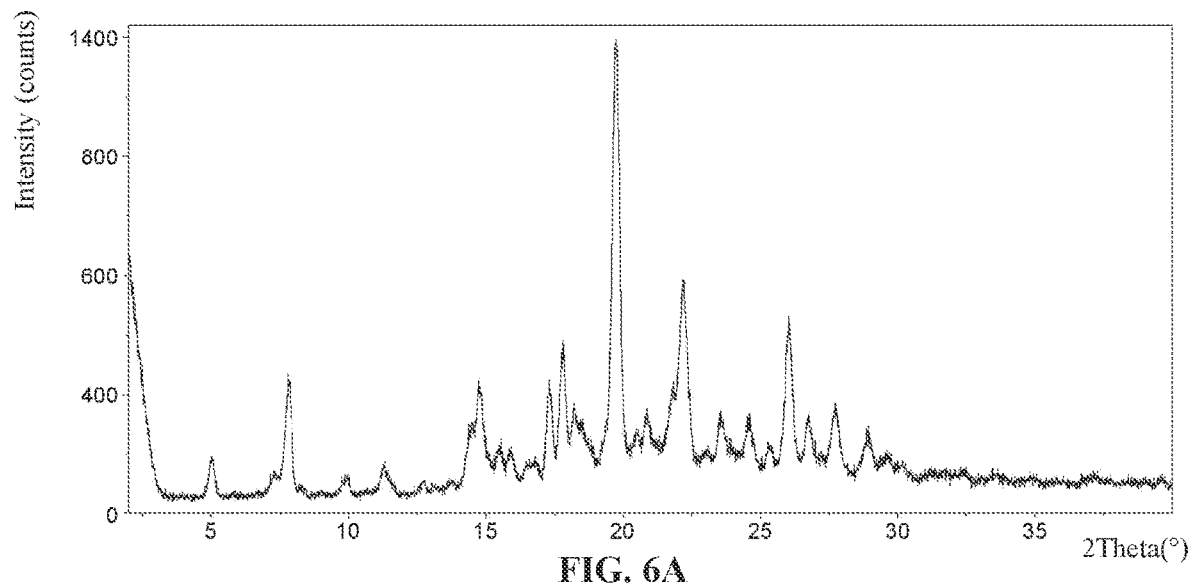
FIG. 6A is an exemplary XRPD pattern of polymorph Form XVI.
Figure 6B:
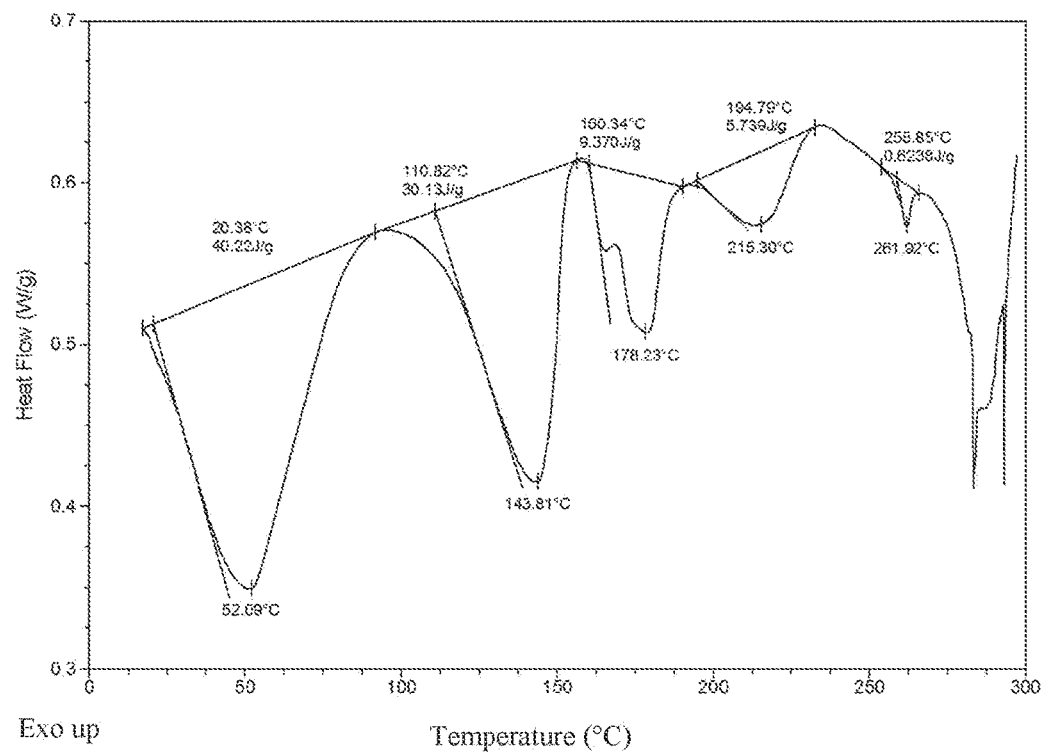
FIG. 6B is an exemplary DSC plot of polymorph Form XVI.
Figure 6C:
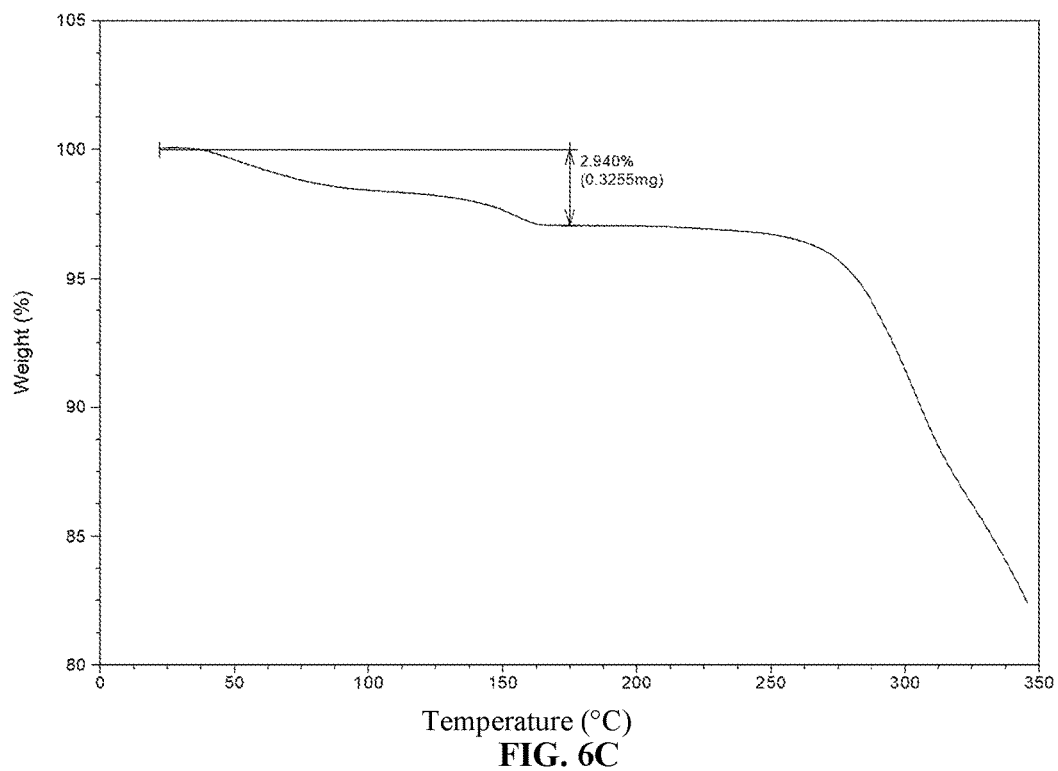
FIG. 6C is an exemplary TGA plot of polymorph Form XVI.
Figure 6D:
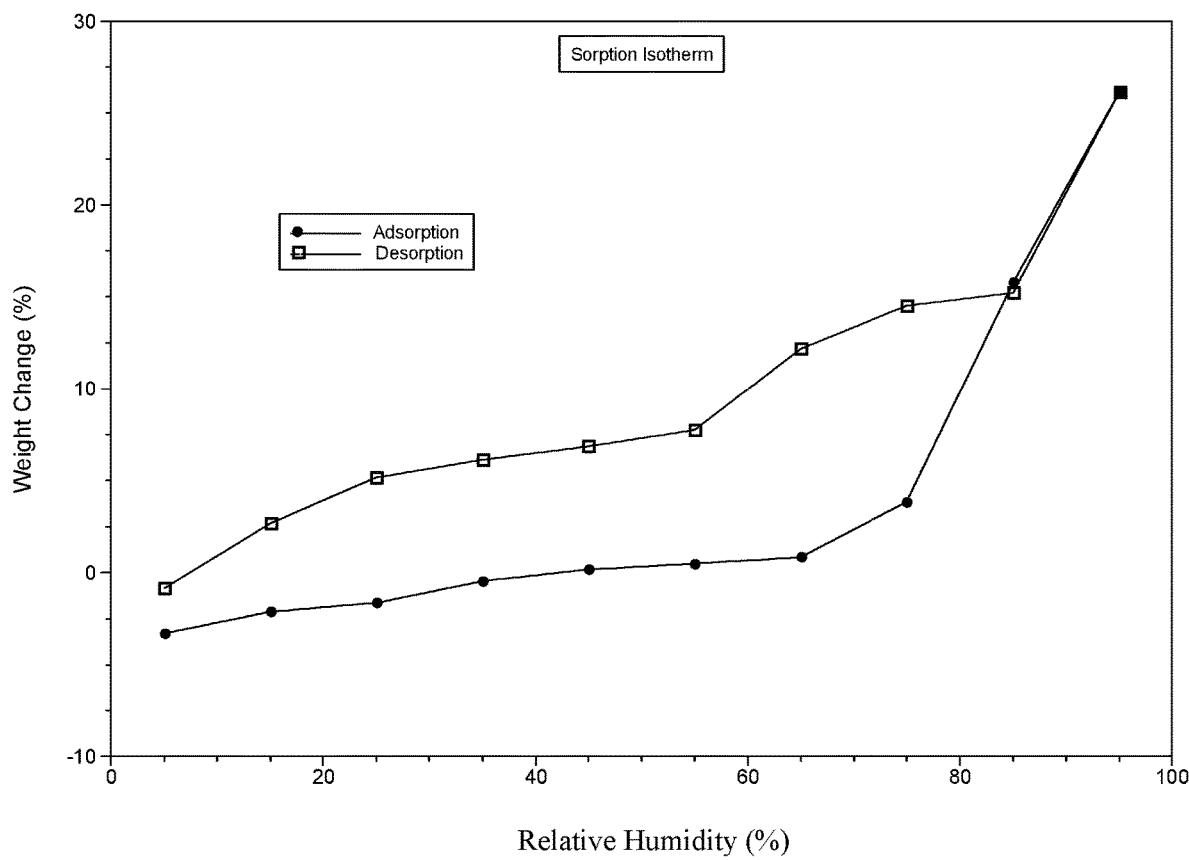
FIG. 6D shows the DVS plot of polymorph Form XVI.

Form XVI: A polymorphic form of the hydrate of bis-mesylate salt of the compound of Formula I. In some embodiments, a polymorph of a hydrate, bis-mesylate salt of a compound of Formula I is polymorph Form XVI, characterized by or having an X-ray diffraction pattern comprising 2θ-reflections (±0.2 degrees) at 5.0, 7.8, 14.8, 17.3, 17.8, 19.8, 22.2, and 26.0°. In some embodiments, a polymorph of a hydrate, bis-mesylate salt of a compound of Formula I is polymorph Form XVI, characterized by or having an X-ray diffraction pattern substantially as shown in FIG. 6A. The DSC curve is shown in FIG. 6B and indicates multiple endothermic transitions at 20, 111, 160, 195, and 259° C. The TGA curve is shown in FIG. 6C and displays a weight loss (2.9% from room temperature to 175° C.) indicating a solvate that was identified as water based on TGA-MS. The dynamic vapor sorption curve for Form XVI is shown in FIG. 6D and the data indicates that the form absorbs ~28 wt. % of water up to 95% RH at 25° C. XRPD analysis of the sample after the DVS experiment shows that the material had converted to Form VII. Form XVI was originally isolated by slurring Form VII or XIX in acetone, 1% water in acetone, or 2% water in acetone.

Figure 7A:
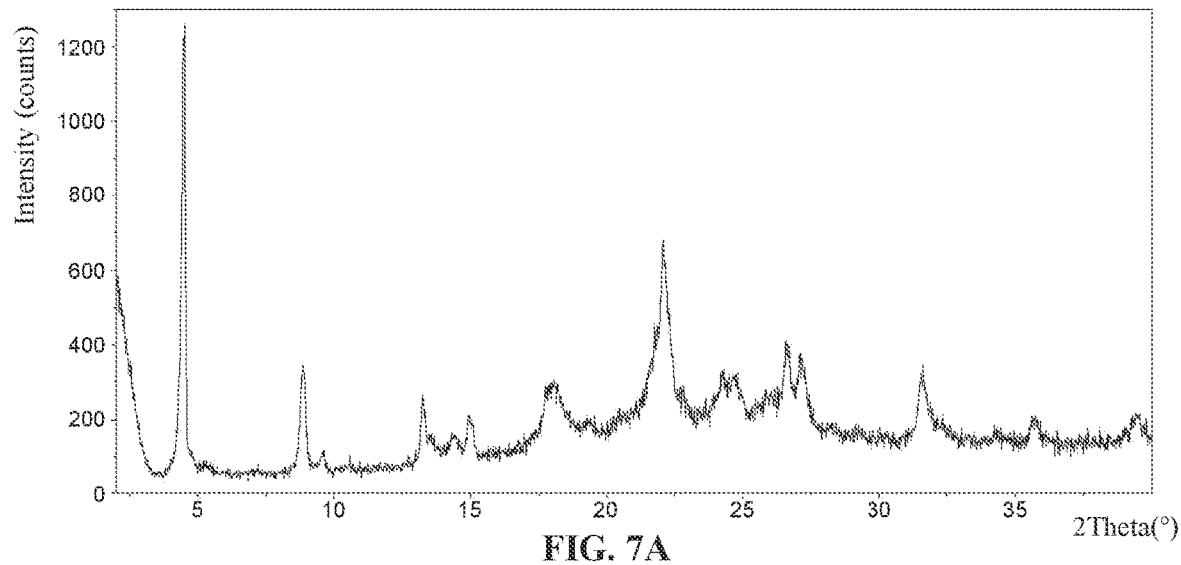
FIG. 7A is an exemplary XRPD pattern of polymorph Form XVIII.
Figure 7B:
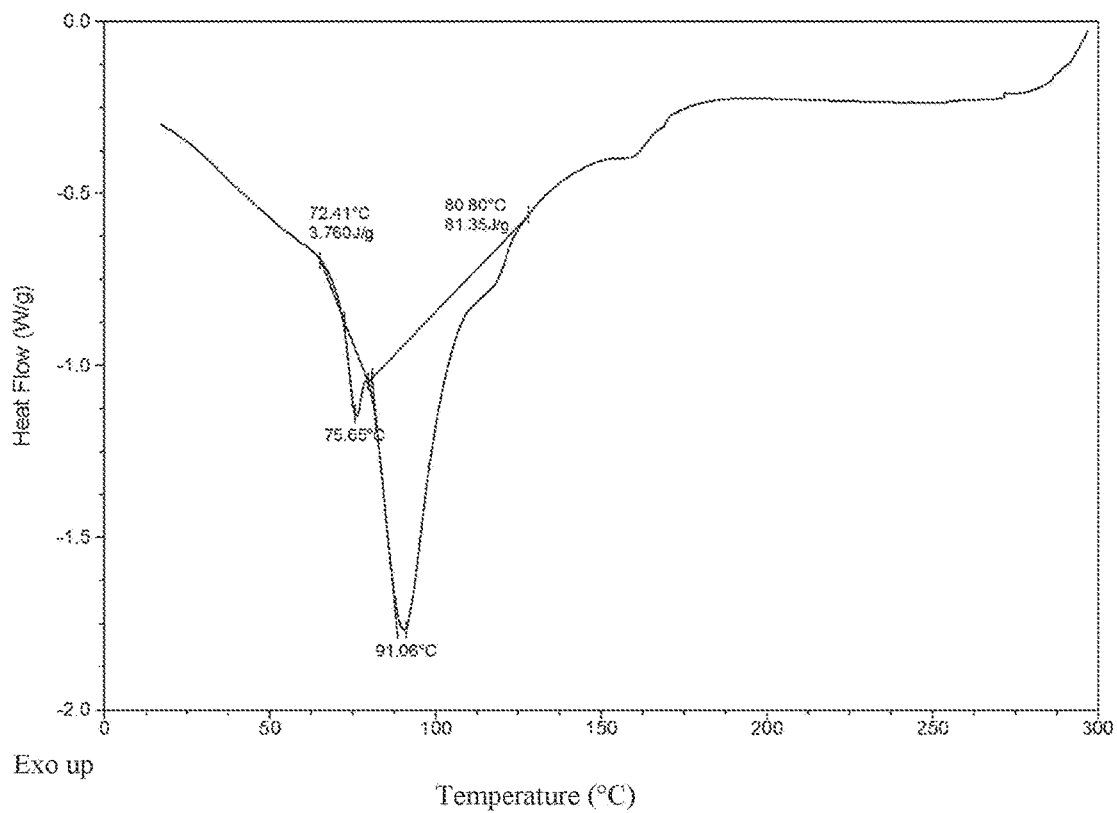
FIG. 7B is an exemplary DSC plot of polymorph Form XVIII.
Figure 7C:
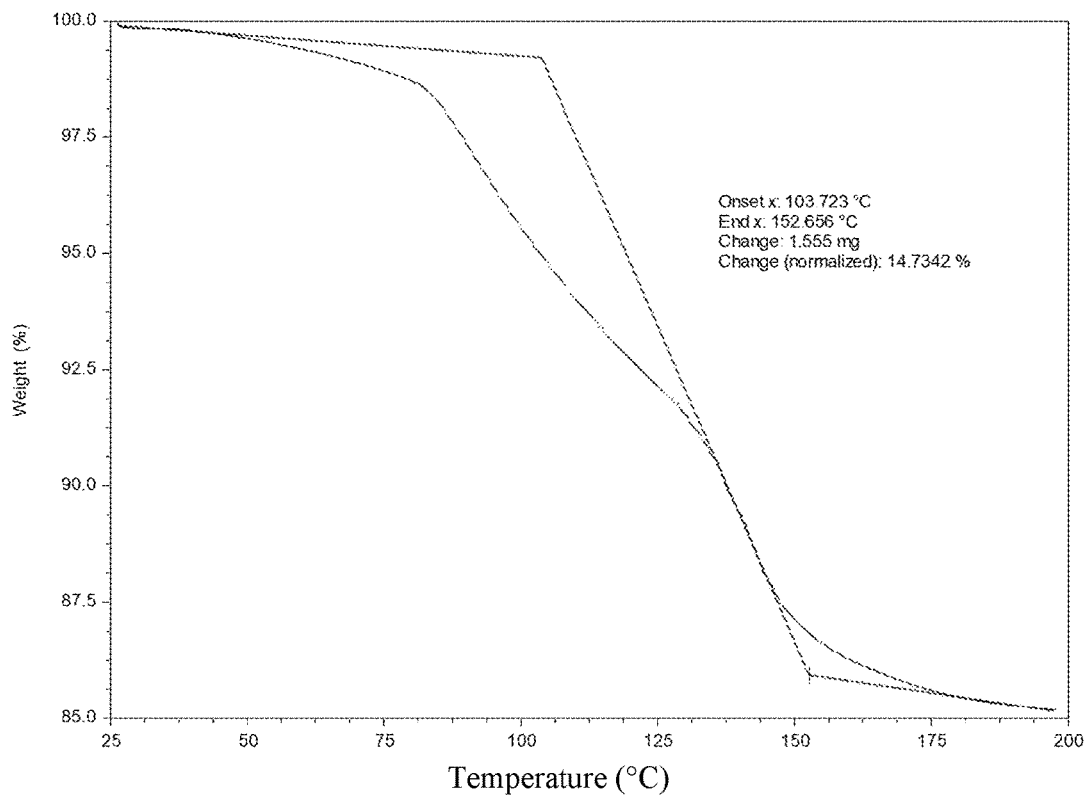
FIG. 7C is an exemplary TGA plot of polymorph Form XVIII.
Figure 7D:
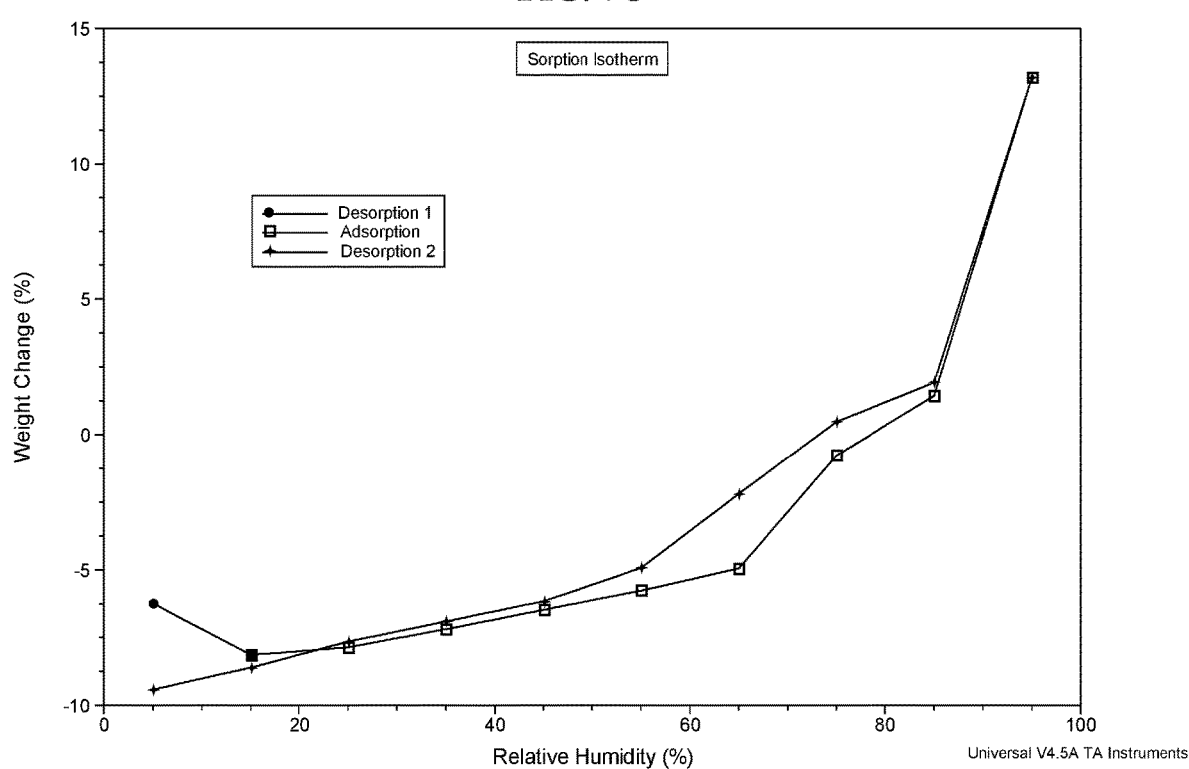
FIG. 7D shows the DVS plot of polymorph Form XVIII.

Form XVIII: A polymorphic form of the hydrate of bis-mesylate salt of the compound of Formula I. In some embodiments, a polymorph of a hydrate, bis-mesylate salt of a compound of Formula I is polymorph Form XVIII, characterized by or having an X-ray diffraction pattern comprising 2θ-reflections (±0.2 degrees) at 4.5, 8.9, 13.3, 18.0, 22.1, 24.7, 27.2, and 31.6°. In some embodiments, a polymorph of a hydrate, bis-mesylate salt of a compound of Formula I is polymorph Form XVIII, characterized by or having an X-ray diffraction pattern substantially as shown in FIG. 7A. The DSC curve is shown in FIG. 7B and indicates multiple endothermic transitions at 72 and 81° C. The TGA curve is shown in FIG. 7C and displays a weight loss (14.7% from room temperature to 200° C.) indicating a solvate that was identified as water based on TGA-Mass Spectroscopy. The dynamic vapor sorption curve for Form XV is shown in XRPD analysis of the sample after the DVS experiment shows that the material had converted to Form VII. Form XVIII was isolated when wet material from 20% water in acetone was dried in an oven at 80° C.

Figure 8A:
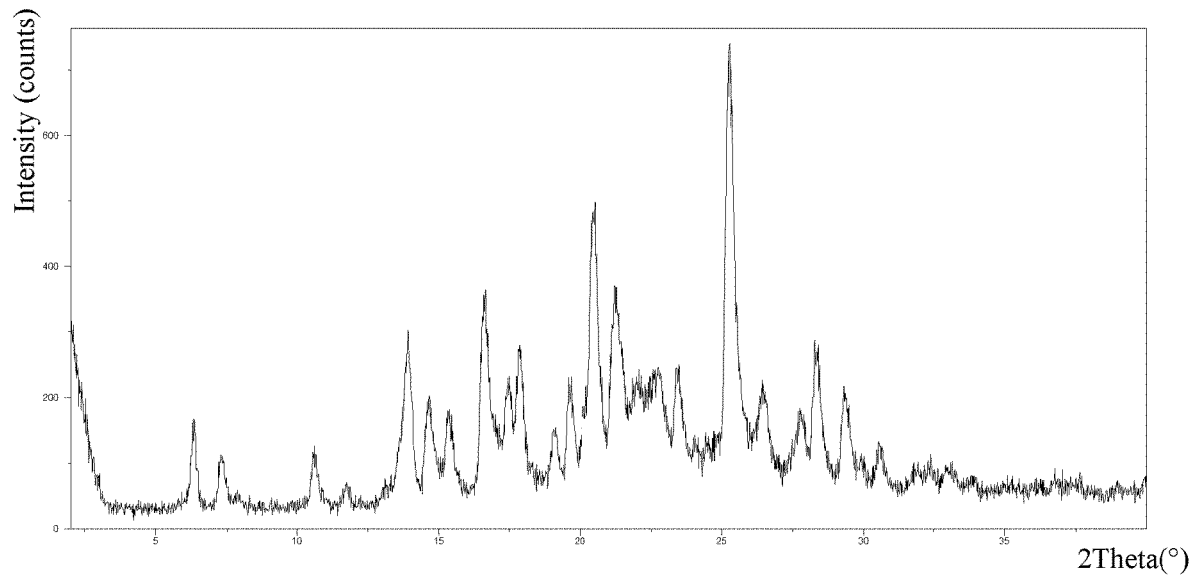
FIG. 8A is an exemplary XRPD pattern of polymorph Form VI.
Figure 8B:
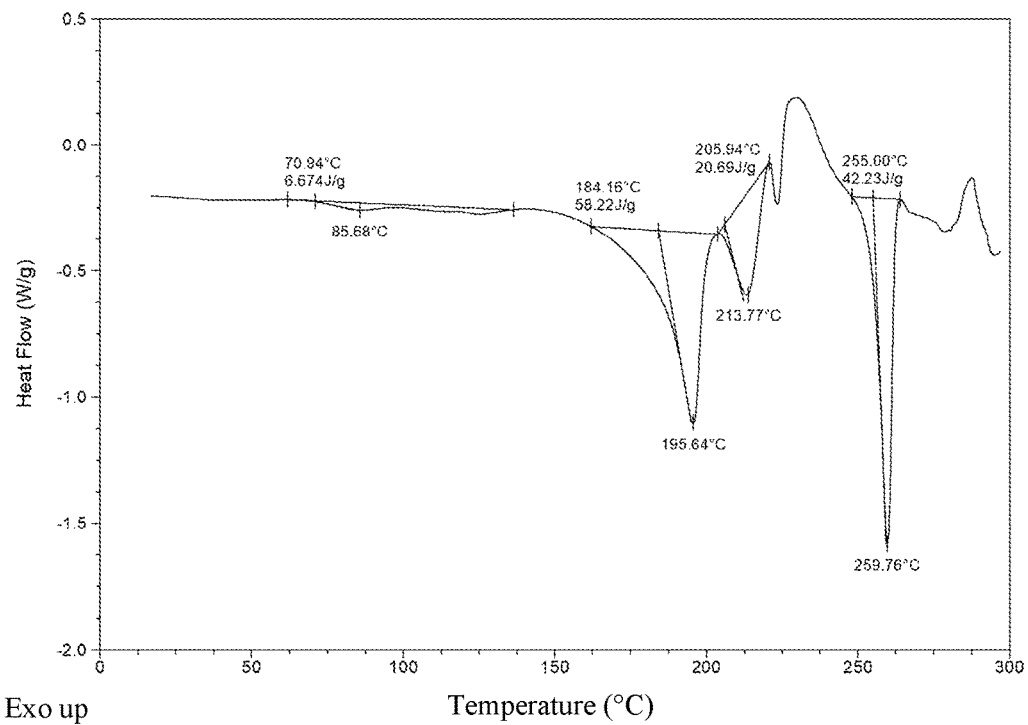
FIG. 8B is an exemplary DSC plot of polymorph Form VI.
Figure 8C:
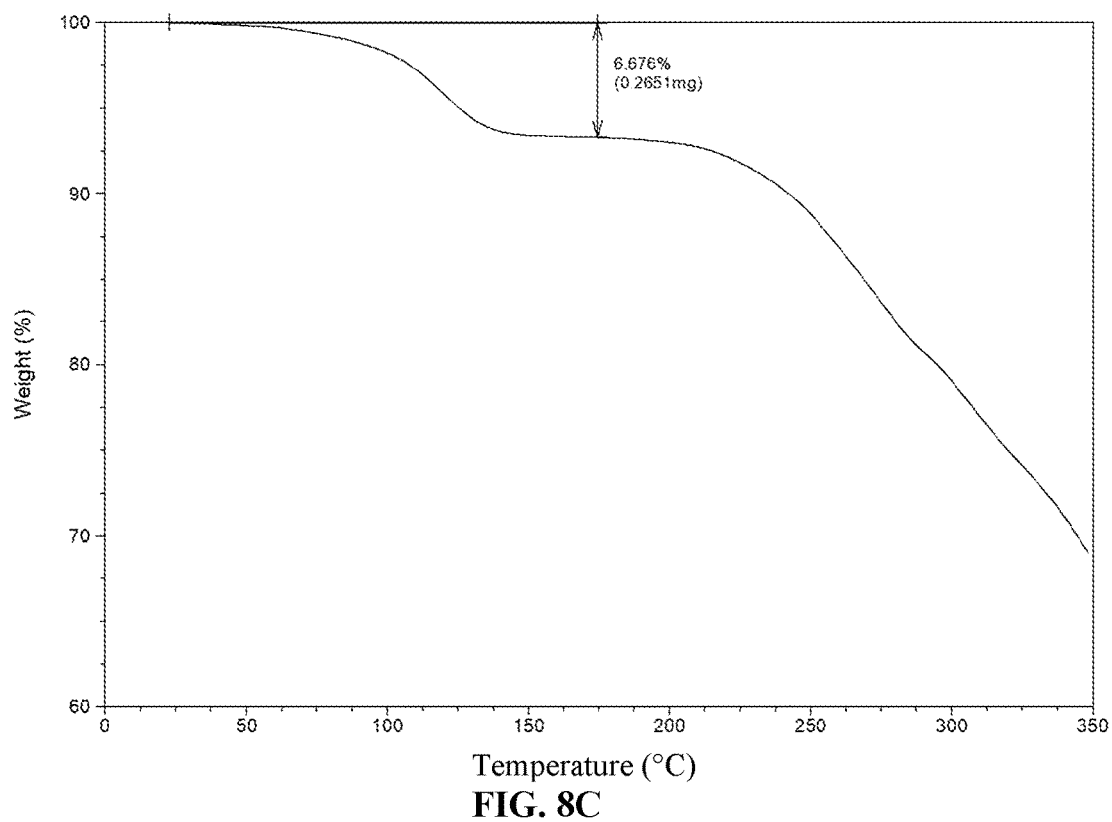
FIG. 8C is an exemplary TGA plot of polymorph Form VI.

Form VI: A polymorphic form of a formic acid solvate of bis-mesylate salt of the compound of Formula I. In some embodiments, a polymorph of a formic acid solvate of bis-mesylate salt of a compound of Formula I is polymorph Form VI, characterized by or having an X-ray diffraction pattern comprising sharp reflections at 13.9, 16.6, 20.5, and 25.2°2θ, ±0.2°2θ. It can be further characterized by peaks at 6.3, 14.6, 17.8, and 21.2°2θ, ±0.2°2θ. In some embodiments, a polymorph of a formic acid solvate of bis-mesylate salt of a compound of Formula I is polymorph Form VI, characterized by or having an X-ray diffraction pattern substantially as shown in FIG. 8A. The DSC curve is shown in FIG. 8B and indicates multiple endothermic transitions at 71, 184, 206, and 255° C. The TGA curve is shown in FIG. 8C and displays a weight loss (6.7% from room temperature to 175° C.) indicating a solvate that was identified as formic acid via ion chromatography. Weight loss above 225° C. is attributed to decomposition. Form VI was isolated when reactor A was charged with formic acid (3V, 3.6×) and ethyl acetate (2V, 1.8×) and the contents of the reactor adjusted to 22 degrees Celsius (19-25 degrees Celsius). The free base non-mesylated form of Compound of formula I (1.0×) was added portion wise with agitation while maintaining the reactor temperature at 22 degrees Celsius (19-25 degrees Celsius) and the contents agitated until all solids dissolved (about 1 hour). The solution in Reactor A was transferred to Reactor B, and formic acid (0.08V, 0.1×) was added to Reactor A along with ethyl acetate (2V, 1.8×), and methyl sulfonic acid (pharmaceutical grade, 2.0 mol equiv., 0.47×). The solution in Reactor A was transferred via polishing filter to Reactor B over 30 minutes while maintain a pot temperature of 22 degrees Celsius (19-25 degrees Celsius). Ethyl acetate (5V, 4.5×) was added to Reactor A and then to Reactor B over a minimum of 1 hour. The contents of Reactor B was agitated for 16 h. at 22 degrees Celsius (19-25 degrees Celsius), then filtered rinsed with ethyl acetate (4V, 3.6×) and dried under vacuum at 60 degrees Celsius.

In some variations, polymorphic Forms I, II, VI, XIII, XIV, XV, XVI, XVIII and XIX are characterized by or have X-ray powder diffraction (XRPD) patterns substantially as shown in FIG. 1A, 2A, 3A, 4A, 5A, 6A, 7A, 8A and 9A, respectively. It should be understood, however, that relative intensities and assignments of the peaks of polymorphic forms depicted in the figures can vary depending on a number of factors, including sample preparation, mounting, and the instrument and analytical procedure and settings used to obtain the spectrum. As such, the peaks observed in the figures and assignments listed herein are intended to encompass variations of ±0.2 degrees 2θ.

Crystalline

The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order (melting point).

For example, in one embodiment, polymorph Form I, II, VI, XIII, XIV, XV, XVI, XVIII and XIX are substantially crystalline. In some embodiments, a compound that is substantially crystalline (e.g., polymorph Form I) has greater than 50%; or greater than 55%; or greater than 60%; or greater than 65%; or greater than 70%; or greater than 75%; or greater than 80%; or greater than 85%; or greater than 90%; or greater than 95%, or greater than 99% of the compound present in a composition in crystalline form. In other embodiments, a compound that is substantially crystalline (e.g., polymorph Form I) has no more than about 20%, or no more than about 10%, or no more than about 5%, or no more than about 2% in the amorphous form. In yet other embodiments, a compound that is substantially crystalline (e.g., polymorph Form I) has no more than about 20%, or no more than about 10%, or no more than about 5%, or no more than about 2% in the non-crystalline form.

Methods of Preparing Polymorph Forms

In some embodiments, provided is a method of preparing polymorph Form I, which is a polymorph of a hydrate, bis-mesylate salt of a compound of Formula I, comprising heating Form VI at about 130-170° C., or at about 150° C., for about one to three hours in an appropriate container or by heating Form III at about 155-195° C., or at about 175° C., for about one to three hours in an appropriate container. Once the desired amount of conversion from Form VI to Form I is completed, the polymorph can be cooled to room temperature.

In some embodiments, provided is a method of preparing polymorph Form II, which is a polymorph of a hydrate, bis-mesylate salt of a compound of Formula I, comprising heating Form VI at about 100-130° C., or at about 120° C., under vacuum in an appropriate container. Once the desired amount of conversion from Form VI to Form II is completed, the polymorph can be cooled to room temperature. In some embodiments, provided is a method of preparing polymorph Form II by forming a slurry of Form VI in a solvent, such as isopropyl alcohol, at room temperature and stirring for about one week. In some embodiments, provided is a method of preparing polymorph Form II, comprising adding an amount of polymorph Form II seeds (obtained for example, by methods described above or elsewhere herein) and at least one solvent, for example isopropyl alcohol, to polymorph Form VI to form a mixture and isolating polymorph Form II. In some embodiments of the methods provided above, the amount of seed is an amount sufficient to initiate nucleation. In some embodiments, the amount of Form II seeds added to polymorph Form VI is between about 0.001 and about 0.1 weight percent of polymorph Form VI. In some embodiments, the amount of Form II seeds added to polymorph Form VI is between about 0.01 and about 0.1 weight percent of polymorph Form VI. In some embodiments, the amount of Form II seeds added to polymorph Form VI is between about 0.01 and about 0.08 weight percent of polymorph Form VI. In some embodiments, the amount of Form II seeds added to polymorph Form VI is about 0.015 weight percent of polymorph Form VI. In one embodiment, however, one or more of the steps of the method to prepare polymorph Form II from Form VI may be omitted or the order of the steps may be varied. For instance, in alternative embodiments, the methods of making Form II do not require adding seeds of Form II to Form VI. In some embodiments, the method comprises the steps of heating and cooling the mixture. In some embodiments, polymorph Form VI is not isolated from the reaction mixture but generated in situ and converted to Form II.

In some embodiments, provided is a method of preparing polymorph Form XIII, which is a polymorph of a hydrate, bis-mesylate salt of a compound of Formula I, comprising exposing polymorphic Form VII to about zero percentage humidity, such as in a $P_2O_5$ chamber, at about 30-60° C. under vacuum. In some embodiments, the temperature in the vacuum chamber is about 40° C. Desiccants, such as, $CaSO_4$ (Drierite), silica gel, $MgSO_4$, and $P_2O_5$ can be used to maintain low humidity.

In some embodiments, provided is a method of preparing polymorph Form XIV, which is an unsolvated polymorph of bis-mesylate salt of a compound of Formula I, comprising heating polymorph Form I, Form II, Form III, or Form XVI to about 250° C.

In some embodiments, provided is a method of preparing polymorph Form XV, which is a polymorph of a hydrate, bis-mesylate salt of a compound of Formula I, comprising slurring mixture of Form III with Form XV in about 1.5-5% of water in acetone at room temperature. In one embodiment, about 2.5% of water in acetone can be used. In some embodiments, provided is a method of preparing polymorph Form XV, comprising slurring Form VII in about 2-7% water in acetone at room temperature, or optionally, about 4% water in acetone can be used.

In some embodiments, provided is a method of preparing polymorph Form XV, comprising adding an amount of polymorph Form XV seeds to the slurry mixture in 4% water in acetone at room temperature for several days. In some embodiments of the methods provided above, the amount of seed is an amount sufficient to initiate nucleation. In some embodiments, the amount of Form XV seeds added to the slurry is between about 0.001 and about 0.1 weight percent of polymorph Form III or VII. In some embodiments, the amount of Form XV seeds added to polymorph Form III or VII is between about 0.01 and about 0.1 weight percent of the starting polymorph form. In some embodiments, polymorph Form III or VII is not isolated from the reaction mixture but generated in situ and converted to Form XV.

In some embodiments, provided is a method of preparing polymorph Form XVI, which is a polymorph of a hydrate, bis-mesylate salt of a compound of Formula I, comprising slurring Form VII or XIX in acetone, 1% water in acetone, or 2% water in acetone, or Form VII in acetone at room temperature for about 1 day. Form XVI can also be prepared by slurring amorphous material in about 0.5-3% water in acetone for about 1-5 days at room temperature. The solvent can be about 1-2% water in acetone. In some embodiments, provided is a method of preparing polymorph Form XVI, comprising adding an amount of polymorph Form XVI seeds to the slurry mixture. In some embodiments of the methods provided above, the amount of seed is an amount sufficient to initiate nucleation. In some embodiments, the amount of Form XVI seeds added to the slurry is between about 0.001 and about 0.1 weight percent of polymorph Form VII. In some embodiments, the amount of Form XVI seeds added to polymorph Form VII is between about 0.01 and about 0.1 weight percent of the starting polymorph form. In some embodiments, polymorph Form VII is not isolated from the reaction mixture but generated in situ and converted to Form XVI.

In some embodiments, provided is a method of preparing polymorph Form XVIII, which is a polymorph of a hydrate, bis-mesylate salt of a compound of Formula I, comprising slurrying compound of Formula I in a solvent of about 20% water in acetone and drying at a temperature of about 80° C. under vacuum.

In some embodiments, provided is a method of preparing polymorph Form XIX, which is a polymorph of a hydrate, bis-mesylate salt of a compound of Formula I, comprising dissolving Form III in water and spray-drying the solution.

In some embodiments of the methods, a mixture is formed. In some embodiments, the mixture is a homogeneous solution. In other embodiments, the mixture is heterogeneous, wherein the mixture comprises more than one phase, for instance a solid phase and a liquid phase. In some embodiments the mixture is a slurry. In some embodiments, a portion of the contents of a mixture may undergo phase change over time. For instance, a homogenous solution mixture may form solids over time and become a heterogeneous mixture, wherein the mixture comprises a solid and liquid phase. Alternatively, a heterogeneous mixture may become a homogenous solution mixture, for instance when a solid material dissolves into a solvent. In some embodiments the phase change occurs upon a reaction event. For instance, a homogenous solution mixture may, upon a reaction event, may become a heterogeneous mixture, and vice versa. The reaction event may be a change in the conditions of the reaction mixture, for instance, cooling or heating, addition of a particular solvent, addition of a solid, or evaporation.

In some embodiments, at least one solvent is added to the mixture. Non-limiting examples of solvents include methanol, ethanol, isopropanol, ethyl acetate, isopropyl acetate, acetone, tetrahydrofuran, toluene, methyl-t-butyl ether, acetonitrile, heptanes, n-heptane, hexanes, water, methyl ethyl ketone, dichloromethane, 2-methyl-tetrahydrofuran, and methyl isobutyl ketone. In some embodiments, the solvent is acetone. In other embodiments, the solvents are acetone and water. In some embodiments, the at least one solvent is an organic solvent. In some embodiments, the solvent is a mixture containing 0.1-8% water. In some embodiments, the at least one solvent is an organic solvent, further comprising water. Non-limiting examples of organic solvents include methanol, ethanol, isopropanol, ethyl acetate, isopropyl acetate, acetone, tetrahydrofuran, toluene, methyl-t-butyl ether, acetonitrile, heptanes, n-heptane, hexanes, methyl ethyl ketone, dichloromethane, 2-methyl-tetrahydrofuran, and methyl isobutyl ketone. In some embodiments, the at least one solvent further comprises a protic solvent. Non-limiting examples of a protic solvent include water, methanol, ethanol, isopropanol, propanol, and butanol. In some embodiments, the at least one solvent is acetone, further comprising water.

Deuterated Compounds

Any formula or structure given herein, including a compound of Formula I and pharmaceutically acceptable salts thereof (including, for example, the mono-mesylate and the bis-mesylate salts), or a hydrate thereof, is also contemplated as an isotopically labeled form of the compounds, or salts, or hydrates thereof. Thus, although the unlabeled forms of compounds are provided, it is understood that the present disclosure also contemplates isotopically labeled compounds, even though such isotopes are not explicitly depicted. Isotopically labeled compounds, or salts, or hydrates thereof have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), (tritium), $^3$C, $^{13}$C, $^{14}$C, $^{15}$N, $^{18}$F, $^{31}$P, $^{32}$P, $^{35}$S, $^{36}$Cl and $^{125}$I. For instance, isotopes of hydrogen, carbon, nitrogen, oxygen, phosphorous, fluorine and chlorine, such as, but not limited to $^2$H (deuterium, D), $^3$H (tritium) $^{11}$C, $^{13}$C, $^{14}$C, $^{15}$N and $^{35}$S may be incorporated into a compound of formula I, including a salt (e.g. a mesylate salt) of a compound of formula I, or a hydrate thereof. Various isotopically labeled compounds, or salts, or hydrates thereof of the present disclosure, for example those into which radioactive isotopes such as $^3$H, $^{13}$C and $^{14}$C are incorporated. Such isotopically labeled compounds or salts thereof may be useful in metabolic studies, reaction kinetic studies, detection or imaging techniques, such as positron emission tomography (PET) or single-photon emission computed tomography (SPECT) including drug or substrate tissue distribution assays or in radioactive treatment of subjects.

The disclosure also includes a compound of Formula I and pharmaceutically acceptable salts thereof (including, for example, the mono-mesylate and the bis-mesylate salts), or a hydrate thereof, in which from 1 to n hydrogens attached to a carbon atom is/are replaced by deuterium, in which n is the number of hydrogens in the molecule. Such compounds may exhibit increased resistance to metabolism and are thus useful for increasing the half-life of a compound of Formula I, or pharmaceutically acceptable salts thereof, or hydrates thereof when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

Deuterium labeled or substituted therapeutic compounds of the disclosure (including salts or hydrates thereof) may have improved DMPK (drug metabolism and pharmacokinetics) properties, relating to absorption, distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I and pharmaceutically acceptable salts thereof (including, for example, the mono-mesylate and the bis-mesylate salts), or hydrates thereof.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds or salts thereof of this disclosure any atom specifically designated as a deuterium (D) is meant to represent deuterium.

Pharmaceutical Composition

The bis-mesylate salts described herein and any polymorphic forms thereof described herein, can be administered as the neat chemical, but it is typical, to administer the compound, or salt or hydrate thereof, in the form of a pharmaceutical composition or formulation. Provided are pharmaceutical compositions comprising: (i) a bis-mesylate salt polymorph selected from Form I, II, VI, XIII, XIV, XV, XVI, XVIII and XIX of a compound of Formula I (ii) a pharmaceutical carrier, excipient, adjuvant, or vehicle. Pharmaceutical carrier, excipient, adjuvant, or vehicle may also be referred to herein as pharmaceutically acceptable carrier excipient, adjuvant or vehicle or as biocompatible pharmaceutical carrier, excipient, adjuvant, or vehicle. The composition can include a polymorphic form of bis-mesylate salt of a compound of Formula I selected from polymorphic forms I, II, VI, XIII, XIV, XV, XVI, XVIII and XIX described herein either as the sole active agent or in combination with other agents, such as oligo- or polynucleotides, oligo- or polypeptides, drugs, or hormones mixed with one or more pharmaceutically acceptable carriers or excipients. Carriers, excipients, and other ingredients can be deemed pharmaceutically acceptable insofar as they are compatible with other ingredients of the formulation and not deleterious to the recipient thereof.

The term "carrier" refers to diluents, disintegrants, precipitation inhibitors, surfactants, glidants, binders, lubricants, and other excipients and vehicles with which the compound is administered. Carriers are generally described herein and also in "Remington's Pharmaceutical Sciences" by E. W. Martin.

The pharmaceutical compositions can be formulated to contain suitable pharmaceutically acceptable carriers, and optionally can comprise excipients and auxiliaries that facilitate processing of the polymorphic forms described herein into preparations that can be used pharmaceutically. The mode of administration generally determines the nature of the carrier. For example, formulations for parenteral administration can include aqueous solutions of the active compounds in water-soluble form. Carriers suitable for parenteral administration can be selected from among saline, buffered saline, dextrose, water, and other physiologically compatible solutions. Exemplary carriers for parenteral administration are physiologically compatible buffers such as Hanks's solution, Ringer's solution, or physiologically buffered saline. For tissue or cellular administration, penetrants appropriate to the particular barrier to be permeated are used in the formulation. Such penetrants are generally known in the art. For preparations including proteins, the formulation can include stabilizing materials, such as polyols (e.g., sucrose) and/or surfactants (e.g., nonionic surfactants), and the like.

Alternatively, formulations for parenteral use can include dispersions or suspensions of polymorphic forms described herein prepared as appropriate oily injection suspensions. Suitable lipophilic solvents or vehicles include fatty oils, such as sesame oil, and synthetic fatty acid esters, such as ethyl oleate or triglycerides, or liposomes. Aqueous injection suspensions can contain substances that increase the viscosity of the suspension, such as sodium carboxymethylcellulose, sorbitol, dextran, and mixtures thereof. Optionally, the suspension also can contain suitable stabilizers or agents that increase the solubility of the compounds to allow for the preparation of highly concentrated solutions. Aqueous polymers that provide pH-sensitive solubilization and/or sustained release of the active agent also can be used as coatings or matrix structures, e.g., methacrylic polymers, such as the EUDRAGIT™ series available from Rohm America Inc. (Piscataway, N.J.). Emulsions, e.g., oil-in-water and water-in-oil dispersions, also can be used, optionally stabilized by an emulsifying agent or dispersant (surface active materials; surfactants). Suspensions can contain suspending agents such as ethoxylated isostearyl alcohols, polyoxyethylene sorbitol and sorbitan esters, microcrystalline cellulose, aluminum metahydroxide, bentonite, agar-agar, gum tragacanth, and mixtures thereof.

Liposomes containing the polymorphic forms described herein also can be employed for parenteral administration. Liposomes generally are derived from phospholipids or other lipid substances. The compositions in liposome form also can contain other ingredients, such as stabilizers, preservatives, excipients, and the like. Exemplary lipids include phospholipids and phosphatidyl cholines (lecithins), both natural and synthetic. Methods of forming liposomes are known in the art. See, e.g., Prescott (Ed.), Methods in Cell Biology, Vol. XIV, p. 33, Academic Press, New York (1976).

In some embodiments, the polymorph, or composition thereof, disclosed herein is formulated for oral administration using pharmaceutically acceptable carriers well known in the art. Preparations formulated for oral administration can be in the form of tablets, pills, capsules, cachets, dragees, lozenges, liquids, gels, syrups, slurries, elixirs, suspensions, or powders. To illustrate, pharmaceutical preparations for oral use can be obtained by combining the active compounds with a solid excipient, optionally grinding the resulting mixture, and processing the mixture of granules, after adding suitable auxiliaries if desired, to obtain tablets or dragee cores. Oral formulations can employ liquid carriers similar in type to those described for parenteral use, e.g., buffered aqueous solutions, suspensions, and the like.

Exemplary oral formulations include tablets, dragees, and gelatin capsules. These preparations can contain one or more excipients, which include, without limitation: a) diluents, such as microcrystalline cellulose and sugars, including lactose, dextrose, sucrose, mannitol, or sorbitol; b) binders, such as sodium starch glycolate, croscarmellose sodium, magnesium aluminum silicate, starch from corn, wheat, rice, potato, etc.; c) cellulose materials, such as methylcellulose, hydroxypropylmethyl cellulose, and sodium carboxymethylcellulose, polyvinylpyrrolidone, gums, such as gum arabic and gum tragacanth, and proteins, such as gelatin and collagen; d) disintegrating or solubilizing agents such as cross-linked polyvinyl pyrrolidone, starches, agar, alginic acid or a salt thereof, such as sodium alginate, or effervescent compositions; e) lubricants, such as silica, talc, stearic acid or its magnesium or calcium salt, and polyethylene glycol; f) flavorants and sweeteners; g) colorants or pigments, e.g., to identify the product or to characterize the quantity (dosage) of active compound; and h) other ingredients, such as preservatives, stabilizers, swelling agents, emulsifying agents, solution promoters, salts for regulating osmotic pressure, and buffers.

Examples of carriers include, but are not limited to, aluminum monostearate, aluminum stearate, carboxymethylcellulose, carboxymethylcellulose sodium, crospovidone, glyceryl isostearate, glyceryl monostearate, hydroxyethylcellulose, hydroxymethylcellulose, hydroxyoctacosanyl hydroxystearate, hydroxypropylcellulose, hydroxypropylmethylcellulose, lactose, lactose monohydrate, magnesium stearate, mannitol, microcrystalline cellulose, poloxamer 124, poloxamer 181, poloxamer 182, poloxamer 188, poloxamer 237, poloxamer 407, povidone, silicon dioxide, colloidal silicon dioxide, silicone, silicone adhesive 4102, and silicone emulsion. It should be understood, however, that the carriers selected for the pharmaceutical compositions provided in the present disclosure, and the amounts of such carriers in the composition, may vary depending on the method of formulation (e.g., dry granulation formulation, solid dispersion formulation).

In certain variations, the pharmaceutical composition comprises a polymorph selected from Form I, II, VI, XIII, XIV, XV, XVI, XVIII and XIX, and at least one pharmaceutically acceptable carrier selected from the group consisting of hydroxypropylmethylcellulose, mannitol, crospovidone, poloxamer, colloidal silicon dioxide, microcrystalline cellulose, magnesium stearate, and any mixtures thereof. In another variation, the pharmaceutical composition comprises polymorph selected from Form I, II, VI, XIII, XIV, XV, XVI, XVIII and XIX, hydroxypropylmethylcellulose, and at least one additionally pharmaceutically acceptable carrier selected from the group consisting of mannitol, crospovidone, poloxamer, colloidal silicon dioxide, microcrystalline cellulose, magnesium stearate, and any mixtures thereof.

It should also be understood that the pharmaceutically acceptable carriers described above may perform one or more different functions in a given formulation, and may fall within one or more functional classes of carriers (e.g., disintegrants, lubricants, diluents).

It should further be understood that, in other embodiments, the pharmaceutical composition may comprise one or more additional carriers to improve flow, compression, hardness, taste, and tablet performance.

In some embodiments, the pharmaceutical composition comprises a) about 34% w/w of a mesylate salt (including, for example, a mono-mesylate or bis-mesylate salt) of a compound of Formula I; b) about 15% w/w HPMC; c) about 22% w/w mannitol; d) about 10% w/w crospovidone; and e) about 1% w/w to about 3% w/w poloxamer. In one variation, the pharmaceutical composition comprises: a) about 34% w/w of a bis-mesylate salt of a compound of Formula I, or a hydrate thereof; b) about 15% w/w HPMC; c) about 22% w/w mannitol; d) about 10% w/w crospovidone; and e) about 1% w/w to about 3% w/w poloxamer. In another variation, the pharmaceutical composition comprises: a) about 34% w/w of a monohydrate, bis-mesylate salt of a compound of Formula I; b) about 15% w/w HPMC; c) about 22% w/w mannitol; d) about 10% w/w crospovidone; and e) about 1% w/w to about 3% w/w poloxamer. In yet another variation, the pharmaceutical composition comprises: a) about 34% w/w of polymorph Form 3, polymorph Form 7, or a combination thereof; b) about 15% w/w HPMC; c)

about 22% w/w mannitol; d) about 10% w/w crospovidone; and e) about 1% w/w to about 3% w/w poloxamer.

Methods of Use

Provided is also the use of the pharmaceutical compositions described in the present disclosure to selectively or specifically inhibit Syk activity therapeutically or prophylactically. The method comprises administering the pharmaceutical composition to an individual in need thereof in an amount sufficient to inhibit Syk activity. The method can be employed to treat subjects (e.g., humans) suffering from, or subject to, a condition whose symptoms or pathology is mediated by Syk expression or activity. In one aspect, provided is a method of treating a human in need thereof, comprising administering a bis-mesylate salt polymorph of a compound of Formula I selected from Form I, II, VI, XIII, XIV, XV, XVI, XVIII and XIX, to the human.

"Treatment" or "treating" is an approach for obtaining beneficial or desired results including clinical results. Beneficial or desired clinical results may include one or more of the following:

a) inhibiting the disease or condition (e.g., decreasing one or more symptoms resulting from the disease or condition, and/or diminishing the extent of the disease or condition);

b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" of the pharmaceutical composition means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of Syk activity. The therapeutically effective amount may vary depending on the subject, and disease or condition being treated, the weight and age of the subject, the severity of the disease or condition, and the manner of administering, which can readily be determined by one or ordinary skill in the art.

The term "inhibition" indicates a decrease in the baseline activity of a biological activity or process. "Inhibition of activity of Syk activity" refers to a decrease in activity of Syk as a direct or indirect response to the presence of the pharmaceutical composition, relative to the activity of Syk in the absence of such pharmaceutical composition. In some embodiments, the inhibition of Syk activity may be compared in the same subject prior to treatment, or other subjects not receiving the treatment.

In certain aspects, a bis-mesylate salt polymorph of a compound of Formula I selected from Form I, II, VI, XIII, XIV, XV, XVI, XVIII and XIX, and compositions thereof described herein are used for treating a subject having cancer, an allergic disorder and/or an autoimmune and/or inflammatory disease, and/or an acute inflammatory reaction.

In one aspect, the pharmaceutical compositions provided in the present disclosure may be used in the treatment of cancer. In some embodiments, the polymorphs and compositions thereof described herein can be employed in methods of inhibiting the growth or proliferation of cancer cells of hematopoietic origin. In some embodiments, the cancer cells are of lymphoid origin, and in specific embodiments, the cancer cells are related to or derived from B lymphocytes or B lymphocyte progenitors.

Cancers amenable to treatment using the method disclosed in the present disclosure include, without limitation, lymphomas (e.g., malignant neoplasms of lymphoid and reticuloendothelial tissues, such as Burkitt's lymphoma, Hodgkins' lymphoma, non-Hodgkins' lymphomas, lymphocytic lymphomas); multiple myelomas; leukemias (e.g., lymphocytic leukemias, chronic myeloid (myelogenous) leukemias). Other cancer cells, of hematopoietic origin or otherwise, that express spleen tyrosine kinase (Syk) also can be treated by administration of the polymorphs and compositions thereof described herein.

In particular embodiments of the methods provided herein, the cancer is leukemia or lymphoma. In certain embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CIVIL), multiple myeloma (MM), indolent non-Hodgkin's lymphoma (iNHL), refractory iNHL, non-Hodgkin's lymphoma (NHL), mantle cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), and marginal zone lymphoma (MZL). In certain variations, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma (FL), Waldestrom's macroglobulinemia (WM), T-cell lymphoma, B-cell lymphoma, and diffuse large B-cell lymphoma (DLBCL). In one embodiment, the cancer is T-cell acute lymphoblastic leukemia (T-ALL), or B-cell acute lymphoblastic leukemia (B-ALL). The non-Hodgkin lymphoma encompasses the indolent B-cell diseases that include, for example, follicular lymphoma, lymphoplasmacytic lymphoma, Waldenstrom macroglobulinemia, and marginal zone lymphoma, as well as the aggressive lymphomas that include, for example, Burkitt lymphoma, diffuse large B-cell lymphoma (DLBCL) and mantle cell lymphoma (MCL). In one embodiment, the cancer is indolent non-Hodgkin's lymphoma (iNHL). In yet another embodiment, the cancer is non-FL iNHL.

In particular embodiments of the methods provided herein, the cancer is a hematologic malignancy. In certain embodiments, the hematologic malignancy is leukemia (e.g., chronic lymphocytic leukemia) or lymphoma (e.g., non-Hodgkin's lymphoma). In some variations, the cancer is MCL, DLBCL, iNHL, FL, MZL, LPL, SLL, or WM. In other variations, the cancer is CLL, MCL, DLBCL, iNHL (including, for example, non-FL iNHL), or FL.

In other embodiments, the cancer is a solid tumor cancer (or solid cancer tumor). In certain embodiments the cancer is a solid tumor and expresses spleen tyrosine kinase (Syk) activity. In other embodiments, the solid tumor cancer is selected from the group consisting of pancreatic cancer, lung cancer, colon cancer, colorectal cancer, breast cancer, esophageal cancer, adenocarcinoma, hepatocellular cancer. In one embodiment, the solid tumor cancer is selected from the group consisting of pancreatic cancer, lung cancer, colorectal cancer, ovarian cancer, and hepatocellular cancer.

Any of the methods of treatment provided herein may be used to treat cancer at an advanced stage. Any of the methods of treatment provided herein may be used to treat cancer at locally advanced stage. Any of the methods of treatment provided herein may be used to treat early stage cancer. Any of the methods of treatment provided herein may be used to treat cancer in remission. In some embodiments of any of the methods of treatment provided herein, the cancer has reoccurred after remission. In some embodiments of any of the methods of treatment provided herein, the cancer is progressive cancer.

In some embodiments, the conditions and diseases that can be affected using the compounds and the compositions described herein, include, but are not limited to: allergic disorders, including but not limited to eczema, allergic rhinitis or coryza, hay fever, bronchial asthma, urticaria (hives) and food allergies, and other atopic conditions; autoimmune and/or inflammatory diseases, including but not limited to psoriasis, ulcerative colitis, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic obstructive pulmonary disease (COPD), adult respiratory distress syndrome (ARDS), chronic Idiopathic thrombocytopenic purpura (ITP), Addison's disease, Parkinson's disease, Alzheimer's disease, diabetes, septic shock, and myasthenia gravis; acute inflammatory reactions, including but not limited to skin sunburn, inflammatory pelvic disease, inflammatory bowel disease, urethritis, uvitis, sinusitis, pneumonitis, encephalitis, meningitis, myocarditis, nephritis, osteomyelitis, myositis, hepatitis gastritis, enteritis, dermatitis, gingivitis, appendicitis, pancreatitis, and cholocystitis; polycystic kidney disease.

In some embodiments, provided are also the use of the compounds and compositions described herein in the treatment of an autoimmune disease. Certain embodiments of an autoimmune disease include asthma, rheumatoid arthritis, multiple sclerosis, and lupus.

In yet another aspect, provided are methods of treating an individual having a Syk-mediated disorder by administering any of the pharmaceutical compositions provided in the present disclosure to the individual. Provided are also methods of modulating Syk in an individual by administering any of the pharmaceutical compositions provided in the present disclosure to the individual.

In some embodiments, the pharmaceutical composition comprising a bis-mesylate salt polymorph of a compound of Formula I selected from Form I, II, VI, XIII, XIV, XV, XVI, XVIII and XIX is administered to a patient that is undergoing at least one, at least two, at least three, or at least four anti-cancer therapy (including, for example, standard or experimental chemotherapy) selected from fludarabine, rituximab, obinutuzumab, alkylating agents, alemtuzumab and other chemotherapy treatments such as CHOP (cyclophosphamide, doxorubicin, vincristine, prednisone); R CHOP (rituximab CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D.T. PACE (dexamethasone, thalidomide, cisplatin, Adriamycin®, cyclophosphamide, etoposide). Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" The New England Journal of Medicine 2008, 359 (6), p. 613-626; and Wierda, W. G., "Current and Investigational Therapies for Patients with CLL" Hematology 2006, p. 285-294. Lymphoma incidence patterns in the United States is profiled in Morton, L. M., et al. "Lymphoma Incidence Patterns by WHO Subtype in the United States, 1992-2001" Blood 2006, 107(1), p. 265-276. In some embodiments, the patient is refractory to at least one, at least two, at least three, or at least four of the above anti-cancer therapy.

In some embodiments, the patient is undergoing treatment of non-Hodgkin's lymphomas (NHL), especially of B-cell origin and the treatment includes the use of monoclonal antibodies, standard chemotherapy approaches (e.g., CHOP, CVP, FCM, MCP, and the like), radioimmunotherapy, or combinations thereof, especially integration of an antibody therapy with chemotherapy. Examples of unconjugated monoclonal antibodies for Non-Hodgkin's lymphoma/B-cell cancers include rituximab, alemtuzumab, human or humanized anti-CD20 antibodies, lumiliximab, anti-TRAIL, bevacizumab, galiximab, epratuzumab, SGN-40, and anti-CD74. Examples of experimental antibody agents used in treatment of Non-Hodgkin's lymphoma/B-cell cancers include ofatumumab, ha20, PRO131921, alemtuzumab, galiximab, SGN-40, CHIR-12.12, epratuzumab, lumiliximab, apolizumab, milatuzumab, and bevacizumab. Examples of standard regimens of chemotherapy for Non-Hodgkin's lymphoma/B-cell cancers include CHOP (cyclophosphamide, doxorubicin, vincristine, prednisone), FCM (fludarabine, cyclophosphamide, mitoxantrone), CVP (cyclophosphamide, vincristine and prednisone), MCP (mitoxantrone, chlorambucil, and prednisolone), R-CHOP (rituximab plus CHOP), R-FCM (rituximab plus FCM), R-CVP (rituximab plus CVP), and R MCP (R MCP). Examples of radioimmunotherapy for Non-Hodgkin's lymphoma/B-cell cancers include yttrium-90-labeled ibritumomab tiuxetan, and iodine-131-labeled tositumomab.

In another example, the patient is undergoing therapeutic treatments for mantle cell lymphoma (MCL) including combination chemotherapies such as CHOP (cyclophosphamide, doxorubicin, vincristine, prednisone), hyperCVAD (hyperfractionated cyclophosphamide, vincristine, doxorubicin, dexamethasone, methotrexate, cytarabine) and FCM (fludarabine, cyclophosphamide, mitoxantrone). In addition, these regimens can be supplemented with the monoclonal antibody rituximab (Rituxan) to form combination therapies R-CHOP, hyperCVAD-R, and R-FCM. Other approaches include combining any of the abovementioned therapies with stem cell transplantation or treatment with ICE (iphosphamide, carboplatin and etoposide). Other approaches to treating mantle cell lymphoma includes immunotherapy such as using monoclonal antibodies like Rituximab (Rituxan). Rituximab can be used for treating indolent B-cell cancers, including marginal-zone lymphoma, WM, CLL and small lymphocytic lymphoma. A modified approach is radioimmunotherapy, wherein a monoclonal antibody is combined with a radioisotope particle, such as Iodine-131 tositumomab (Bexxar®) and Yttrium-90 ibritumomab tiuxetan (Zevalin®). In another example, Bexxar® is used in sequential treatment with CHOP. Another immunotherapy example includes using cancer vaccines, which is based upon the genetic makeup of an individual patient's tumor. A lymphoma vaccine example is GTOP-99 (MyVax®). Yet other approaches to treating mantle cell lymphoma includes autologous stem cell transplantation coupled with high-dose chemotherapy, or treating mantle cell lymphoma includes administering proteasome inhibitors, such as Velcade® (bortezomib or PS-341), or antiangiogenesis agents, such as thalidomide, especially in combination with Rituxan. Another treatment approach is administering drugs that lead to the degradation of Bcl-2 protein and increase cancer cell sensitivity to chemotherapy, such as oblimersen (Genasense) in combination with other chemotherapeutic agents. Another treatment approach includes administering mTOR inhibitors, which can lead to inhibition of cell growth and even cell death; a non-limiting example is Temsirolimus (CCI-779), and Temsirolimus in combination with Rituxan®, Velcade® or other chemotherapeutic agents. Other recent therapies for MCL have been disclosed (Nature Reviews; Jares, P. 2007). Such examples include Flavopiridol, PD0332991, R-roscovitine (Selicilib, CYC202), Styryl sulphones, Obatoclax (GX15-070), TRAIL, Anti-TRAIL DR4 and DR5 antibodies, Temsirolimus (CC1-779), Everolimus (RAD001), BMS-345541, Curcumin, Vorinostat (SAHA), Thalidomide, lenalidomide (Revlimid®, CC-5013), and Geldanamycin (17 AAG).

In some embodiments, the pharmaceutical composition comprising a bis-mesylate salt polymorph of a compound of Formula I selected from Form I, II, VI, XIII, XIV, XV, XVI, XVIII and XIX is administered to a patient that is undergoing treatments for Waldenstrom's Macroglobulinemia. Examples of other therapeutic agents used to treat Waldenstrom's Macroglobulinemia (WM) include perifosine, bortezomib (Velcade®), rituximab, sildenafil citrate (Viagra®), CC-5103, thalidomide, epratuzumab (hLL2-anti-CD22 humanized antibody), simvastatin, enzastaurin, campath-1H, dexamethasone, DT PACE, oblimersen, antineoplaston A10, antineoplaston AS2-1, alemtuzumab, beta alethine, cyclophosphamide, doxorubicin hydrochloride, prednisone, vincristine sulfate, fludarabine, filgrastim, melphalan, recombinant interferon alfa, carmustine, cisplatin, cyclophosphamide, cytarabine, etoposide, melphalan, dolastatin 10, indium In 111 monoclonal antibody MN-14, yttrium Y 90 humanized epratuzumab, anti-thymocyte globulin, busulfan, cyclosporine, methotrexate, mycophenolate mofetil, therapeutic allogeneic lymphocytes, Yttrium Y 90 ibritumomab tiuxetan, sirolimus, tacrolimus, carboplatin, thiotepa, paclitaxel, aldesleukin, recombinant interferon alfa, docetaxel, ifosfamide, mesna, recombinant interleukin-12, recombinant interleukin-11, Bcl-2 family protein inhibitor ABT-263, denileukin diftitox, tanespimycin, everolimus, pegfilgrastim, vorinostat, alvocidib, recombinant flt3 ligand, recombinant human thrombopoietin, lymphokine-activated killer cells, amifostine trihydrate, aminocamptothecin, irinotecan hydrochloride, caspofungin acetate, clofarabine, epoetin alfa, nelarabine, pentostatin, sargramostim, vinorelbine ditartrate, WT-1 analog peptide vaccine, WT1 126-134 peptide vaccine, fenretinide, ixabepilone, oxaliplatin, monoclonal antibody CD19, monoclonal antibody CD20, omega-3 fatty acids, mitoxantrone hydrochloride, octreotide acetate, tositumomab and iodine 1-131 tositumomab, motexafin gadolinium, arsenic trioxide, tipifarnib, autologous human tumor-derived HSPPC-96, veltuzumab, bryostatin 1, and PEGylated liposomal doxorubicin hydrochloride, and any combination thereof.

Examples of therapeutic procedures used to treat WM include peripheral blood stem cell transplantation, cord stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

Examples of other therapeutic agents used to treat diffuse large B-cell lymphoma (DLBCL) drug therapies (Blood 2005 Abramson, J.) include cyclophosphamide, doxorubicin, vincristine, prednisone, anti-CD20 monoclonal antibodies, etoposide, bleomycin, many of the agents listed for Waldenstrom's, and any combination thereof, such as ICE and R ICE.

Examples of other therapeutic agents used to treat chronic lymphocytic leukemia (CLL) (Spectrum, 2006, Fernandes, D.) include Chlorambucil (Leukeran), Cyclophosphamide (Cyloxan, Endoxan, Endoxana, Cyclostin), Fludarabine (Fludara), Pentstatin (Nipent), Cladribine (Leustarin), Doxorubicin (Adriamycin®, Adriblastine), Vincristine (Oncovin), Prednisone, Prednisolone, Alemtuzumab (Campath, MabCampath), many of the agents listed for Waldenstrom's, and combination chemotherapy and chemoimmunotherapy, including the common combination regimen: CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); and FR (fludarabine, rituximab).

Subjects

Any of the methods of treatment provided may be used to treat a subject who has been diagnosed with or is suspected of having a cancer, an allergic disorder and/or an autoimmune and/or inflammatory disease, and/or an acute inflammatory reaction.

In some of the embodiments of any of the methods provided herein, the subject is a human who is at risk of developing a cancer (e.g., a human who is genetically or otherwise predisposed to developing a cancer) and who has or has not been diagnosed with the cancer. As used herein, an "at risk" subject is a subject who is at risk of developing cancer (e.g., a hematologic malignancy). The subject may or may not have detectable disease, and may or may not have displayed detectable disease prior to the treatment methods described herein. An at risk subject may have one or more so-called risk factors, which are measurable parameters that correlate with development of cancer, such as described herein. A subject having one or more of these risk factors has a higher probability of developing cancer than an individual without these risk factor(s).

These risk factors may include, for example, age, sex, race, diet, history of previous disease, presence of precursor disease, genetic (e.g., hereditary) considerations, and environmental exposure. In some embodiments, a subject at risk for cancer includes, for example, a subject whose relatives have experienced this disease, and those whose risk is determined by analysis of genetic or biochemical markers. Prior history of having cancer may also be a risk factor for instances of cancer recurrence.

Provided herein are also methods for treating a subject (e.g., a human) who exhibits one or more symptoms associated with cancer (e.g., a hematologic malignancy). In some embodiments, the subject is at an early stage of cancer. In other embodiments, the subject is at an advanced stage of cancer.

In some embodiments, the subject (e.g., a human) has a cancer responsive to Syk activity. In another embodiment, the human has a solid cancer tumor which expresses Syk. In some embodiments, the human has a 17p deletion, a TP53 mutation, NOTCH1, a SF3B1 mutation, a 11q deletion, or any combination thereof. In one embodiment, the human has a 17p deletion, a TP53 mutation, or a combination thereof. In another embodiment, the human has NOTCH1, a SF3B1 mutation, a 11q deletion, or any combination thereof.

Provided herein are also methods for treating a subject (e.g., a human) who is undergoing one or more standard therapies for treating cancer (e.g., a hematologic malignancy), such as chemotherapy, radiotherapy, immunotherapy, and/or surgery. Thus, in some foregoing embodiments, a bis-mesylate salt of a compound of Formula I (including polymorphs of such bis-mesylate salt, such as Form 3 and/or Form 7), or a hydrate thereof, and compositions described herein is administered before, during, or after administration of chemotherapy, radiotherapy, immunotherapy, and/or surgery.

In another aspect, provided herein are methods for treating a subject (e.g., a human) who is "refractory" to a cancer treatment or who is in "relapse" after treatment for cancer (e.g., a hematologic malignancy). A subject "refractory" to an anti-cancer therapy means they do not respond to the particular treatment, also referred to as resistant. The cancer may be resistant to treatment from the beginning of treatment, or may become resistant during the course of treatment, for example after the treatment has shown some effect on the cancer, but not enough to be considered a remission or partial remission. A subject in "relapse" means that the cancer has returned or the signs and symptoms of cancer have returned after a period of improvement, e.g. after a treatment has shown effective reduction in the cancer, such as after a subject is in remission or partial remission.

In some embodiments, the subject may be a human who is (i) refractory to at least one anti-cancer therapy, or (ii) in relapse after treatment with at least one anti-cancer therapy, or both (i) and (ii). In some of embodiments, the subject is refractory to at least two, at least three, or at least four anti-cancer therapy (including, for example, standard or experimental chemotherapies).

In certain embodiments, the subject is a human who is (i) refractory to, and/or (ii) in relapse after treatment with at least one therapy for chronic lymphocytic leukemia (CLL), mantle cell lymphoma (MCL), diffuse large B-cell lymphoma (DLBCL), follicular lymphoma (FL), or non-FL indolent non-Hodgkin's lymphoma (including, for example, lymphoplasmacytic lymphoma/Waldestrom's macroglobulinemia (LPL/WM), small lymphocytic lymphoma (SLL), and marginal zone lymphoma (MZL)).

In some variations, the subject is a human who (i) is refractory to, and/or (ii) is in relapse after treatment with, and/or (iii) has prior exposure to at least one therapy for a non-FL indolent non-Hodgkin's lymphoma. In certain embodiments, the non-FL indolent non-Hodgkin's lymphoma is lymphoplasmacytic lymphoma/Waldestrom's macroglobulinemia (LPL/WM), small lymphocytic lymphoma (SLL), or marginal zone lymphoma (MZL)). In another variation, the subject is a human who (i) is refractory to, and/or (ii) is in relapse after treatment with, and/or (iii) has prior exposure to at least one therapy for follicular lymphoma (FL). In another variation, the subject is a human who (i) is refractory to, and/or (ii) is in relapse after treatment with, and/or (iii) has prior exposure to at least one therapy for diffuse large B-cell lymphoma (DLBCL). In another variation, the subject is a human who (i) is refractory to, and/or (ii) is in relapse after treatment with, and/or (iii) has prior exposure to at least one therapy for mantle cell lymphoma (MCL). In yet another variation, the subject is a human who (i) is refractory to, and/or (ii) is in relapse after treatment with, and/or (iii) has prior exposure to at least one therapy for chronic lymphocytic leukemia (CLL). In yet another variation, the subject is a human who (i) is refractory to, and/or (ii) is in relapse after treatment with, and/or (iii) has prior exposure to a phosphatidylinositol 3-kinase (PI3K) inhibitor, a bruton tyrosine kinase (BTK) inhibitor, or a B-cell receptor (BCR) treatment for chronic lymphocytic leukemia (CLL).

In some embodiments, the subject is refractory to at least one, at least two, at least three, or at least four anti-cancer therapy (including, for example, standard or experimental chemotherapy) selected from fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D.T. PACE (dexamethasone, thalidomide, cisplatin, Adriamycin®, cyclophosphamide, etoposide).

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" *The New England Journal of Medicine* 2008, 359(6), p. 613-626; and Wierda, W. G., "Current and Investigational Therapies for Patients with CLL" *Hematology* 2006, p. 285-294. Lymphoma incidence patterns in the United States is profiled in Morton, L. M., et al. "Lymphoma Incidence Patterns by WHO Subtype in the United States, 1992-2001" *Blood* 2006, 107(1), p. 265-276.

For example, treatment of non-Hodgkin's lymphomas (NHL), especially of B-cell origin, include the use of monoclonal antibodies, standard chemotherapy approaches (e.g., CHOP, CVP, FCM, MCP, and the like), radioimmunotherapy, and combinations thereof, especially integration of an antibody therapy with chemotherapy. Examples of unconjugated monoclonal antibodies for Non-Hodgkin's lymphoma/B-cell cancers include rituximab, alemtuzumab, human or humanized anti-CD20 antibodies, lumiliximab, anti-TRAIL, bevacizumab, galiximab, epratuzumab, SGN-40, and anti-CD74. Examples of experimental antibody agents used in treatment of Non-Hodgkin's lymphoma/B-cell cancers include ofatumumab, ha20, PRO131921, alemtuzumab, galiximab, SGN-40, CHIR-12.12, epratuzumab, lumiliximab, apolizumab, milatuzumab, and bevacizumab. Examples of standard regimens of chemotherapy for Non-Hodgkin's lymphoma/B-cell cancers include CHOP (cyclophosphamide, doxorubicin, vincristine, prednisone), FCM (fludarabine, cyclophosphamide, mitoxantrone), CVP (cyclophosphamide, vincristine and prednisone), MCP (mitoxantrone, chlorambucil, and prednisolone), R-CHOP (rituximab plus CHOP), R-FCM (rituximab plus FCM), R-CVP (rituximab plus CVP), and R-MCP (R-MCP). Examples of radioimmunotherapy for Non-Hodgkin's lymphoma/B-cell cancers include yttrium-90-labeled ibritumomab tiuxetan, and iodine-131-labeled tositumomab.

In another example, therapeutic treatments for mantle cell lymphoma (MCL) include combination chemotherapies such as CHOP (cyclophosphamide, doxorubicin, vincristine, prednisone), hyperCVAD (hyperfractionated cyclophosphamide, vincristine, doxorubicin, dexamethasone, methotrexate, cytarabine) and FCM (fludarabine, cyclophosphamide, mitoxantrone). In addition, these regimens can be supplemented with the monoclonal antibody rituximab (Rituxan) to form combination therapies R-CHOP, hyperCVAD-R, and R-FCM. Other approaches include combining any of the abovementioned therapies with stem cell transplantation or treatment with ICE (iphosphamide, carboplatin and etoposide). Other approaches to treating mantle cell lymphoma includes immunotherapy such as using monoclonal antibodies like Rituximab (Rituxan). Rituximab can be used for treating indolent B-cell cancers, including marginal-zone lymphoma, WM, CLL and small lymphocytic lymphoma. A modified approach is radioimmunotherapy, wherein a monoclonal antibody is combined with a radioisotope particle, such as Iodine-131 tositumomab (Bexxar®) and Yttrium-90 ibritumomab tiuxetan (Zevalin®). In another example, Bexxar® is used in sequential treatment with CHOP. Another immunotherapy example includes using cancer vaccines, which is based upon the genetic makeup of an individual subject's tumor. A lymphoma vaccine example is GTOP-99 (MyVax®). Yet other approaches to treating mantle cell lymphoma includes autologous stem cell transplantation coupled with high-dose chemotherapy, or treating mantle cell lymphoma includes administering proteasome inhibitors, such as Velcade® (bortezomib or PS-341), or antiangiogenesis agents, such as thalidomide, especially in combination with Rituxan. Another treatment approach is administering drugs that lead to the degradation of Bcl-2 protein and increase cancer cell sensitivity to chemotherapy, such as oblimersen (Genasense) in combination with other chemotherapeutic agents. Another treatment approach includes administering mTOR inhibitors, which can lead to inhibition of cell growth and even cell death; a non-limiting example is Temsirolimus (CCI-779), and Temsirolimus in combination with Rituxan®, Velcade® or other chemotherapeutic agents.

Other recent therapies for MCL have been disclosed (*Nature Reviews*; Jares, P. 2007). Such examples include Flavopiridol, PD0332991, R-roscovitine (Selicilib, CYC202), Styryl sulphones, Obatoclax (GX15-070), TRAIL, Anti-TRAIL DR4 and DR5 antibodies, Temsirolimus (CC1-779), Everolimus (RAD001), BMS-345541, Curcumin, Vorinostat (SAHA), Thalidomide, lenalidomide (Revlimid®, CC-5013), and Geldanamycin (17-AAG).

Examples of other therapeutic agents used to treat Waldenstrom's Macroglobulinemia (WM) include perifosine, bortezomib (Velcade®), rituximab, sildenafil citrate (Viagra®), CC-5103, thalidomide, epratuzumab (hLL2-anti-CD22 humanized antibody), simvastatin, enzastaurin, campath-1H, dexamethasone, DT PACE, oblimersen, antineoplaston A10, antineoplaston AS2-1, alemtuzumab, beta alethine, cyclophosphamide, doxorubicin hydrochloride, prednisone, vincristine sulfate, fludarabine, filgrastim, melphalan, recombinant interferon alfa, carmustine, cisplatin, cyclophosphamide, cytarabine, etoposide, melphalan, dolastatin 10, indium In 111 monoclonal antibody MN-14, yttrium Y 90 humanized epratuzumab, anti-thymocyte globulin, busulfan, cyclosporine, methotrexate, mycophenolate mofetil, therapeutic allogeneic lymphocytes, Yttrium Y 90 ibritumomab tiuxetan, sirolimus, tacrolimus, carboplatin, thiotepa, paclitaxel, aldesleukin, recombinant interferon alfa, docetaxel, ifosfamide, mesna, recombinant interleukin-12, recombinant interleukin-11, Bcl-2 family protein inhibitor ABT-263, denileukin diftitox, tanespimycin, everolimus, pegfilgrastim, vorinostat, alvocidib, recombinant flt3 ligand, recombinant human thrombopoietin, lymphokine-activated killer cells, amifostine trihydrate, aminocamptothecin, irinotecan hydrochloride, caspofungin acetate, clofarabine, epoetin alfa, nelarabine, pentostatin, sargramostim, vinorelbine ditartrate, WT-1 analog peptide vaccine, WT1 126-134 peptide vaccine, fenretinide, ixabepilone, oxaliplatin, monoclonal antibody CD19, monoclonal antibody CD20, omega-3 fatty acids, mitoxantrone hydrochloride, octreotide acetate, tositumomab and iodine 1-131 tositumomab, motexafin gadolinium, arsenic trioxide, tipifarnib, autologous human tumor-derived HSPPC-96, veltuzumab, bryostatin 1, and PEGylated liposomal doxorubicin hydrochloride, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

Examples of other therapeutic agents used to treat diffuse large B-cell lymphoma (DLBCL) drug therapies (*Blood* 2005 Abramson, J.) include cyclophosphamide, doxorubicin, vincristine, prednisone, anti-CD20 monoclonal antibodies, etoposide, bleomycin, many of the agents listed for Waldenstrom's, and any combination thereof, such as ICE and R-ICE.

Examples of other therapeutic agents used to treat chronic lymphocytic leukemia (CLL) (Spectrum, 2006, Fernandes, D.) include Chlorambucil (Leukeran), Cyclophosphamide (Cyloxan, Endoxan, Endoxana, Cyclostin), Fludarabine (Fludara), Pentstatin (Nipent), Cladribine (Leustarin), Doxorubicin (Adriamycin®, Adriblastine), Vincristine (Oncovin), Prednisone, Prednisolone, Alemtuzumab (Campath, MabCampath), many of the agents listed for Waldenstrom's, and combination chemotherapy and chemoimmunotherapy, including the common combination regimen: CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); and FR (fludarabine, rituximab).

In another aspect, provided is a method of sensitizing a subject (e.g., a human) who is (i) refractory to at least one chemotherapy treatment, or (ii) in relapse after treatment with chemotherapy, or both (i) and (ii), wherein the method comprises administering a polymorph bis-mesylate salt of a compound of Formula I, or a pharmaceutical composition thereof, to the subject. A subject who is sensitized is a subject who is responsive to the treatment involving administration of a bis-mesylate salt of a compound of Formula I (including polymorphs of such bis-mesylate salt, such as Form 3 and/or Form 7), or a hydrate thereof, and compositions thereof described herein, or who has not developed resistance to such treatment.

In another aspect, provided herein are methods for treating a subject (e.g., a human) for a cancer, with comorbidity, wherein the treatment is also effective in treating the comorbidity. A "comorbidity" to cancer is a disease that occurs at the same time as the cancer.

In some embodiments, provided herein are methods for treating a subject (e.g., a human) for chronic lymphocytic leukemia (CLL), with comorbidity, wherein the treatment is also effective in treating the comorbidity. Many subjects with CLL will have one or more other diseases, for example diseases affecting the blood pressure system, vascular and heart systems, endocrine and metabolic systems, genitourinary system, musculoskeletal system, respiratory system, neurological system, upper and lower gastrointestinal systems, psychiatric system, ear, nose and throat systems, renal system, or liver system. Specific morbidities of CLL include, but are not limited to, one or more other cancers (e.g. breast, head and neck, lung, melanoma, non-Hodgkin's T-cell lymphoma, prostate, colon, small intestine, gynecologic and urinary tract), hypertension, hyperlipidemia, coronary artery disease, peripheral vascular diseases, cardiomyopathy, vulvular heart disease, atrial fibrillation, cerebrovascular disease (e.g. transient ischemic attack, stroke), chronic obstructive pulmonary disease, joint disease, peptic ulcer, inflammatory bowel disease, psychiatric illness, thyroid disease, benign prostate hyperplasia, diabetes mellitus, and osteoarthritis (Satram-Hoang et al., *Journal of Cancer Therapy,* 2013; 4:1321-1329; Thurmes et al., *Leukemia & Lymphoma,* 2008; 49(1):49-56).

In some embodiments, a method of treating a comorbidity of CLL in a subject (e.g., a human), wherein the method comprises administering a compound of Formula I selected from Form I, II, VI, XIII, XIV, XV, XVI, XVIII and XIX, or a pharmaceutically acceptable salt thereof, or a pharmaceutical composition thereof, to the subject. In some embodiments, the comorbidity is selected from the group consisting of one or more other cancers (e.g. breast, head and neck, lung, melanoma, non-Hodgkin's T-cell lymphoma, prostate, colon, small intestine, gynecologic and urinary tract), hypertension, hyperlipidemia, coronary artery disease, peripheral vascular diseases, cardiomyopathy, vulvular heart disease, atrial fibrillation, cerebrovascular disease (e.g. transient ischemic attack, stroke), chronic obstructive pulmonary disease, joint disease, peptic ulcer, inflammatory bowel disease, psychiatric illness, thyroid disease, benign prostate hyperplasia, diabetes mellitus, and osteoarthritis.

Monotherapy and Combination Therapies

Provided are methods of treatment in which the pharmaceutical composition provided in the present disclosure is administered to a subject (e.g., a human), such that the a polymorph of bis-mesylate salt of a compound of Formula I selected from Form I, II, VI, XIII, XIV, XV, XVI, XVIII and XIX, is the only therapeutic agent administered to the subject. Provided are also methods of treatment in which the pharmaceutical composition provided in the present disclosure administered to a subject (e.g., a human) is given to a subject (e.g., a human) in combination with one or more additional therapeutic agents or other therapies. Both monotherapy and combination therapies are intended and described for use in the methods detailed herein, such as in a method of treating any of the diseases or conditions detailed herein and for use with any subject detailed herein.

Monotherapy

In some embodiments, a method of treating cancer, an allergic disorder and/or an autoimmune and/or inflammatory disease, and/or an acute inflammatory reaction comprises administering to a subject in need thereof an effective amount of a polymorph of bis-mesylate salt of a compound of Formula I selected from Form I, II, VI, XIII, XIV, XV, XVI, XVIII and XIX, wherein the subject is not undergoing therapy for the same disease or condition with another agent or procedure.

In some embodiments one of the above polymorphs is administered as a monotherapy to the subject who has been diagnosed with or is suspected of having a cancer, the subject may be a human who is (i) refractory to at least one anti-cancer therapy, or (ii) in relapse after treatment with at least one anti-cancer therapy, or both (i) and (ii). In some of embodiments, the subject is refractory to at least two, at least three, or at least four anti-cancer therapy (including, for example, standard or experimental chemotherapies). For example, in some embodiments, the subject may be a human who is (i) refractory to a therapy using an anti-CD20 antibody, an alkylating agent (e.g., bendamustine), a purine analog (e.g., fludarabine), an anthracycline, or any combination thereof; (ii) in relapse after treatment with an anti-CD20 antibody, an alkylating agent (e.g., bendamustine), a purine analog (e.g., fludarabine), an anthracycline, or any combination thereof, or both (i) and (ii).

A human subject who is refractory to at least one anti-cancer therapy and/or is in relapse after treatment with at least one anti-cancer therapy, as described above, may have undergone one or more prior therapies. In some embodiments, such subjects have undergone one, two, three, or four, or at least one, at least two, at least three, at least four, or at least five, or between one and ten, between one and nine, between one and eight, between one and seven, between one and six, between one and five, or between one and four, anti-cancer therapies prior to treatment using the methods described herein.

It should be understood that when a subject (e.g. a human) is treated with the compound of Formula I, as a monotherapy, the subject may also undergo one or more other therapies that are not anti-cancer therapies.

Combination Therapies

In some embodiments, a method of treating cancer, an allergic disorder and/or an autoimmune and/or inflammatory disease, and/or an acute inflammatory reaction comprises administering to a subject (e.g., a human) in need thereof an effective amount of the pharmaceutical composition described herein, together with one or more additional therapies (e.g., one or more additional therapeutic agents), which can be useful for treating a cancer, an allergic disorder and/or an autoimmune and/or inflammatory disease, and/or an acute inflammatory reaction.

In some embodiments, a method of treating cancer, an allergic disorder and/or an autoimmune and/or inflammatory disease, and/or an acute inflammatory reaction comprises administering to a subject in need thereof an effective amount of a polymorph of bis-mesylate salt of a compound of Formula I selected from Form I, II, VI, XIII, XIV, XV, XVI, XVIII and XIX, together with a second active agent, which can be useful for treating a cancer, an allergic disorder and/or an autoimmune and/or inflammatory disease, and/or an acute inflammatory reaction. For example the second agent may be an anti-inflammatory agent. Treatment with the second active agent may be prior to, concomitant with one of the above polymorphic forms.

In other embodiments, the one or more additional therapeutic agent may be an inhibitors of lysyl oxidase-like 2 (LOXL2) or a substance that binds to LOXL2, including for example, a humanized monoclonal antibody (mAb) with an immunoglobulin IgG4 isotype directed against human LOXL2. In yet other embodiments, the one or more additional therapeutic agent may be an inhibitor of apoptosis signal-regulating kinase (ASK-1) or a substance that binds to ASK-1. In yet other embodiments, the one or more additional therapeutic agent may be an inhibitor of a Janus kinase, such as JAK1 or JAK2, or a substance that binds to a Janus kinase, such as JAK1 or JAK2. In one embodiment, the one or more additional therapeutic agent is momelotinib. In other embodiments, the one or more additional therapeutic agent may be a Bruton's tyrosine kinase (BTK) inhibitor. In yet other embodiments, the one or more additional therapeutic agent may be a B-cell lymphoma (BCL) inhibitor. In some variations, the BCL inhibitor is a BCL-2 inhibitor. In one variation, the BCL inhibitor is ABT-199.

In yet other embodiments, the one or more additional therapeutic agent may be fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D.T. PACE (dexamethasone, thalidomide, cisplatin, Adriamycin®, cyclophosphamide, etoposide).

In other embodiments, the one or more additional therapeutic agent may be a *vinca*-alkaloid. In one variation, the *vinca*-alkaloid is selected from the group consisting of vincristine, vinblastine, vindesine, vinorelbine, desoxyvincaminol, vincaminol, vinburnine, vincamajine, and vineridine, and pharmaceutically acceptable salts thereof. In certain variations, at least one *vinca*-alkaloid is selected from the group consisting of vincristine, vinblastine, vindesine, vinorelbine, desoxyvincaminol, vincaminol, vinburnine, vincamajine, and vineridine and pharmaceutically acceptable salts thereof. In some variations, the *vinca*-alkaloid is selected from the group consisting of vincristine, vinblastine, vindesine, and vinorelbine, and pharmaceutically acceptable salts thereof. In other variations, the *vinca*-alkaloid is selected from the group consisting of vincristine and vinblastine, and pharmaceutically acceptable salts thereof. In one variation, the *vinca*-alkaloid is vincristine and pharmaceutically acceptable salts thereof. In another variation, the *vinca*-alkaloid is vinblastine and pharmaceutically acceptable salts thereof. Thus, in one aspect, provided is a method for treating cancer in a human in need thereof, comprising administering to the human a polymorph of bis-mesylate salt of a compound of Formula I selected from Form I, II, VI, XIII, XIV, XV, XVI, XVIII and XIX; and a *vinca*-alkaloid, or a pharmaceutically acceptable salt thereof.

In other embodiments, the one or more additional therapies may be any monotherapy or combination therapy suitable for treating leukemia, including, for example, chronic lymphocytic leukemia (CLL), acute lymphocytic leukemia (ALL), and/or acute myeloid leukemia (AML).

In other embodiments, the one or more additional therapeutic agent may be an anti-inflammatory agent. Treatment with the one or more additional therapeutic agent may be prior to, concomitant with, or following treatment with the pharmaceutical composition described herein. In some embodiments, the pharmaceutical composition described herein is combined with another therapeutic agent in a single dosage form. Suitable antitumor therapeutics that may be used in combination with at least one chemical entity described herein include, but are not limited to, chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

The pharmaceutical composition described herein can be useful as chemosensitizing agents, and, thus, can be useful in combination with other chemotherapeutic drugs, in particular, drugs that induce apoptosis.

A method for increasing sensitivity of cancer cells to chemotherapy, comprising administering to a subject (e.g., human) undergoing chemotherapy a chemotherapeutic agent together with the pharmaceutical composition described herein in an amount sufficient to increase the sensitivity of cancer cells to the chemotherapeutic agent is also provided herein. Examples of other chemotherapeutic drugs that can be used in combination with chemical entities described herein include topoisomerase I inhibitors (camptothesin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

In some embodiments, the pharmaceutical composition described herein are used in combination with Rituxan® (Rituximab) or other agents that work by selectively depleting CD20+ B-cells.

Included herein are methods of treatment in which the pharmaceutical composition described herein is administered in combination with an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate. Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an IC50 that is at least 50-fold lower than the IC50 for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates. The anti-inflammatory agent may also be a corticosteroid. For example, the corticosteroid may be chosen from cortisone, dexamethasone, methylprednisolone, prednisolone, prednisolone sodium phosphate, and prednisone. In some embodiments, the anti-inflammatory therapeutic agent is a gold compound such as gold sodium thiomalate or auranofin. In some embodiments, the anti-inflammatory agent is a metabolic inhibitor such as a dihydrofolate reductase inhibitor, such as methotrexate or a dihydroorotate dehydrogenase inhibitor, such as leflunomide.

In some embodiments, combinations in which at least one anti-inflammatory compound is an anti-05 monoclonal antibody (such as eculizumab or pexelizumab), a TNF antagonist, such as entanercept, or infliximab, which is an anti-TNF alpha monoclonal antibody are used.

In some embodiments, combinations in which at least one therapeutic agent is an immunosuppressant compound such as methotrexate, leflunomide, cyclosporine, tacrolimus, azathioprine, or mycophenolate mofetil are used.

It should be understood that any combinations of the additional therapeutic agents described above may be used, as if each and every combination was individually listed. For example, in certain embodiments, the additional therapeutic agents include a PI3K inhibitor and a LOXL2 inhibitor.

Kits

Kits comprising a pharmaceutical composition comprising a polymorph of bis-mesylate salt of a compound of Formula I selected from Form I, II, VI, XIII, XIV, XV, XVI, XVIII and XIX, and at least one pharmaceutical carrier, excipient, adjuvant, or vehicle (e.g., at least one pharmaceutically acceptable polymer) are also provided.

In one aspect, provided is a kit comprising a pharmaceutical composition, comprising: a polymorph of bis-mesylate salt of a compound of Formula I selected from Form I, II, VI, XIII, XIV, XV, XVI, XVIII and XIX; and a pharmaceutical carrier, excipient, adjuvant, or vehicle.

In one aspect, the kit comprises instructions for use in the treatment of cancer or inflammatory conditions. In a particular variation, the instructions are directed to use of the pharmaceutical composition for the treatment of cancer, including for example, leukemia or lymphoma. In certain embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CIVIL), multiple myeloma (MM), indolent non-Hodgkin's lymphoma (iNHL), refractory iNHL, non-Hodgkin's lymphoma (NHL), mantle cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), and marginal zone lymphoma (MZL). In certain embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma, Waldestrom's macroglobulinemia (WM), T-cell lymphoma, B-cell lymphoma, and diffuse large B-cell lymphoma (DLBCL). In one embodiment, the cancer is T-cell acute lymphoblastic leukemia (T-ALL), or B-cell acute lymphoblastic leukemia (B-ALL). In some embodiments, the cancer is MCL, DLBCL, iNHL, FL, MZL, LPL, SLL, or WM. In other embodiments, the cancer is CLL, MCL, DLBCL, iNHL (including, for example, non-FL iNHL), or FL.

The non-Hodgkin lymphoma encompasses the indolent B-cell diseases that include, for example, follicular lymphoma, lymphoplasmacytic lymphoma, Waldenstrom macroglobulinemia, and marginal zone lymphoma, as well as the aggressive lymphomas that include, for example, Burkitt lymphoma, diffuse large B-cell lymphoma (DLBCL) and mantle cell lymphoma (MCL). In one embodiment, the cancer is indolent non-Hodgkin's lymphoma (iNHL). In another embodiment, the cancer is non-FL iNHL.

In a particular variation, the instructions are directed to use of the pharmaceutical composition for the treatment of an autoimmune disease. Certain embodiments of an autoimmune disease include asthma, rheumatoid arthritis, multiple sclerosis, and lupus.

Any pharmaceutical composition provided in the present disclosure may be used in the kits, the same as if each and every composition were specifically and individually listed for use a kit. For example, in one embodiment a kit may comprise: a) about 34% w/w of a polymorph of bis-mesylate salt of a compound of Formula I selected from Form I, II, VI, XIII, XIV, XV, XVI, XVIII and XIX; b) about 15% w/w HPMC; c) about 22% w/w mannitol; d) about 10% w/w crospovidone; and e) about 1% w/w to about 3% w/w poloxamer. In another embodiment, a kit may comprise: a) about 34% w/w of a bis-mesylate salt of a compound of Formula I, or a hydrate thereof; b) about 15% w/w HPMC; c) about 22% w/w mannitol; d) about 10% w/w crospovidone; and e) about 1% w/w to about 3% w/w poloxamer. In yet another embodiment, a kit may comprise: a) about 34% w/w of a monohydrate, bis-mesylate salt of a compound of Formula I; b) about 15% w/w HPMC; c) about 22% w/w mannitol; d) about 10% w/w crospovidone; and e) about 1% w/w to about 3% w/w poloxamer. In yet another embodiment, a kit may comprise: a) about 34% w/w of polymorph Form 3, polymorph Form 7, or a combination thereof; b) about 15% w/w HPMC; c) about 22% w/w mannitol; d) about 10% w/w crospovidone; and e) about 1% w/w to about 3% w/w poloxamer.

Articles of Manufacture

Articles of manufacture comprising a container in which a pharmaceutical composition comprising a polymorph of bis-mesylate salt of a compound of Formula I selected from Form I, II, VI, XIII, XIV, XV, XVI, XVIII and XIX and at least one pharmaceutically acceptable polymer are contained are provided. The article of manufacture may be a bottle, vial, ampoule, single-use disposable applicator, or the like, containing the pharmaceutical composition provided in the present disclosure. The container may be formed from a variety of materials, such as glass or plastic and in one aspect also contains a label on, or associated with, the container which indicates directions for use in the treatment of cancer or inflammatory conditions.

Unit dosage forms of the pharmaceutical composition comprising a polymorph of bis-mesylate salt of a compound of Formula I selected from Form I, II, VI, XIII, XIV, XV, XVI, XVIII and XIX and at least one pharmaceutically acceptable polymer are also provided.

In some embodiments, the unit dosage form comprises from about 10 mg to about 1800 mg, or about 10 mg to about 1500 mg, or about 10 mg to about 1300 mg, or about 10 mg to about 1000 mg, or about 10 mg to about 800 mg, or about 10 mg to about 600 mg, or about 10 mg to about 300 mg, or about 10 mg to about 200 mg, or about 10 mg to about 100 mg, or about 100 mg to about 800 mg, or about 100 mg to about 600 mg, or about 100 mg to about 300 mg, or about 100 mg to about 200 mg, or about 200 mg to about 350 mg, or about 250 mg to about 300 mg, or about 200 mg to about 400 mg, or about 400 mg to about 600 mg, or about 400 mg to about 800 mg, or about 600 mg or about 800 mg, or about 800 mg to about 1200 mg, or about 1200 mg to about 1600 of a polymorph of bis-mesylate salt of a compound of Formula I selected from Form I, II, VI, XIII, XIV, XV, XVI, XVIII and XIX.

In some of the foregoing embodiments, the unit dosage form further comprises at least one pharmaceutically acceptable carrier.

The dosages for oral administration described above may be administered once daily (QD) or twice daily (BID). In some embodiments a polymorph of bis-mesylate salt of a compound of Formula I selected from Form I, II, VI, XIII, XIV, XV, XVI, XVIII and XIX, a pharmaceutical composition of any of the foregoing, is administered orally at a unit dosage of about 1 mg QD, about 2 mg QD, about 5 mg QD, about 10 mg QD, about 15 mg QD, about 20 mg QD, about 25 mg QD, about 30 mg QD, about 35 mg QD, about 40 mg QD, about 45 mg QD, about 50 mg QD, about 75 mg QD, about 100 mg QD, about 125 mg QD, about 150 mg QD, about 175 mg QD, about 200 mg QD, about 225 mg QD, about 250 mg QD, about 300 mg QD, about 350 mg QD, about 400 mg QD, about 450 mg QD, about 500 mg QD, about 550 mg QD, about 600 mg QD, about 650 mg QD, about 700 mg QD, about 750 mg QD, about 800 mg QD, about 850 mg QD, about 900 mg QD, about 950 mg QD, or about 1000 mg QD. In some embodiments a polymorph of bis-mesylate salt of a compound of Formula I selected from Form I, II, XIII, XIV, XV, XVI, XVIII and XIX or a pharmaceutical composition of any of the foregoing, is administered orally at a unit dosage of about 1 mg BID, about 2 mg BID, about 5 mg BID, about 10 mg BID, about 15 mg BID, about 20 mg BID, about 25 mg BID, about 30 mg BID, about 35 mg BID, about 40 mg BID, about 45 mg BID, about 50 mg BID, about 75 mg BID, about 100 mg BID, about 125 mg BID, about 150 mg BID, about 175 mg BID, about 200 mg BID, about 225 mg BID, about 250 mg BID, about 300 mg BID, about 350 mg BID, about 400 mg BID, about 450 mg BID, about 500 mg BID, about 550 mg BID, about 600 mg BID, about 650 mg BID, about 700 mg BID, about 750 mg BID, about 800 mg BID, about 850 mg BID, about 900 mg BID, about 950 mg BID, or about 1000 mg BID.

In one variation of the foregoing, the human has a condition selected from the group consisting of lymphoplasmacytic lymphoma/Waldestrom's macroglobulinemia (LPL/WM), small lymphocytic lymphoma (SLL), marginal zone lymphoma (MZL), follicular lymphoma (FL), diffuse large B-cell lymphoma (DLBCL), mantle cell lymphoma (MCL), and chronic lymphocytic leukemia (CLL), or any combination thereof. In another variation of any of the foregoing, the human is (i) refractory to, and/or (ii) in relapse after treatment with at least one therapy for a non-FL indolent non-Hodgkin's lymphoma. In certain embodiments, the non-FL indolent non-Hodgkin's lymphoma is lymphoplasmacytic lymphoma/Waldestrom's macroglobulinemia (LPL/WM), small lymphocytic lymphoma (SLL), or marginal zone lymphoma (MZL)). In another variation, the human is (i) refractory to, and/or (ii) in relapse after treatment with at least one therapy for follicular lymphoma (FL). In another variation, the human is (i) refractory to, and/or (ii) in relapse after treatment with at least one therapy for diffuse large B-cell lymphoma (DLBCL). In another variation, the human is (i) refractory to, and/or (ii) in relapse after treatment with at least one therapy for mantle cell lymphoma (MCL). In yet another variation, the human is (i) refractory to, and/or (ii) in relapse after treatment with at least one therapy for chronic lymphocytic leukemia (CLL). In yet another variation, the human is (i) refractory to, and/or (ii) in relapse after treatment with a phosphatidylinositol 3-kinase (PI3K) inhibitor, a bruton tyrosine kinase (BTK) inhibitor, or a B-cell receptor (BCR) treatment for chronic lymphocytic leukemia (CLL).

Acute Graft Versus Host Disease (aGVHD), also known as fulminant Graft Versus Host Disease, generally presents symptoms within the first 100 days following allogenic hematopoietic stem cell transplantation and is generally characterized by selective damage to the skin, liver, mucosa, and gastrointestinal tract. Chronic Graft Versus Host Disease (cGVHD) occurs in recipients of allogeneic hematopoietic stem cell transplant (HSCT). GVHD is considered chronic when it occurs >100 days post-transplant, though aspects of cGVHD may manifest themselves prior to the 100 day point and overlap with elements of aGVHD. The present disclosure provides a polymorph of bis-mesylate salt of a compound of Formula I selected from Form I, II, VI, XIII, XIV, XV, XVI, XVIII and XIX for treating graft versus host disease (GVHD) in a human, including acute graft versus host disease (aGVHD) and chronic graft versus host disease (cGVHD), the method comprising administering to the human in need thereof a pharmaceutically effective amount of a compound of a polymorph of bis-mesylate salt of a compound of Formula I selected from Form I, II, VI, XIII, XIV, XV, XVI, XVIII and XIX.

EXAMPLES

The following examples are included to illustrate certain embodiments of the disclosure. It should be appreciated by those of skill in the art that the techniques disclosed herein represent techniques that apply in the practice of the disclosure. Those of skill in the art should, in light of the present disclosure, appreciate that changes can be made in the and still obtain a like or similar result without departing from the spirit and scope of the disclosure.

The polymorphs described herein may be characterized by various methods known in the art, such as X-ray powder diffraction pattern (XRPD), differential scanning calorimetry (DSC), thermal gravimetric analysis (TGA) and dynamic vapor sorption (DVS).

In the following Examples, the term "X" refers to weight equivalents, and "V" refers to volume equivalents. "RH" refers to relative humidity.

Examples: Synthesis of Polymorph Forms I, II, VI, XIII, XV, XVI, XVIII and XIX

Methods for generally making various forms of the compound of Formula I may be found in U.S. Pat. Nos. 8,450, 321 and 8,455,493. The following is a method for producing polymorph Form 3, which is described in U.S. Patent Publication No. 20150038505.

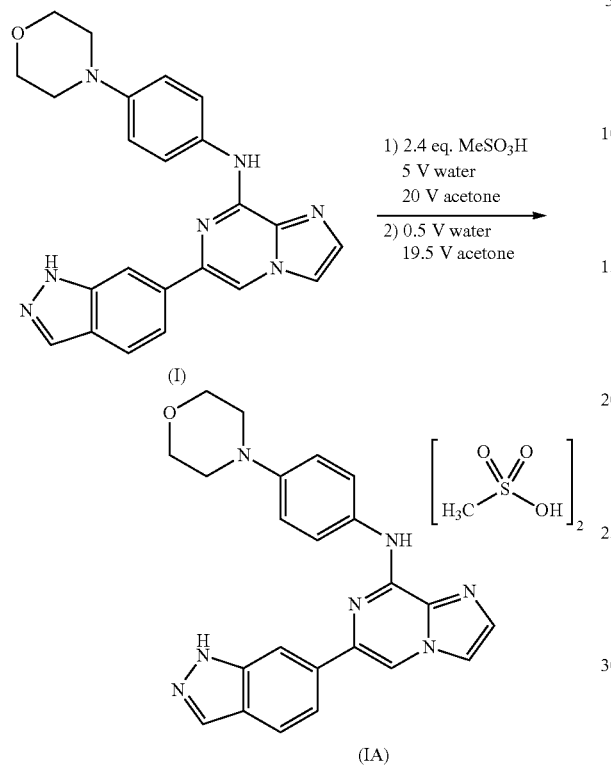

Polymorphic Forms 3 (referred herein as Form III) and 7 (referred herein as Form VII) are disclosed in U.S. Patent Publication No. 2015/0038505, the contents of which are incorporated by reference herein.

Preparation of Form 7: The compound of Formula I (1.0×) was added to reaction vessel A. Methanesulfonic acid (0.56×, 2.40 eq), water (4×, 4 V) and acetone (3.2×, 4 V) were added to reaction vessel B. The contents of reaction vessel B were added to reaction vessel A while maintaining the temperature in reaction vessel A below 35° C. After the solids dissolved, the resulting solution of reaction vessel B was adjusted to 19-25° C. Under high agitation, acetone (11.9×, 15 V) was added to reaction vessel B and the content temperature resulting slurry of Reaction Vessel B was adjusted to 0-6° C., and the contents of reaction vessel B were mixed for 5 h. The slurry was filtered, and rinsed with acetone (4.0×, 5 V) to provide polymorph Form 7. Form 7 was dried under vacuum at 60° C.

The isolated polymorph Form 7, acetone (15.4×, 19.5 V), and water (0.5×, 0.5 V) were combined and added to Polymorph Form 3 seeds (0.01×, 1 mol %). Acetone (15.4×, 19.5 V), and water (0.5×, 0.5 V) were added to reaction vessel B and the resulting slurry was agitated at 20-40° C. until polymorph Form 7 was converted to Form 3. The conversion was monitored by XRPD or DSC. The slurry was adjusted to 19-25° C., was filtered, and rinsed with acetone (2.4×, 3 V). The wet cake was dried under vacuum at 60° C. until constant weight was achieved.

Form 3: The following is a method for producing polymorph Form 3, a hydrate, bis-mesylate salt of a compound of Formula I (which may also be described as a polymorph of a hydrate of the compound of Formula IA shown in the reaction scheme below).

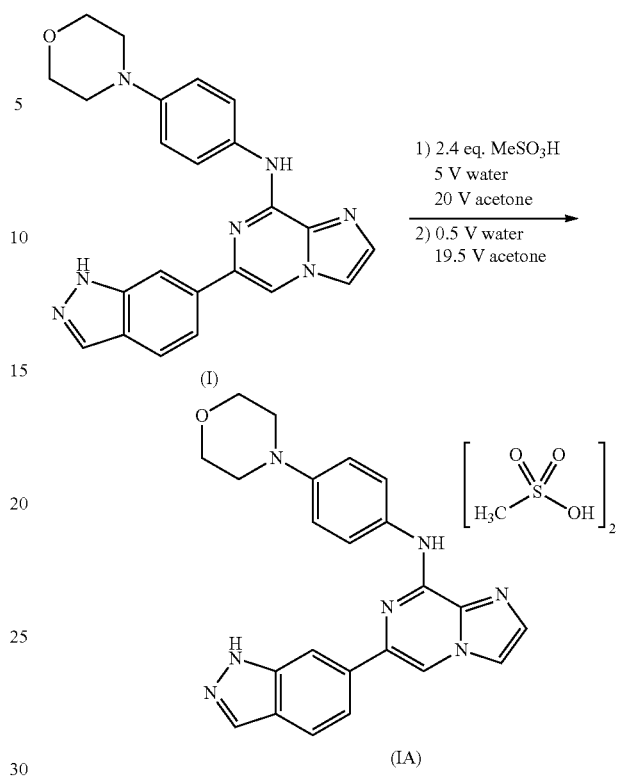

Polymorph Form 7 was obtained as described in Example above.

The isolated polymorph Form 7 was added to polymorph Form 3 seeds of a compound of Formula IA (0.01×, 1 mol %) in reaction vessel B. Acetone (15.0×, 19.0 V), and water (1.0×, 1.0 V) were added to reaction vessel B. The mixture was heated to reflux (about 55° C.) until polymorph Form 7 was converted to Form 3. The conversion was monitored by XRPD or DSC. The contents of reaction vessel B was a slurry and was cooled to 19-25° C., then filtered, rinsed with acetone (2.4×, 3 V) and dried under vacuum at 60° C. until constant weight is achieved to provide the polymorph Form 3.

Figure 8D:
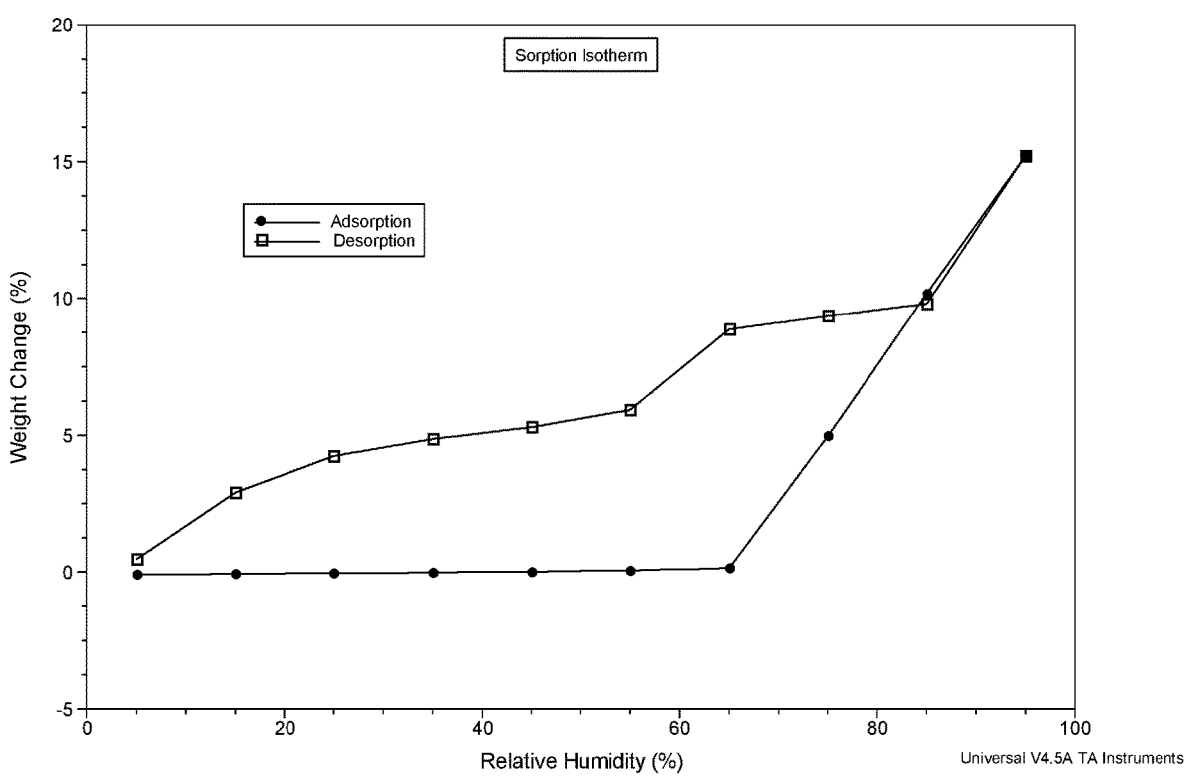
FIG. 8D shows the DVS plot of Form VI.

Synthesis of Polymorph Form VI: Form VI was isolated when reaction vessel A was charged with formic acid (3V, 3.6×) and ethyl acetate (2V, 1.8×) and the contents of the reaction vessel adjusted to 22° C. (19-25° C.). Free base of the compound of Formula I (1.0×) was added portion wise with agitation while maintaining the reaction vessel temperature at 22° C. (19-25° C.) and the contents agitated until all solids dissolved (about 1 hour). The solution in reaction vessel A was transferred to reaction vessel B, and formic acid (0.08V, 0.1×) was added to reaction vessel A along with ethyl acetate (2V, 1.8×), and methyl sulfonic acid (pharmaceutical grade, 2.0 mol equiv., 0.47×). The solution in reaction vessel A was transferred via polishing filter to reaction vessel B over 30 minutes while maintain a pot temperature of 22° C. (19-25° C.). Ethyl acetate (5V, 4.5×) was added to reaction vessel A and then to reaction vessel B over a minimum of 1 hour. The contents of reaction vessel B was agitated for 16 h. at 22° C. (19-25° C.), then filtered rinsed with ethyl acetate (4V, 3.6×) and dried under vacuum at 60° C. Its XRPD pattern is shown in FIG. 8A and is characterized by sharp reflections, indicating crystallinity. Thermal data is shown in FIGS. 2 and 3. The DSC curve indicates multiple endothermic transitions at 71, 184, 206, and 255° C. The TGA curve shows a weight loss (6.7% room temperature to 175° C.) indicating a solvate that was identified as formic acid via ion chromatography. Weight loss above 225° C. is attributed to decomposition. The dynamic vapor sorption curve for Form VI is shown in FIG. 8D and the data indicated that the form absorbs ~17 wt. % of water up to 95% relative humidity (RH) at 25° C. XRPD analysis of the sample after the DVS experiment shows that the material had converted to Form VII.

Synthesis of Polymorph Form I: Form I was isolated by heating Form VI at about 150° C. for about two hours in an open reaction vessel followed by cooling to room temperature or by Form III at about 175° C. for about two hours in an open reaction vessel followed by cooling to room temperature. XRPD analysis of the sample after the DVS experiment shows that the material had converted to Form VII.

Synthesis of Polymorph Form II: Form II was isolated by heating Form VI under vacuum at about 120° C. overnight, as well as slurring Form VI in isopropyl alcohol at room temperature for about 1 week.

Synthesis of Polymorph Form XIII: Form XIII was isolated by exposing Form VII to about 0% RH in a $P_2O_5$ chamber heated to about 40° C. under vacuum for approximately 4 days.

Synthesis of Polymorph Form XIV: Form XIV was isolated by heating Form I, Form II, Form III, or Form XVI to about 250° C. on a DSC.

Synthesis of Polymorph Form XV: Form XV was prepared by slurring a mixture of Form III and Form XV in 2.5% water in acetone at room temperature for about 5 days. It can also be made by slurring Form VII in 4% water in acetone at room temperature for about 3 days.

Synthesis of Polymorph Form XVI: Form XVI was prepared by slurring Form VII in acetone at room temperature for about 1 day or slurring Form XIX in 1% water in acetone or 2% water in acetone for about 1-5 days at room temperature.

Synthesis of Polymorph Form XVIII: Form XVIII was isolated from solvent-wet starting material of compound of Formula I, from 20% water in acetone and drying it in an oven at about 80° C. under vacuum.

Figure 9A:
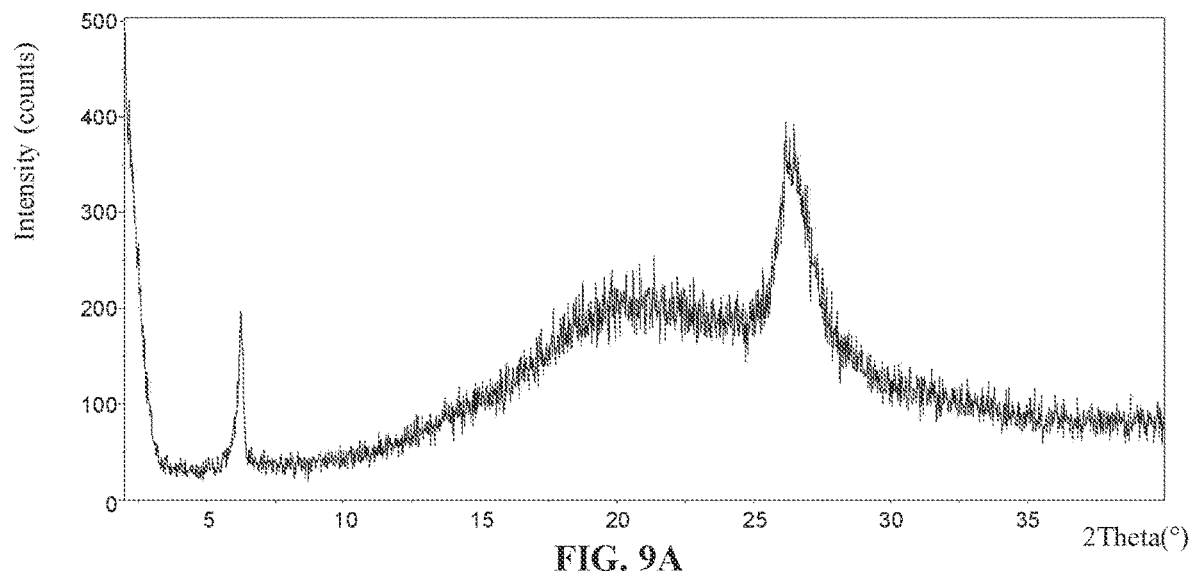
FIG. 9A is an exemplary XRPD pattern of polymorph Form XIX.
Figure 9B:
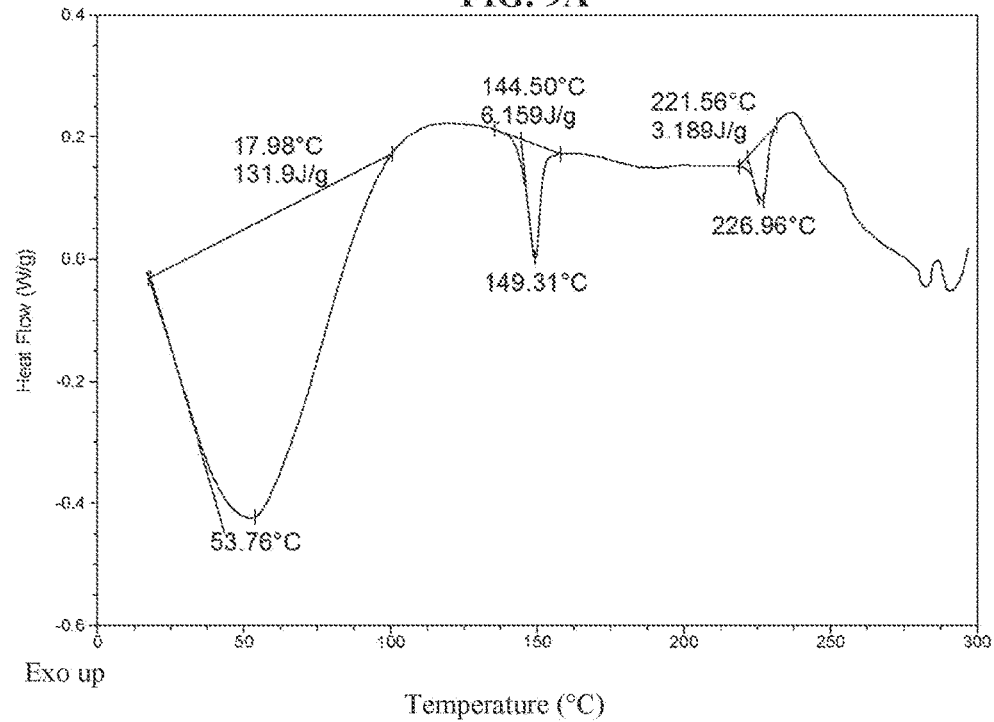
FIG. 9B is an exemplary DSC plot of polymorph Form XIX.
Figure 9C:
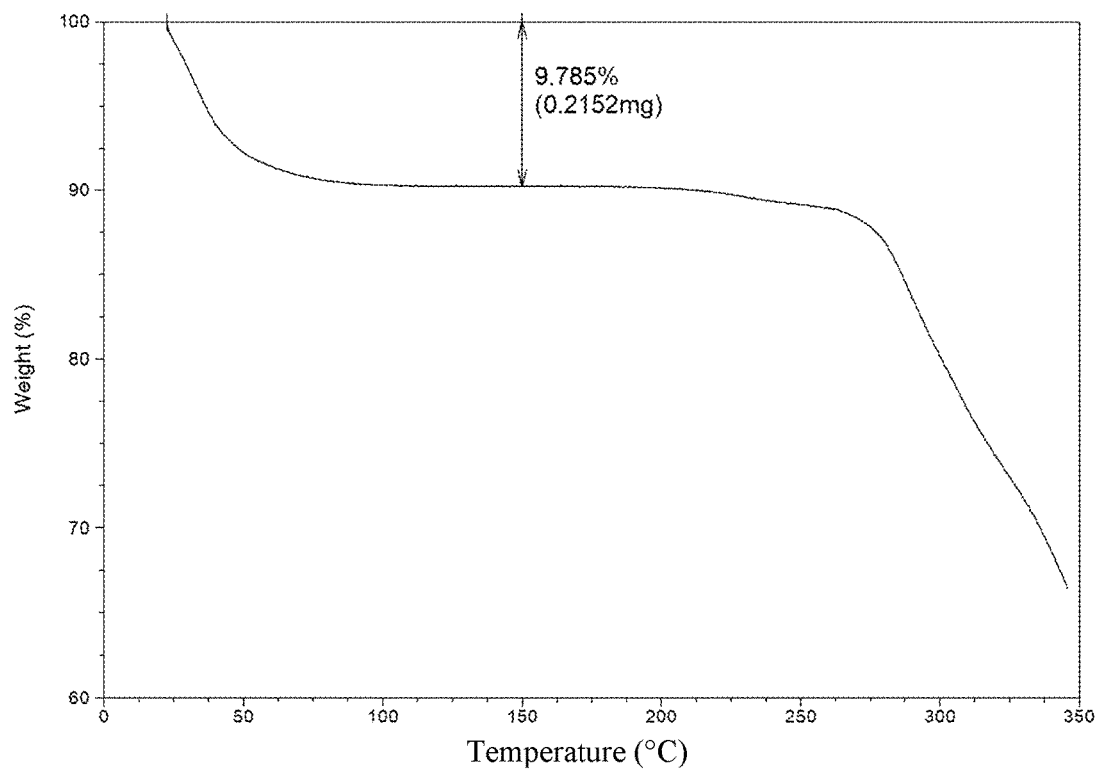
FIG. 9C is an exemplary TGA plot of polymorph Form XIX.
Figure 9D:
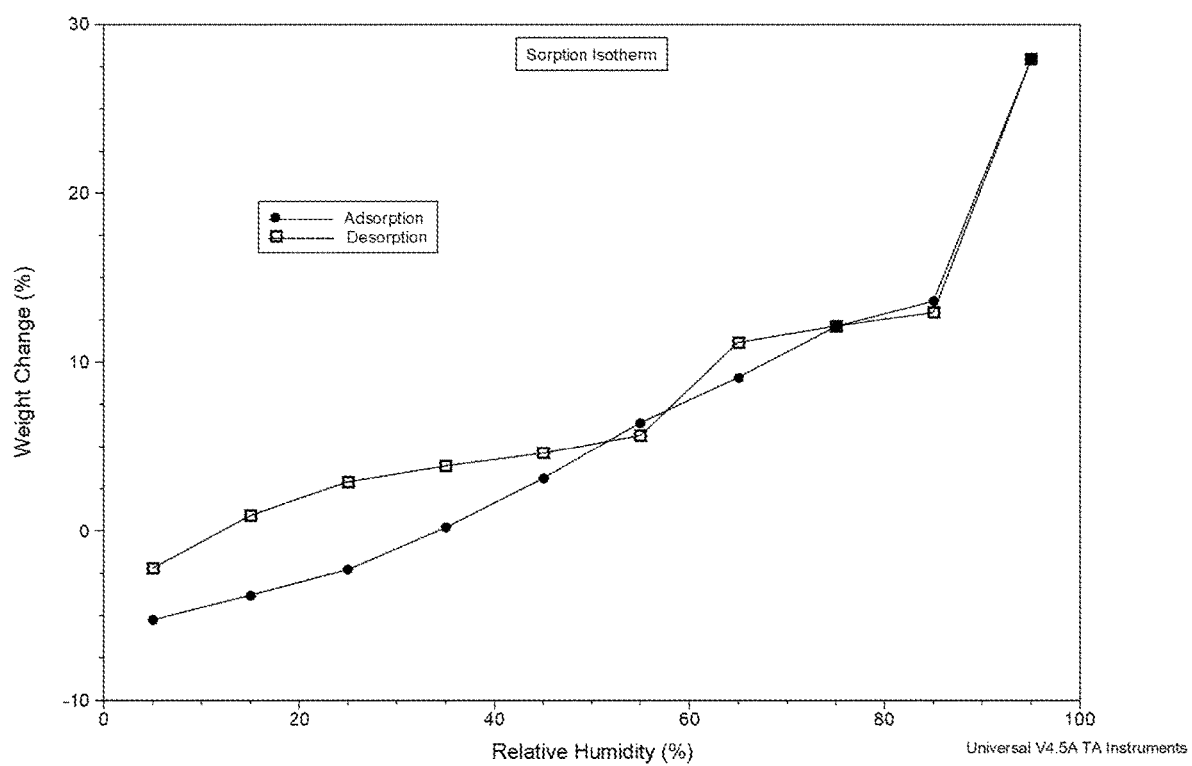
FIG. 9D shows the DVS plot of Form XIX.

Synthesis of Polymorph Form XIX: Form XIX was isolated when about 20 grams of Form III was dissolved in about 180 mL of water. This solution was then then spray-dried as neat API on a Buchi lab scale spray dryer having an outlet temperature of about 82° C., an inlet temperature of about 150° C., a condenser temperature of about 10° C., and a feed rate of 4.0-6.0 mL/min. Its XRPD pattern is shown in FIG. 9A, which has two broad reflections at 6.3 and 26.3° 2θ. Thermal data are shown in FIGS. 9B and 9C. The DSC curve indicates multiple endothermic transitions at 18, 145, and 222° C. The TGA curve shows a weight loss of 9.8% from room temperature to 150° C. The dynamic vapor sorption curve for Form XIX is shown in FIG. 9D and the data indicates that the form absorbs about 28 wt. % of water up to about 95% relative humidity (RH) at 25° C. XRPD analysis of the sample after the DVS experiment shows that the material had converted to Form VII.

Figure 10A:
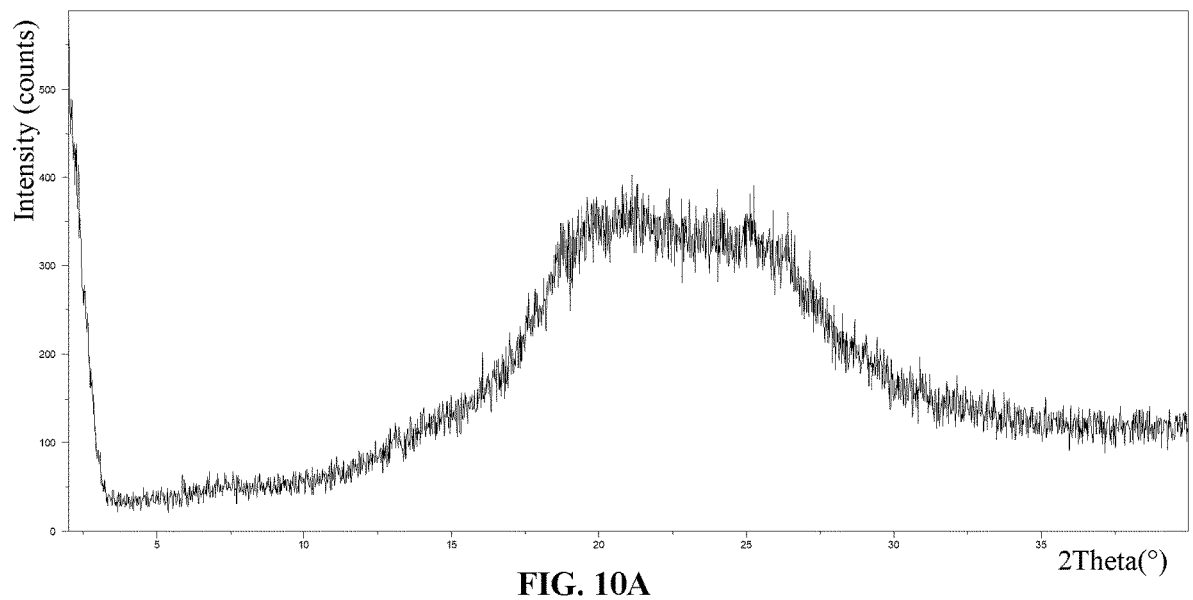
FIG. 10A is an exemplary XRPD pattern of the amorphous form.
Figure 10B:
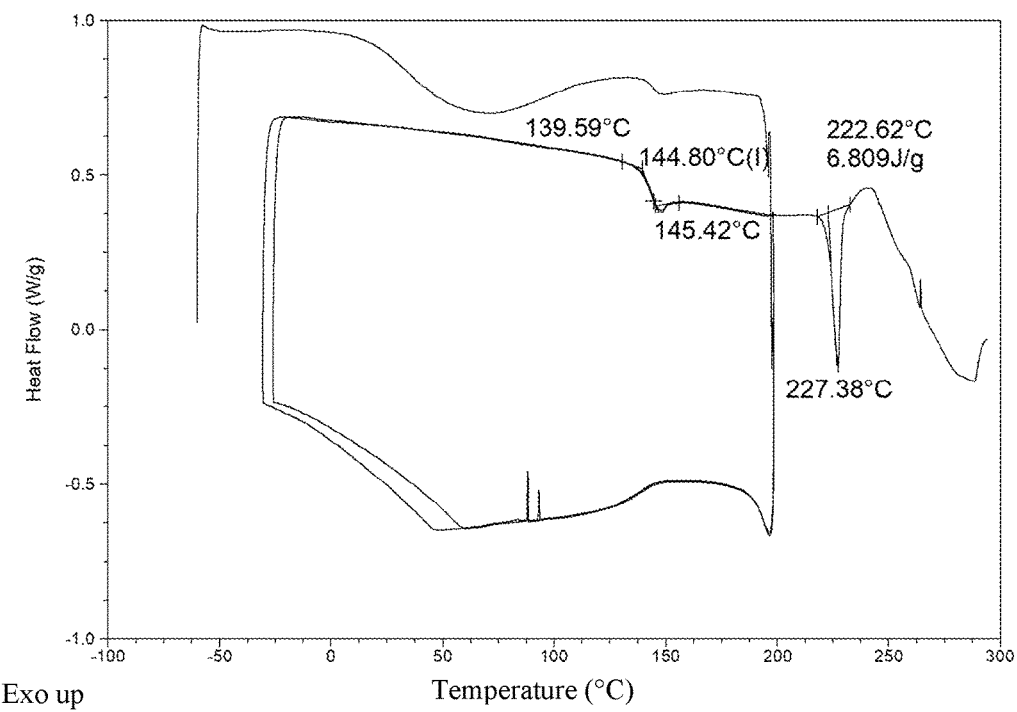
FIG. 10B is an exemplary DSC plot of the amorphous form.
Figure 10C:
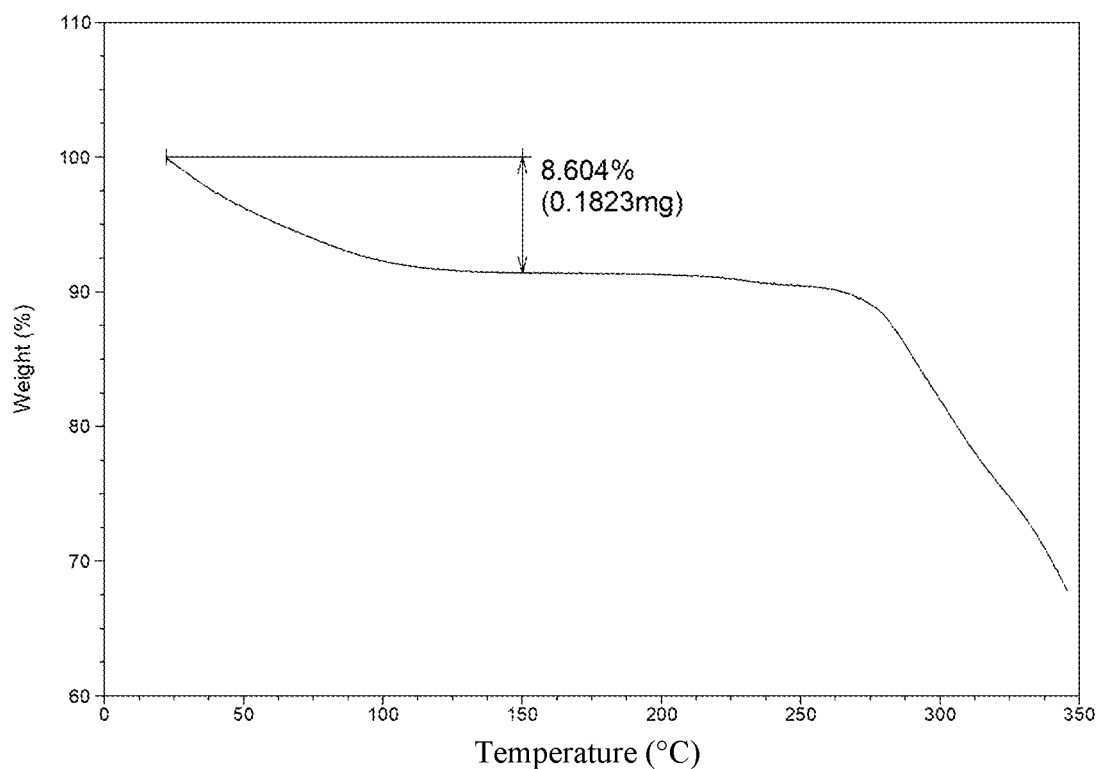
FIG. 10C is an exemplary TGA plot of the amorphous form.
Figure 10D:
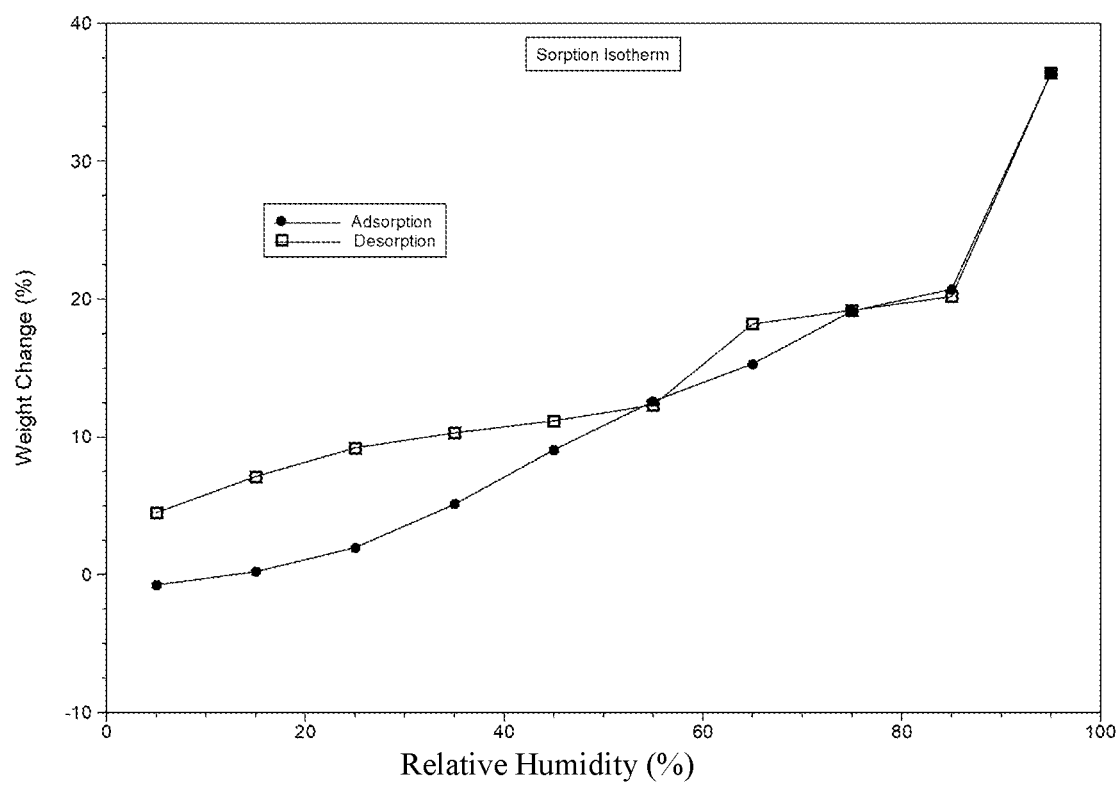
FIG. 10D shows the DVS plot of the amorphous form.

Synthesis of Amorphous Form: Amorphous form of the bis-mesylate salt of the Compound of Formula I was isolated when Form XIX was heat cycled on a DSC from about 60 to 200° C. for three cycles. Its XRPD pattern is shown in FIG. 10A and is characterized by an amorphous halo. Thermal data are shown in FIGS. 10B and 10C. The DSC curve indicates a glass transition around 140° C. and an endotherm at 222° C. The TGA curve shows a weight loss of 8.6% from room temperature to 150° C. The dynamic vapor sorption curve for the amorphous phase is shown in FIG. 10D and the data indicates that the form absorbs about 38 wt. % of water up to about 95% relative humidity (RH) at 25° C. XRPD analysis of the sample after the DVS experiment shows that the material had converted to Form VII.

Measurements

X-ray powder diffraction (XRPD) analysis was conducted on a diffractometer (PANalytical XPERT-PRO, PANalytical B. V., Almelo, Netherlands) using copper radiation (Cu Kα, λ=1.541874). Samples were spread evenly on a zero background sample plate. The generator was operated at a voltage of 45 kV and amperage of 40 mA. Slits were Soller 0.02 rad, antiscatter 1.0°, and divergence. Scans were performed from 2 to 40°2θ with a 0.0167 step size. Data analysis was performed using X'Pert Data Viewer V1.2d (PANalytical B.V., Almelo, Netherlands).

Differential Scanning Calorimetry (DSC) was run by loading 1-5 mg of material into a crimped Tzero standard aluminum pan and heating the sample at 10° C./min from 20 to 300° C. or above. The sample and reference pans were under a 50 mL/min nitrogen purge. Data analysis was completed using Universal Analysis 2000 Version 4.7A (TA Instruments, New Castle, Del.).

Thermogravimetric analysis (TGA) was used to evaluate sample weight loss as a function of temperature by loading 1-10 mg of material onto a an aluminum weigh pan (TA Instruments, New Castle, Del.) and heated the sample to 200° C. or above at a rate of 10° C./min. The sample and reference pans were under a 60 mL/min and 40 mL/min nitrogen purge, respectively. Data analysis was completed using Universal Analysis 2000 Version 4.7A (TA Instruments, New Castle, Del.).

Hygroscopicity was studied using dynamic vapor sorption (DVS, TA Q5000 SA, TA Instruments, New Castle, Del. or DVS, DVS Intrinsic, Surface Measurement Systems, London, UK). A sample (2-20 mg) was placed in an aluminum DVS pan and loaded on the sample side of the twin pan balance. The water sorption and desorption were studied as a function of relative humidity (RH) at 25° C. In 10% RH increments, the relative humidity was increased from 5% RH to 95% RH and then decreased back to 5%. Each relative humidity increment had an equilibration time of 180 minutes, unless weight change % was less than 0.002% in 30 minutes. Data analysis was performed using Universal Analysis 2000 Version 4.7A (TA Instruments, New Castle, Del.) for TA DVS runs and Microsoft Excel for SMS DVS runs.

Throughout this specification, various patents, patent applications and other types of publications (e.g., journal articles) are referenced. The disclosure of all patents, patent applications, and publications cited herein are hereby incorporated by reference in their entirety for all purposes.

What is claimed is:

1. A polymorphic form of a compound of Formula IA:

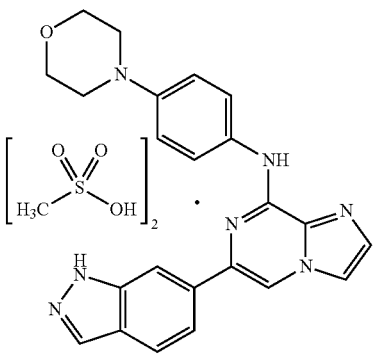

wherein the polymorphic form is a hydrate selected from the group consisting of Form I, Form II, Form XIII, Form XV, Form XVI, and Form XVIII.

2. The polymorphic form of claim 1, wherein the polymorphic form is Form I;
wherein Form I is characterized by a powder X-ray diffraction pattern comprising characteristic peaks (°2θ) at 6.6°±0.2°2θ, 17.1°±0.2°2θ, and 21.3°±0.2°2θ.

3. The polymorphic form of claim 2, wherein the polymorphic form is further characterized by a powder X-ray diffraction pattern comprising at least one additional characteristic peak (°2θ) selected from the group consisting of 14.1°±0.2°2θ, 14.8°±0.2°2θ, 16.0°±0.2°2θ, 22.2°±0.2°2θ, and 24.3°±0.2°2θ.

4. The polymorphic form of claim 1, wherein the polymorphic form is Form II;
wherein Form II is characterized by a powder X-ray diffraction pattern comprising characteristic peaks (°2θ) at 14.8°±0.2°2θ, 17.4°±0.2°2θ, and 20.1°±0.2°2θ.

5. The polymorphic form of claim 4, wherein the polymorphic form is further characterized by a powder X-ray diffraction pattern comprising at least one additional characteristic peak (°2θ) selected from the group consisting of 5.9°±0.2°2θ, 7.9°±0.2°2θ, 13.6°±0.2°2θ, 20.6°±0.2°2θ, and 26.5°±0.2°2θ.

6. The polymorphic form of claim 1, wherein the polymorphic form is Form XIII;
wherein Form XIII is characterized by a powder X-ray diffraction pattern comprising characteristic peaks (°2θ) at 11.6°±0.2°2θ, 17.4°±0.2°2θ, and 19.5°±0.2°2θ.

7. The polymorphic form of claim 6, wherein the polymorphic form is further characterized by a powder X-ray diffraction pattern comprising at least one additional characteristic peak (°2θ) selected from the group consisting of 15.4°±0.2°2θ, 21.3°±0.2°2θ, 21.8°±0.2°2θ, and 26.8°±0.2°2θ.

8. The polymorphic form of claim 1, wherein the polymorphic form is Form XV;
wherein Form XV is characterized by a powder X-ray diffraction pattern comprising characteristic peaks (°2θ) at 20.6°±0.2°2θ, 22.0°±0.2°2θ, and 25.7°±0.2°2θ.

9. The polymorphic form of claim 8, wherein the polymorphic form is further characterized by a powder X-ray diffraction pattern comprising at least one additional characteristic peak (°2θ) selected from the group consisting of 7.0°±0.2°2θ, 13.2°±0.2°2θ, 15.3°±0.2°2θ, 19.6°±0.2°2θ, and 26.7°±0.2°2θ.

10. The polymorphic form of claim 1, wherein the polymorphic form is Form XVI;
wherein Form XVI is characterized by a powder X-ray diffraction pattern comprising characteristic peaks (°2θ) at 7.8°±0.2°2θ, 19.8°±0.2°2θ, and 22.2°±0.2°2θ.

11. The polymorphic form of claim 10, wherein the polymorphic form is further characterized by a powder X-ray diffraction pattern comprising at least one additional characteristic peak (°2θ) selected from the group consisting of 5.0°±0.2°2θ, 14.8°±0.2°2θ, 17.3°±0.2°2θ, 17.8°±0.2°2θ, and 26.0°±0.2°2θ.

12. The polymorphic form of claim 1, wherein the polymorphic form is Form XVIII;
wherein Form XVIII is characterized by a powder X-ray diffraction pattern comprising characteristic peaks (°2θ) at 4.5°±0.2°2θ, 8.9°±0.2°2θ, and 22.1°±0.2°2θ.

13. The polymorphic form of claim 12, wherein the polymorphic form is further characterized by a powder X-ray diffraction pattern comprising at least one additional characteristic peak (°2θ) selected from the group consisting of 13.3°±0.2°2θ, 18.0°±0.2°2θ, 24.7°±0.2°2θ, 27.2°±0.2°2θ, and 31.6°±0.2°2θ.

14. A method for inhibiting spleen tyrosine kinase activity in a human in need thereof, wherein the method comprises administering to the human the polymorphic form of claim 1.

15. The method of claim 14, wherein the human has a condition selected from the group consisting of an autoimmune disease, a cancer, and an inflammatory disease.

16. The method of claim 15, wherein the autoimmune disease, cancer, or inflammatory disease is selected from the group consisting of acute graft-versus-host disease, an acute inflammatory reaction, acute lymphocytic leukemia, acute myeloid leukemia, Addison's disease, adult respiratory distress syndrome, Alzheimer's disease, asthma, atherosclerosis, an autoimmune hemolytic state, an autoimmune thrombocytopenic state, B-cell acute lymphoblastic leukemia, B-cell lymphoma, Burkitt lymphoma, chronic graft-versus-host disease, chronic idiopathic thrombocytopenic purpura, chronic lymphocytic leukemia, chronic myeloid leukemia, chronic obstructive pulmonary disease, Crohn's disease, dermatomyositis, diabetes, follicular lymphoma, glomerulonephritis, Goodpasture's syndrome, hyperacute rejection of a transplanted organ, irritable bowel syndrome, lymphoplasmacytic lymphoma, mantle cell lymphoma, marginal zone lymphoma, multiple myeloma, multiple sclerosis, myasthenia gravis, myelodysplastic syndrome, myeloproliferative disease, non-Hodgkin's lymphoma, Parkinson's disease, polycystic kidney disease, psoriasis, pulmonary hemorrhage, rheumatoid arthritis, scleroderma, septic shock, Sjogren's disease, small lymphocytic lymphoma, systemic lupus erythematosus, T-cell acute lymphoblastic leukemia, T-cell lymphoma, tissue graft rejection, ulcerative colitis, vasculitis, and Waldestrom's macroglobulinemia.

17. The method of claim 16, wherein the acute inflammatory reaction is appendicitis, cholocystitis, dermatitis, encephalitis, enteritis, gastritis, gingivitis, hepatitis, inflammatory bowel disease, inflammatory pelvic disease, meningitis, myocarditis, myositis, nephritis, osteomyelitis, pancreatitis, pneumonitis, skin sunburn, sinusitis, urethritis, or uveitis.

18. The method of claim 16, wherein the B-cell lymphoma is diffuse large B-cell lymphoma.

19. The method of claim 16, wherein the non-Hodgkin's lymphoma is indolent non-Hodgkin's lymphoma.

20. The method of claim 19, wherein the indolent non-Hodgkin's lymphoma is refractory indolent non-Hodgkin's lymphoma.

21. The method of claim 16, wherein the vasculitis is anti-neutrophil cytoplasmic antibody associated vasculitis.

* * * * *